United States Patent
Maclellan et al.

(10) Patent No.: US 12,086,986 B2
(45) Date of Patent: Sep. 10, 2024

(54) SYSTEMS AND METHODS FOR USING ARTIFICIAL INTELLIGENCE FOR SKIN CONDITION DIAGNOSIS AND TREATMENT OPTIONS

(71) Applicant: Cortina Health, Inc., Chattanooga, TN (US)

(72) Inventors: Reid Maclellan, Lookout Mountain, TN (US); Paul Roossin, New York, NY (US)

(73) Assignee: Cortina Health, Inc., Chattanooga, TN (US)

( * ) Notice: Subject to any disclaimer, the term of this patent is extended or adjusted under 35 U.S.C. 154(b) by 509 days.

(21) Appl. No.: 17/398,971

(22) Filed: Aug. 10, 2021

(65) Prior Publication Data

US 2022/0051409 A1    Feb. 17, 2022

Related U.S. Application Data

(60) Provisional application No. 63/064,061, filed on Aug. 11, 2020.

(51) Int. Cl.
*G06T 7/90* (2017.01)
*A61B 5/00* (2006.01)
(Continued)

(52) U.S. Cl.
CPC ............ *G06T 7/0016* (2013.01); *A61B 5/441* (2013.01); *G06F 17/18* (2013.01); *G06T 7/90* (2017.01);
(Continued)

(58) Field of Classification Search
CPC ... A61B 2576/02; A61B 5/1032; A61B 5/441; A61B 5/444; G06F 17/18; G06T 2200/24;
(Continued)

(56) References Cited

U.S. PATENT DOCUMENTS 9,305,359 B2 *  4/2016 Suzuki ................. G06V 10/56
9,786,084 B1 * 10/2017 Bhat .................... G06T 15/04
(Continued)

FOREIGN PATENT DOCUMENTS

WO   WO-2020/116917 A2   6/2020

OTHER PUBLICATIONS

Jufeng Yang, "Clinical Skin Lesion Diagnosis using Representations Inspired by Dermatologist Criteria," Jun. 2018, Proceedings of the IEEE Conference on Computer Vision and Pattern Recognition (CVPR), 2018, pp. 1258-1264.*

(Continued)

*Primary Examiner* — Omar S Ismail
(74) *Attorney, Agent, or Firm* — Foley & Lardner LLP

(57) ABSTRACT

Methods, systems, and storage media for determining a numerical classification of human skin color, determining one or more characteristics of skin based on images, and determining a personalized treatment plan for one or more skin conditions or issues are disclosed. The system can receive images of skin and access user profile information, such as biometric information, medical record information, and other clinically relevant information. The system can determine a classification of a skin color of the user using the image and the biometric information by providing the image and the biometric information as input to a skin color classifier. Using the skin color, the system can determine one or more characteristics of the skin in the image and, if needed, determine and provide at least one personalized treatment plan to a computing device of a user.

17 Claims, 33 Drawing Sheets

(51) Int. Cl.
  *G06F 17/18* (2006.01)
  *G06T 7/00* (2017.01)
  *G16H 10/60* (2018.01)

(52) U.S. Cl.
  CPC ......... *G16H 10/60* (2018.01); *G06T 2200/24* (2013.01); *G06T 2207/10024* (2013.01); *G06T 2207/30088* (2013.01)

(58) Field of Classification Search
  CPC . G06T 2207/10024; G06T 2207/20081; G06T 2207/20084; G06T 2207/30088; G06T 7/0012; G06T 7/0016; G06T 7/90; G16H 10/20; G16H 10/60; G16H 20/00; G16H 30/20; G16H 30/40; G16H 40/67; G16H 50/20; G16H 50/30; G16H 50/70; G16H 70/20
  See application file for complete search history.

(56) References Cited

U.S. PATENT DOCUMENTS

| | | | |
|---|---|---|---|
| 9,842,358 B1 | 12/2017 | Butler et al. | |
| 2006/0269111 A1* | 11/2006 | Stoecker | G16H 30/40 382/128 |
| 2009/0245603 A1* | 10/2009 | Koruga | A61B 5/444 382/128 |
| 2010/0111370 A1* | 5/2010 | Black | G06F 18/2321 705/26.1 |
| 2012/0283530 A1* | 11/2012 | Maynard | G06V 40/10 600/479 |
| 2012/0321759 A1* | 12/2012 | Marinkovich | A61B 5/442 356/402 |
| 2014/0304629 A1 | 10/2014 | Cummins et al. | |
| 2014/0313303 A1* | 10/2014 | Davis | A61B 5/68 348/77 |
| 2014/0316235 A1* | 10/2014 | Davis | G16H 50/20 600/407 |
| 2014/0378810 A1* | 12/2014 | Davis | G06F 16/248 600/407 |
| 2015/0313532 A1* | 11/2015 | Marinkovich | A61B 5/486 600/306 |
| 2016/0275343 A1* | 9/2016 | Dinerstein | G06V 40/162 |
| 2017/0075415 A1* | 3/2017 | Kim | G06F 1/163 |
| 2017/0156593 A1* | 6/2017 | Ferber | A61B 5/0008 |
| 2017/0245759 A1* | 8/2017 | Jain | A61B 5/163 |
| 2017/0246473 A1* | 8/2017 | Marinkovich | G16H 30/40 |
| 2017/0340267 A1 | 11/2017 | Shen et al. | |
| 2018/0303406 A1 | 10/2018 | McKinney et al. | |
| 2019/0035149 A1* | 1/2019 | Chen | G06V 40/166 |
| 2019/0122411 A1* | 4/2019 | Sachs | G06T 7/90 |
| 2019/0142334 A1 | 5/2019 | Von Sobbe | |
| 2020/0170564 A1* | 6/2020 | Jiang | G06T 7/0012 |
| 2020/0380674 A1* | 12/2020 | Ding | G06T 7/0012 |

OTHER PUBLICATIONS

Philipp Tschandl, "Data Descriptor: The HAM10000 dataset, a large collection of multi-source dermatoscopic images of common pigmented skin lesions," Aug. 14, 2018, Scientific Data | 5:180161, pp. 1-6.*

Sumit Majumder, "Smartphone Sensors for Health Monitoring and Diagnosis," May 9, 2019, sensors, 2019, 19,2164, pp. 4-5, 14-20.*

Andre Esteva, "Dermatologist-level classification of skin cancer with deep neural networks," Jan. 25, 2017, Nature 542, pp. 115-117.*

Tiago M de Carvalho, "Development of Smartphone Apps for Skin Cancer Risk Assessment: Progress and Promise," Nov. 7, 2019, JMIR Dermatalogy, 2019;2(1) , pp. 1-7.*

Abderrahim Bourouisa, "M-Health: Skin Disease Analysis System Using Smartphone's Camera," Jun. 24, 2013, Procedia Computer Science 19 (2013), pp. 1116-1119.*

Omar Abuzaghleh, "Noninvasive Real-Time Automated Skin Lesion Analysis System for Melanoma Early Detection and Prevention," Apr. 14, 2015, IEEE Journal of Translational Engineering in Health and Medicine ( vol. 3),2015, pp. 1-10.*

International Search Report and Written Opinion on PCT AppIn PCT/US2021/045425 dated Jan. 11, 2022.

* cited by examiner

SYSTEMS AND METHODS FOR USING ARTIFICIAL INTELLIGENCE FOR SKIN CONDITION DIAGNOSIS AND TREATMENT OPTIONS

CROSS-REFERENCES TO RELATED APPLICATIONS

This application claims the benefit of and priority to U.S. Provisional Patent Application No. 63/064,061, filed Aug. 11, 2020, the contents of which is incorporated herein by reference in its entirety.

BACKGROUND

Specialists, such as dermatologists, specialize in analyzing, diagnosing, and providing treatment for diseases of the skin. However, in certain areas there may be limited access to specialists that can provide consistent treatment to common skin ailments. Instead, individuals often only have access to a primary care physician who may not be qualified to accurately diagnose and treat various skin ailments. It is particularly critical to diagnose certain skin conditions, such as cancer, as early as possible to provide the greatest probability of positive treatment outcomes.

SUMMARY

It would be advantageous for a system to automatically analyze, detect, and diagnose issues or diseases of the skin without the immediate need for a specialist.

The systems and methods of this technical disclosure provide an artificial-intelligence (AI) based solution to analyze, diagnose, and provide treatment plans for various skin conditions. This technical solution can provide a cloud-based service for the analysis of skin images of a user or patient to determine the color, characteristics, and other information about the skin of the user. This technical solution can access or retrieve the medical records or other user records through encrypted and secure channels, and use this information to provide more accurate analysis, diagnoses, and individualized treatment plans.

At least one aspect of this technical solution is directed to determining a skin color classification for a user. Other implementations rely on manual processes (e.g., human analysis and classification) to determine the skin color or tone of a user. This technical solution utilizes specially trained artificial intelligence models to accurately and automatically determine the skin color of a user. A user can provide images of healthy regions of their skin, for example by taking pictures using a camera of a smartphone. The user can also provide additional information, in the form of medical records, biometric information, or other information relating the color or tone of the skin of the user. This information can be collected by an application executing on a computing device of the user. Using the images and provided information, this technical solution can utilize a trained skin color classification model to output a value, such as a Fitzpatrick skin score, that is representative of the skin color of the user. The technical solution can subsequently store the skin score with the information provided by the user, and provide the skin score to one or more computing devices associated with healthcare professionals or a computing device (e.g., the computing device) of the user.

At least one other aspect of this technical solution is directed to analyzing images of diseased skin and automatically determining an appropriate diagnosis. Using a mobile device or other computing device, a user can provide one or more images of a portion of skin that may be diseased. The user may also provide additional information related to medical history, biometric information, or information about the portion of skin that is to be analyzed (e.g., levels of pain, etc.). This information can be provided, for example, via a computing device such as a smartphone equipped with a camera. This technical solution can receive the user-provided images and information, and access one or more medical records of the user to gather additional information to make an accurate diagnosis. Other skin characteristics, such as a skin color value or classification (e.g., Fitzpatrick skin score, etc.) may be used for the identification and diagnosis of one or more skin diseases. This technical solution can provide the information received from the user and the medical records as an input to skin characteristics classification model, which can provide one or more skin characteristic probability values as an output. The technical solution can subsequently select one or more skin characteristics associated with the probability values (e.g., when one or more of the probability values satisfy or exceed a threshold, etc.). Upon selecting the one or more skin characteristics, the technical solution can store the skin characteristics with data records of the user and provide the characteristics to a computing device of a healthcare professional or the computing device of the user (e.g., a computing device of the user, etc.).

At least one other aspect of this technical solution is directed to analyzing images of diseased skin to automatically determine and update a treatment plan for the skin issue. Other implementations rely on trained specialists to manually identify and select appropriate treatment plans for each user. This technical solution offers at least one improvement by automatically determining an individualized treatment plan that is specific to the user. Because each user may have different treatment needs (e.g., allergies, treatment resistance, pre-existing conditions, etc.), selecting specialized treatment plans that have greatest possibility of success is important to improve that chance of a positive treatment outcome. The technical solution can receive one or more images of diseased skin from a user (e.g., from an application executing on a computing device, etc.). Using the image, biometric information and user information provided by the user, and information gathered from medical records of the user, this technical solution can automatically determine and select an appropriate treatment plan for the diseased portion of skin presented in the image. Further, during the course of treatment, subsequent images can be provided by the user, and the technical solution can automatically analyze the progress of the treatment plan. If the technical solution determines that the treatment plan should be changed based on this progress, it may do so by selecting a new treatment plan or altering the previous treatment plan. The treatment plans, along with the user provided information, can be stored in association with the medical records of the user, or provided directly to a healthcare professional or a computing device of the user.

At least one other aspect of the present disclosure is directed to a method for determining a numerical classification of human skin color. The method can be performed, for example, by a data processing system comprising one or more processors and a memory. The method can include receiving an image captured by a camera, the image depicting a portion of skin of a user having a skin color. The method can include accessing biometric information of the user from a computing device of the user. The method can include determining a classification of the skin color of the user using the image and the biometric information by providing the image and the biometric information as input to a skin color classifier. The method can include providing the classification of the skin color of the user to the computing device.

In some implementations, receiving the image can include receiving a request for a skin color classification. In some implementations, receiving the image can include storing the classification of the skin color in association with the biometric information received from the computing device of the user. In some implementations, the camera is one of a smart phone, an external camera, a webcam, part of the computing device, or an external device coupled to the data processing system via a network. In some implementations, the method can include updating a model used by the skin color classifier to analyze the image based on the biometric information retrieved from the computing device and an actual classification of the skin color of the user received from the computing device.

In some implementations, the method can include providing an application to the computing device of the user. In some implementations, the image and the biometric information are received from the application executing on the computing device of the user. In some implementations, receiving the biometric information from the computing device of the user can include presenting, via the application executing on the computing device of the user, a graphical user interface (GUI) providing a first biometric information of a plurality of biometric information categories. In some implementations, receiving the biometric information from the computing device of the user can include receiving, responsive to input from the user, the biometric information as a first selection of the first biometric information from the GUI.

In some implementations, determining the classification of the skin color of the user can include receiving, from an output of the skin color classifier, a plurality of skin color classification output values. In some implementations, determining the classification of the skin color of the user can include selecting the classification of the skin color from the plurality of skin color classification output values having a value greater than another of the plurality of skin color classification output values. In some implementations, determining the classification of the skin color can include encoding the biometric information such that the biometric information can be provided as input to the skin color classifier. In some implementations, determining the classification of the skin color can include formatting the image prior to providing the image as input to the skin color classifier. In some implementations, formatting the image can include adjusting one or more colors of the image according to a reference color.

At least one other aspect of the present disclosure is directed to a system for determining a numerical classification of human skin color. The system can include a data processing system comprising one or more processors and a memory. The system can receive an image captured by a camera, the image depicting a portion of skin of a user having a skin color. The system can access biometric information of the user from a computing device of the user. The system can determine a classification of the skin color of the user using the image and the biometric information by providing the image and the biometric information as input to a skin color classifier. The system can provide the classification of the skin color of the user to the computing device.

In some implementations, the system can receive a request for a skin color classification. In some implementations, the system can store the classification of the skin color in association with the biometric information received from the computing device of the user. In some implementations, the camera is one of a smart phone, an external camera, a webcam, part of the computing device, or an external device coupled to the data processing system via a network. In some implementations, the system can update a model used by the skin color classifier to analyze the image based on the biometric information retrieved from the computing device and an actual classification of the skin color of the user received from the computing device.

In some implementations, the system can provide an application to the computing device of the user. In some implementations, the image and the biometric information are received from the application executing on the computing device of the user. In some implementations, to receive the biometric information from the computing device of the user, the system can present, via the application executing on the computing device of the user, a graphical user interface (GUI) providing a first biometric information of a plurality of biometric information categories. In some implementations, the system can receive, responsive to input from the user, the biometric information as a first selection of the first biometric information from the GUI.

In some implementations, to determine the classification of the skin color of the user, the system can receive, from an output of the skin color classifier, a plurality of skin color classification output values. In some implementations, to determine the classification of the skin color of the user, the system can select the classification of the skin color from the plurality of skin color classification output values having a value greater than another of the plurality of skin color classification output values. In some implementations, the system can encode the biometric information such that the biometric information can be provided as input to the skin color classifier. In some implementations, the system can format the image prior to providing the image as input to the skin color classifier. In some implementations, the system can adjust one or more colors of the image according to a reference color.

At least one other aspect of the present disclosure is directed to a method of identifying one or more characteristics of skin. The method can be performed, for example, by a data processing system comprising one or more processors coupled to memory. The method can include receiving an image captured by a camera, the image depicting a portion of skin of a user. The method can include determining, based on the image, a plurality of probability scores that each correspond to a respective one of a plurality of skin characteristics. The method can include selecting a skin characteristic of the plurality of skin characteristics based on the plurality of probability scores. The method can include providing the skin characteristic to a computing device of the user.

In some implementations, providing the skin characteristic can include storing the skin characteristic in a medical data record associated with the user. In some implementations, the method can include identifying, based on the image and the skin characteristic, a treatment option to treat a skin disease corresponding to the skin characteristic. In some implementations, the method can include transmitting the treatment option to the computing device of the user. In some implementations, the method can include accessing, from a medical database, a medical record associated with the user. In some implementations, the method can include determining the plurality of probability scores further based on the medical record.

In some implementations, the method can include receiving a second image of the portion of skin at a later time. In some implementations, the method can include determining second skin characteristics using the second image. In some implementations, the method can include comparing the second skin characteristics with the skin characteristic to determine a change in characteristics of the portion of skin. In some implementations, the method can include presenting a graphical user interface (GUI) providing at least one question about the portion of skin represented by the image. In some implementations, the method can include receiving an answer to the at least one question presented in the GUI. In some implementations, the method can include determining, based on the image, the plurality of probability scores further based on at least the answer to the at least one question presented in the GUI.

In some implementations, presenting the graphical user interface (GUI) can include transmitting an application to a computing device of the user. In some implementations, the method can include receiving the answer to the at least one question from an input to the application executing on the computing device of the user. In some implementations, the plurality of skin characteristics comprises a diagnosis of one or more skin conditions. In some implementations, selecting the skin characteristic of the plurality of skin characteristics can include determining a diagnosis of a skin condition depicted in the image. In some implementations, determining the diagnosis of the skin condition depicted in the image can include determining a severity of the skin condition depicted in the image.

At least one other aspect of the present disclosure is directed to a system for identifying one or more characteristics of skin. The system can include a data processing system comprising one or more processors and a memory. The system can receive an image captured by a camera, the image depicting a portion of skin of a user. The system can determine, based on the image, a plurality of probability scores that each correspond to a respective one of a plurality of skin characteristics. The system can select a skin characteristic of the plurality of skin characteristics based on the plurality of probability scores. The system can provide the skin characteristic to a computing device of the user.

In some implementations, to provide the skin characteristic, the system can store the skin characteristic in a medical data record associated with the user. In some implementations, the system can identify, based on the image and the skin characteristic, a treatment option to treat a skin disease corresponding to the skin characteristic. In some implementations, the system can transmit the treatment option to the computing device of the user. In some implementations, the system can access, from a medical database, a medical record associated with the user. In some implementations, the system can determine the plurality of probability scores further based on the medical record.

In some implementations, the system can receive a second image of the portion of skin at a later time. In some implementations, the system can determine second skin characteristics using the second image. In some implementations, the system can compare the second skin characteristics with the skin characteristic to determine a change in characteristics of the portion of skin. In some implementations, the system can present a graphical user interface (GUI) providing at least one question about the portion of skin represented by the image. In some implementations, the system can receive an answer to the at least one question presented in the GUI. In some implementations, the system can determine the plurality of probability scores further based on at least the answer to the at least one question presented in the GUI.

In some implementations, the system can present the graphical user interface (GUI) by transmitting an application to a computing device of the user. In some implementations, the system can receive the answer via an input to the application executing on the computing device of the user. In some implementations, the plurality of skin characteristics comprises a diagnosis of one or more skin conditions. In some implementations, the system can determine a diagnosis of a skin condition depicted in the image. In some implementations, the system can determine a severity of the skin condition depicted in the image.

At least one other aspect of the present disclosure is directed to a method of analyzing skin images to determine a personalized treatment plan. The method can be performed, for example, by a data processing system comprising one or more processors coupled to memory. The method can include receiving an image captured by a camera, the image depicting a diseased portion of skin of a user. The method can include accessing a medical record associated with the user to identify a skin characteristics of the diseased portion of skin represented in the image. The method can include determining a plurality of treatment plans for the diseased portion of skin based on the skin characteristics and the image. The method can include selecting a first treatment plan of the plurality of treatment plans based on the medical record. The method can include providing the first treatment plan to a computing device of the user.

In some implementations, accessing the medical record can include receiving, from a medical database, a set of treatment preferences. In some implementations, selecting the first treatment plan is further based on the set of treatment preferences. In some implementations, providing the first treatment plan further comprises storing, in a medical database, the first treatment plan in association with the medical record of the user. In some implementations, accessing the medical record associated with the user further comprises receiving a skin diagnosis from the medical record. In some implementations, determining the plurality of treatment plans is further based on at least the skin diagnosis.

In some implementations, selecting the first treatment plan is further based on at least one of: a frequency of prescription of the first treatment plan, outcome data for the first treatment plan, or a historical diagnosis of the user. In some implementations, the method can include receiving a second image of the diseased portion of skin of the user. In some implementations, the method can include determining a treatment progress of the diseased portion of skin of the user based on the image and the second image. In some implementations, the method can include selecting a second treatment of the plurality of treatment plans based on the medical record and the treatment progress.

In some implementations, determining the treatment progress of the diseased portion of skin of the user can include determining a change in characteristics of the diseased portion of skin between the image and the second image. In some implementations, the method can include transmitting the treatment progress of the diseased portion of skin to the computing device of the user. In some implementations, the method can include storing the treatment progress of the diseased portion of skin in the medical record of the user. In some implementations, the method can include providing an application to the computing device that, when executed, presents a graphical user interface to the user on the computing device. In some implementations, providing the first treatment plan to the computing device of the user further comprises transmitting the first treatment plan to the application executing on the computing device.

At least one other aspect of the present disclosure is directed to a system for analyzing skin images to determine a personalized treatment plan. The system can include a data processing system comprising one or more processors and a memory. The system can receive an image captured by a camera, the image depicting a diseased portion of skin of a user. The system can access a medical record associated with the user to identify a skin characteristics of the diseased portion of skin represented in the image. The system can determine a plurality of treatment plans for the diseased portion of skin based on the skin characteristics and the image. The system can select a first treatment plan of the plurality of treatment plans based on the medical record. The system can provide the first treatment plan to a computing device of the user.

In some implementations, to access the medical record, the system can receive, from a medical database, a set of treatment preferences. In some implementations, select the first treatment plan further based on the set of treatment preferences. In some implementations, to provide the first treatment plan, the system can store, in a medical database, the first treatment plan in association with the medical record of the user. In some implementations, the system can receive a skin diagnosis from the medical record. In some implementations, the system can determine the plurality of treatment plans further based on at least the skin diagnosis. In some implementations, the system can select the first treatment plan further based on at least one of: a frequency of prescription of the first treatment plan, outcome data for the first treatment plan, or a historical diagnosis of the user.

In some implementations, the system can receive a second image of the diseased portion of skin of the user. In some implementations, the system can determine a treatment progress of the diseased portion of skin of the user based on the image and the second image. In some implementations, the system can select a second treatment of the plurality of treatment plans based on the medical record and the treatment progress. In some implementations, to determine the treatment progress of the diseased portion of skin of the user, the system can determine a change in characteristics of the diseased portion of skin between the image and the second image. In some implementations, the system can transmit the treatment progress of the diseased portion of skin to the computing device of the user. In some implementations, the system can store the treatment progress of the diseased portion of skin in the medical record of the user. In some implementations, the system can provide an application to the computing device that, when executed, presents a graphical user interface to the user on the computing device. In some implementations, the system can transmit the first treatment plan to the application executing on the computing device.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form. For example, by appropriate computer programs, which may be carried on appropriate carrier media (computer readable media), which may be tangible carrier media (e.g. disks) or intangible carrier media (e.g. communications signals). Aspects may also be implemented using suitable apparatus, which may take the form of programmable computers running computer programs arranged to implement the aspect. As used in the specification and in the claims, the singular form of 'a', 'an', and 'the' include plural referents unless the context clearly dictates otherwise.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 8A, 8B, 8C, 8D, 8E, 8F, 8G, 8H, 8I, 8J, 8K, 8L, 8M, 8N, 8O, 8P, 8Q, 8R, and 8S each depict various graphical user interfaces displayed by an application executing on a mobile device that provide one or more of the functionalities described herein.

DETAILED DESCRIPTION

Figure 1A:
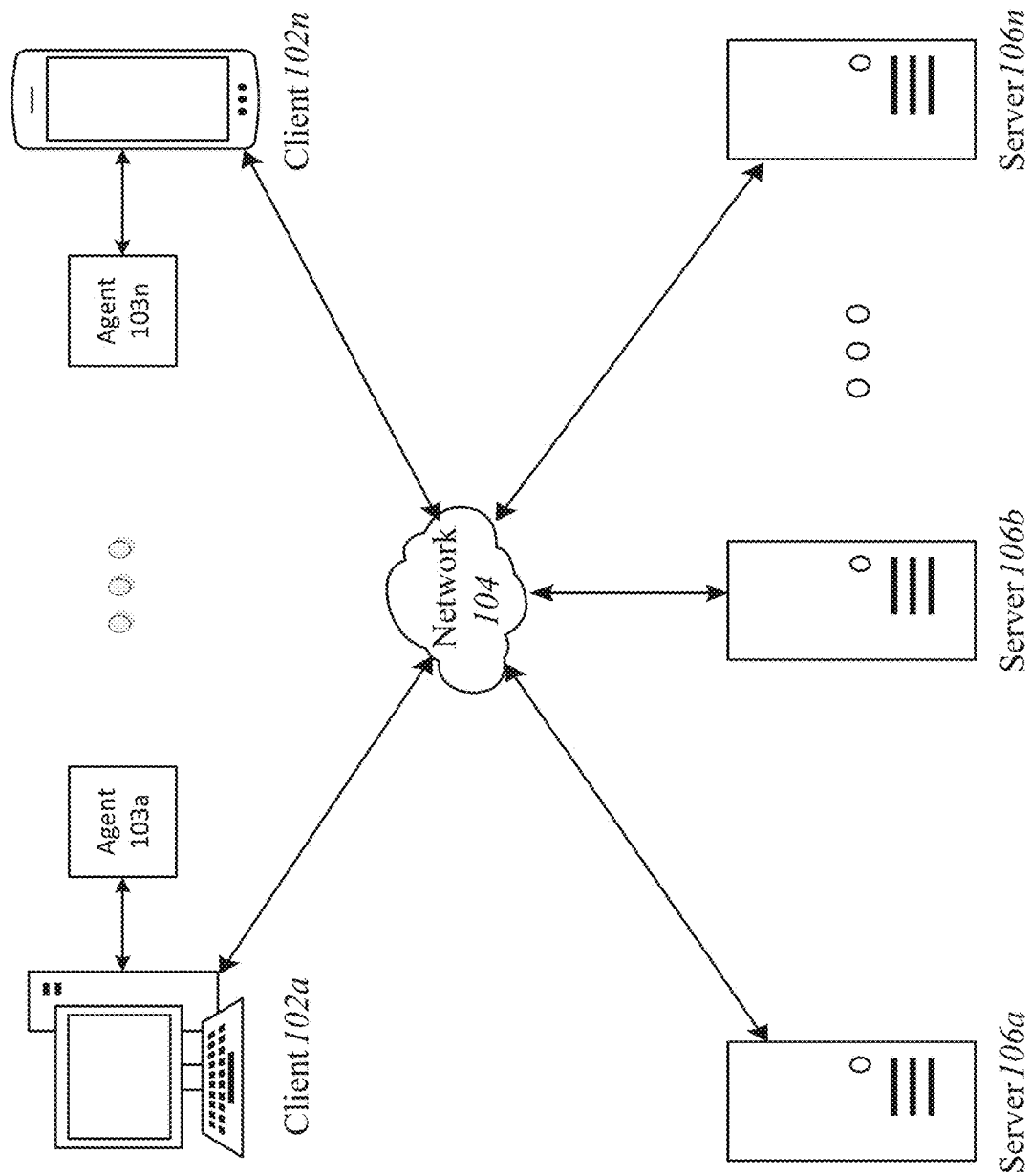
FIG. 1A is a block diagram depicting an embodiment of a network environment comprising a client device in communication with a server device.

Below are detailed descriptions of various concepts related to, and implementations of, techniques, approaches, methods, apparatuses, and systems for determining a numerical classification of human skin color, determining one or more characteristics of human skin, and analyzing skin images to determine a personalized treatment plan. The various concepts introduced above and discussed in greater detail below may be implemented in any of numerous ways, as the described concepts are not limited to any particular manner of implementation. Examples of specific implementations and applications are provided primarily for illustrative purposes.

At least one aspect of this technical solution provides at least one implementation for identifying a numerical value that describes the skin color of a user from one or more images provided by the user. To aid in the classification process, the user may provide additional information, either in the form of answers to questions or any other type of information that would aid in the classification of skin color or other skin characteristics. The determined skin characteristic score can be, for example, a Fitzpatrick skin score (e.g., on a scale from one to six, etc.), or any other type of numerical identification. Certain biometric information such as eye color and natural hair color may be used to by the systems and methods described in this technical solution to aid in the classification or identification of certain skin characteristics. The systems and methods described herein may utilize reference colors in the image. For example, the system may prompt the user to provide one or more images of the user's skin with a normal (e.g., new, crisp, unworn, etc.) United States dollar bill in the image to act as a color reference. Because United States currency has a standard color, the system can identify the currency and use it as a reference color when classifying or identifying the characteristics of the user's skin. The systems and methods described herein can provide the classifications or determination of the numerical skin score to the mobile device of the user, and store the skin score in association with one or more medical records of the user.

Further describing the aspect introduced above, the systems and methods described herein can be utilized to automatically and consistently identify the skin tone of a user. The identified skin tone can be, for example, one of six skin tones, where a '1' of on the scale refers to a skin tone that does not tan in the sun and usually always burns, and a '6' on the scale refers to very dark skin that always tans and rarely if never burns. Such a skin tone can be, for example, a Fitzpatrick skin score. Typically, the identification of skin tone or skin score is performed by a specialist using manual processes. In addition to identifying the skin score, the systems and methods described herein may also identify and provide the skin color of the user. The automatic classification and identification of skin information can be critical to the skin diagnostic process, and is therefore important to the fields of dermatology. Further, the systems and methods of this technical solution may also be used in the field of cosmetology, for example in the identification of certain makeup, skin care products, matching clothing lines, and other cosmetic determinations based on the skin color or tone of the user.

The systems and methods of this technical solution can be executed remotely, for example from a cloud environment such as the cloud environment described herein below in conjunction with FIGS. 1A-1D. Instead of relying on manual processes from a specialist, the systems and methods of this technical solution can utilize machine learning models and other artificial intelligence constructs to identify, classify, or determine the skin tone score or skin color of skin in one or more images provided by the user. The determination of the skin tone of the user may be used in other aspects of this technical solution described in greater detail below, such as the diagnosis of one or more diseases of the skin, the determination of one or more skin characteristics, the determination of one or more personalized skin treatment plans for the user, and the determining the change in a skin condition as the treatment plan is applied to the diagnosed skin condition over time. However, it should be understood that the determination of the skin tone, skin color, or skin score of a user is not limited to just those uses.

For example, in addition to aiding in the diagnosis of various skin diseases or conditions, the skin tone of a user may be used in the selection of appropriate makeup tones, or the selection of appropriately styled clothing that is commensurate with the user's skin tone. Accordingly, the skin tone determined by the systems and methods of this technical solution can be used for any industry that utilizes the skin tone of the user, such as the fashion industry or the cosmetology industry. Typically, the identification of a user's skin tone is performed by manual processes that involves a human providing the skin tone value or score as an input to whatever system requires the skin tone value. The automatic determination of skin tone values can be performed by using one or more images provided by the user as an input to a skin tone determination module. The skin tone determination module may be implemented, for example, using a neural network such as a fully connected neural network, a recurrent neural network, or another type of trained machine learning model. Additional information about the user, such as answers to various questions about the user's skin, biometric information, or medical treatment information, may also be provided as an input in the skin tone determination module. The images of the skin of the user may be captured, for example, using a smart phone camera or a camera coupled to another computing device.

For example, the user may download an application that can communicate with one or more of the computing systems described herein to the user's smartphone. The user may provide personal or clinically relevant information (e.g., biometric information, medical information, any other information described herein, etc.) that can be transmitted to and stored in an encrypted and secure database. The secure database may operate in one or more cloud computing environments, such as the cloud computing environment described herein below in conjunction with FIGS. 1A-1D. Upon receiving the user information and the images, the systems of this technical solution can provide the information and the images as input to a skin color classification module to determine a skin color score. The skin color score can be stored, along with the information provided by the user, in one or more user records maintained in an encrypted database. The skin color score may be returned to the application for display, or it may be utilized by another of the aspects of this technical solution.

At least one other aspect of this technical solution is directed to the automatic determination of skin issues, diagnoses, or conditions based on user provided images of potentially diseased portions of skin. Typically, the diagnosis process is performed based on user information provided to a skin specialist or other skin professional. The systems and methods of this technical solution can automate this process by analyzing and inputting user information such as medical history, biometric information, skin tone score information, and other information into a skin disease model. The systems and methods of this technical solution can operate in a cloud environment, such as the cloud environment described in detail below in conjunction with FIGS. 1A-1D. Accordingly, the systems and methods of this technical solution can provide an adequate skin exam to the user which will decrease the overall need for referrals to the dermatologist and improve the consistency and accuracy of the identification or determination of skin ailments, conditions, or characteristics. The systems and methods of this technical solution can provide a mobile application or web-based application that can be executed on a mobile device of a user. The mobile application may also provide access to a telemedicine platform, which can allow the user to contact a specialist if needed.

The application can receive one or more images, for example from the camera of a smart phone, a standalone camera, or a web camera (sometimes referred to as a webcam). The user may also be presented with one or more questions from a set of questions. The questions, for example, can be related to any type of medical history of the user, such as history of skin conditions, treatment history, family history of skin conditions or other medical conditions. The questions may also be directed to the potential skin disease that is to be analyzed, such as questions relating to itching, pain, burning, or other questions relating to symptoms the user has experienced.

The questions may include, but are not limited to, variations of: "What is the duration of the skin condition?", "Have you had any prior treatments?", "Do you have a prior history of skin conditions", "Do you use drugs?", "Do you have a systematic illness?", "Do you have a family history of skin diseases?", "Is the lesion painful or painless?", "Does the lesion itch?", "Is there a burning sensation?", among others. The user can provide one or more answers to the questions via the application executing on a computing device (e.g., mobile device, other computing device described herein) of the user. For example, for each question, the application may provide the user with various interactive objects, such as check boxes, radio bubbles, text boxes, or other labelled interactive objects with which to answer each question. After providing answers to the questions, and after entering any other clinically relevant information, the application may prompt the user to capture one or more images of the skin tissue that is to be analyzed (e.g., an area of skin of the user that is of concern, etc.). The images and the information provided by the user can then be uploaded by the application to a secure and encrypted database.

Providing the images can cause the systems and methods of this technical solution to combine the image data and with other relevant information associated with the user, such as the skin score (e.g., numerical quantification of skin color, Fitzpatrick skin score, etc.), information present in the medical records of the user, and the answers to the questions and any other information provided by the user via the application. The systems and methods of this technical solution may provide this information as an input to a skin characteristic determination module, which can assign a probability score to one or more possible skin diseases based on the input data. Based on certain selection criteria, the systems and methods of this technical solution can select at least one of the one or more possible skin diseases and store the selected skin disease in the patient record. The output of this process may also be provided to one or more healthcare professionals, or to the application executing on the computing device of the user. The classification of the skin characteristics (e.g., diagnosis of skin disease, etc.) may be utilized in other aspects of this technical solution as described herein below.

At least one other aspect of this technical solution is the determination of individualized treatment plans for diagnosed skin issues or conditions. The treatment plans can be individualized and based on a user's medical history data, treatment progress, and historical data that indicates the success or failure of various treatment options for similar skin conditions. The systems and methods of this technical solution may be used to provide a precise treatment option for an individual's skin condition. This technical solution can utilize one or more AI based classifiers, such as neural networks, to determine a precise treatment plan based on image input and other numerically encoded data. In addition, this technical solution can monitor the progress of a particular treatment plan over time, and make automatic adjustments based on the efficacy of the plan. Accordingly, this technical solution can determine the severity of a diagnosed or detected skin condition or characteristic, and examine various data points of the user to determine a precise and personalized treatment plan for that user. Accordingly, this technical solution can improve the efficiency, accuracy, and effectiveness of dermatological treatment using artificial intelligence.

The user can utilize a mobile application or web application to upload one or more images of an area of skin that may have a skin condition or issue. This technical solution can receive the images and other user information, such as medical records, and other user data such as answers to questions, and provide a precise and personalized treatment plan. The treatment plan can be stored in association with one or more patient records, or provided to a healthcare professional (e.g., for a prescription, etc.). Over the course of the treatment, the user can submit additional images of the skin under treatment, and the system can modify the treatment plan as needed (e.g., change to a different treatment if the first treatment does not work, adjust if an adverse reaction to a prescription or drug, etc.). Typically, the creation of treatment plans for skin conditions are performed via manual processes and by a specialist. However, manual processes are prone to error, subjective, inconsistent, and are often entirely unavailable in certain areas. This technical solution provides an efficient, accurate, objective, consistent, and personalized treatment plan based on user medical data. The systems and methods of this technical solution can provide a mobile application or web-based application that can be executed on a mobile device of a user. The mobile application may also provide access to a telemedicine platform, which can allow the user to contact a specialist if needed.

The application can receive one or more images, for example from the camera of a smart phone, a standalone camera, or a web camera (sometimes referred to as a webcam). The user may also be presented with one or more questions from a set of questions. The questions, for example, can be related to any type of medical history of the user, such as history of skin conditions, treatment history, family history of skin conditions or other medical conditions. The questions may also be directed to the potential skin disease that is to be analyzed, such as questions relating to itching, pain, burning, or other questions relating to symptoms the user has experienced.

The questions may include, but are not limited to, variations of: "What is the duration of the skin condition?", "Have you had any prior treatments?", "Do you have a prior history of skin conditions", "Do you use drugs?", "Do you have a systematic illness?", "Do you have a family history of skin diseases?", "Is the lesion painful or painless?", "Does the lesion itch?", "Is there a burning sensation?", among others. The user can provide one or more answers to the questions via the application executing on a computing device (e.g., mobile device, other computing device described herein) of the user. For example, for each question, the application may provide the user with various interactive objects, such as check boxes, radio bubbles, text boxes, or other labelled interactive objects with which to answer each question. After providing answers to the questions, and after entering any other clinically relevant information, the application may prompt the user to capture one or more images of the skin tissue that is to be analyzed (e.g., an area of skin of the user that is of concern, etc.). The images and the information provided by the user can then be uploaded by the application to a secure and encrypted database.

This technical solution can create a user case or user record entry in the secure medical database, and can allocate a new region of memory for the particular diagnosis in question. The data from the images, the user's medical records, the user's answers to the questions, and other relevant user information can be provided as input to a treatment plan determination module. The treatment plan determination module (e.g., as implemented by the components of the skin analysis system 120), can output one or more potential treatment plans for the user based on the input data. This technical solution can also interrogate a database consisting of current best practices and historical outcomes for a given skin pathology to aid in the selection of a determined personalized treatment plan for the user. In this way, the treatment options are always the most accurate and most likely to provide for a positive treatment outcome. This technical solution can then subsequently select one or more treatment plans that are best suited for the user based on the medical history of the user, the diagnosis of the skin condition, and the current best practices. The selected personalized treatment plan can be provided to the user for display in the application, or provided to a healthcare professional, or stored in association with the medial records of the user.

This technical solution can provide a dermatology treatment plan decision support system (e.g., the skin analysis system 120, etc.) consisting of a set of interacting modules (e.g., components, etc.) This technical solution can provide a neural network-based classifier. The input layer of the classifier can include numerically coded case-specific information, such as medical diagnoses, confidence values for these diagnoses, and other clinically relevant data for the case including patient past medical history. The output layer of the classifier can include one or more coded treatment options. Other modules or components can be dynamically queried if needed by the system to select among these treatment options. For example, given a plurality of acceptable treatment options, a doctor preference (or clinic preference) module might be consulted to select a particular treatment from this set. (For instance, some clinicians prefer non-generic drugs to be prescribed). In some implementations, the classifier can include support vector machine (SVM) models, neural networks, and hidden Markov models, among others. In some implementations, this technical solution can utilize natural language processing to extract a particular treatment given a pathology, and to understand the degree of success or failure of that treatment, from published academic articles. Many articles in peer-reviewed journals are amenable to this type of free-text analysis. By using such natural-language processing techniques and accumulating its results to an ongoing set of training data, the system can improve the relevancy and accuracy of the classifications.

Prior to discussing specific implementations of the present solution, it may be helpful to describe aspects of the operating environment as well as associated system components (e.g., hardware elements) in connection with the methods and systems described herein. Referring to FIG. 1A, an implementation of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more agents 103a-103n and one or more servers 106a-106n (also generally referred to as server(s) 106, node 106, or remote machine(s) 106) via one or more networks 104. In some implementations, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some implementations, there are multiple networks 104 between the clients 102 and the servers 106. In one of these implementations, a network 104' (not shown) may be a private network and a network 104 may be a public network. In another of these implementations, a network 104 may be a private network and a network 104' a public network. In still another of these implementations, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some implementations, different types of data may be transmitted via different links and standards. In other implementations, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some implementations, the system may include multiple, logically-grouped servers 106. In one of these implementations, the logical group of servers may be referred to as a server farm 38 (not shown) or a machine farm 38. In another of these implementations, the servers 106 may be geographically dispersed. In other implementations, a machine farm 38 may be administered as a single entity. In still other implementations, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Washington), while one or more of the other servers 106 can operate on according to another type of operating system platform (e.g., Unix, Linux, or Mac OS X).

In one implementation, servers 106 in the machine farm 38 may be stored in high-density rack systems, along with associated storage systems, and located in an enterprise data center. In this implementation, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these implementations, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these implementations, one or more servers 106 provide functionality for management of dynamic data, including techniques for handling failover, data replication, and increasing the robustness of the machine farm 38. Each server 106 may communicate with a persistent store and, in some implementations, with a dynamic store.

Server 106 may be a file server, application server, web server, proxy server, appliance, network appliance, gateway, gateway server, virtualization server, deployment server, SSL VPN server, or firewall. In one implementation, the server 106 may be referred to as a remote machine or a node. In another implementation, a plurality of nodes 290 may be in the path between any two communicating servers.

Figure 1B:
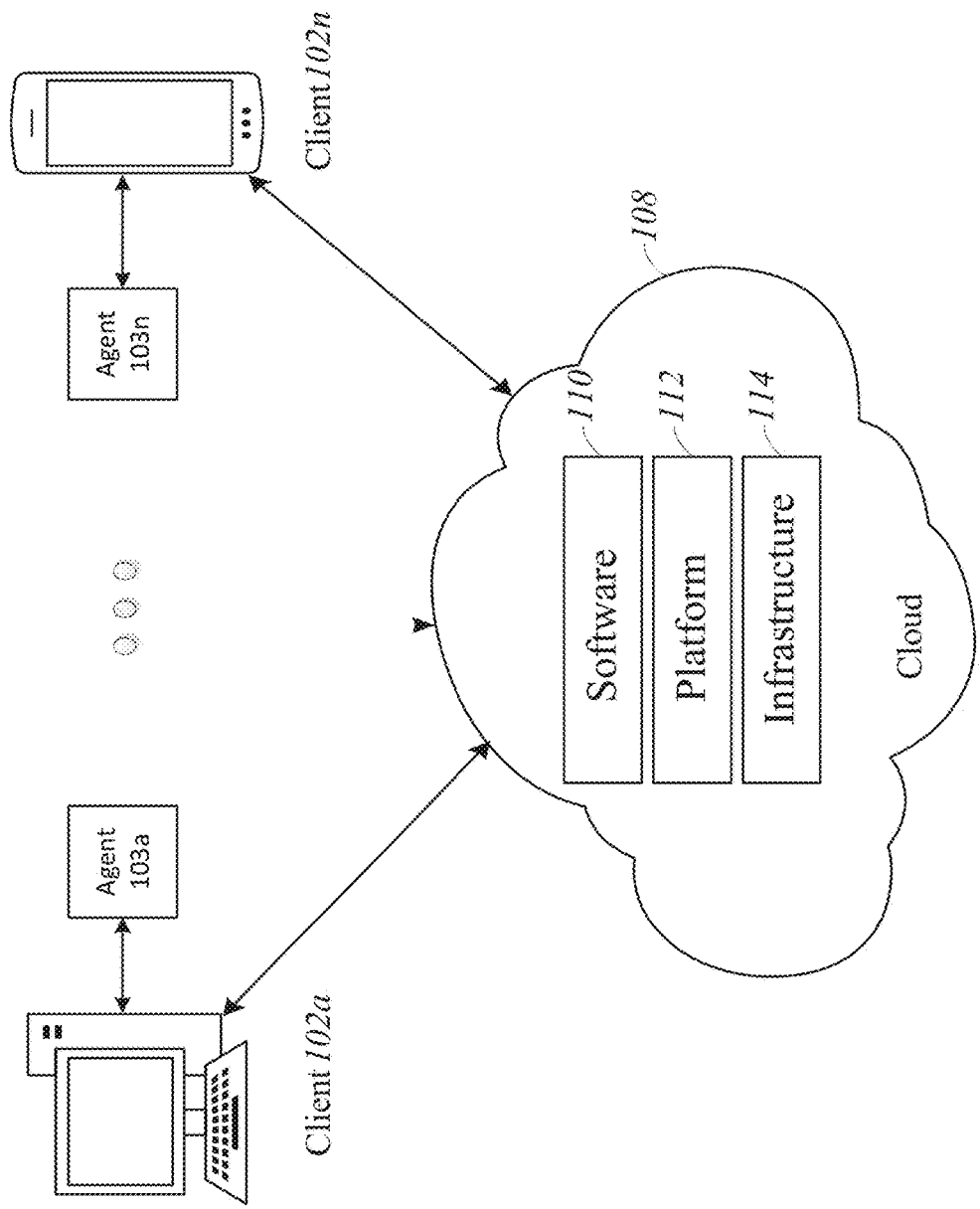
FIG. 1B is a block diagram depicting a cloud computing environment comprising a client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with respective agents 103a-103n and with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California SaaS providers may offer the resources that PaaS provides, including storage, networking, servers, virtualization, operating system, middleware, or runtime resources. In some implementations, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some implementations, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
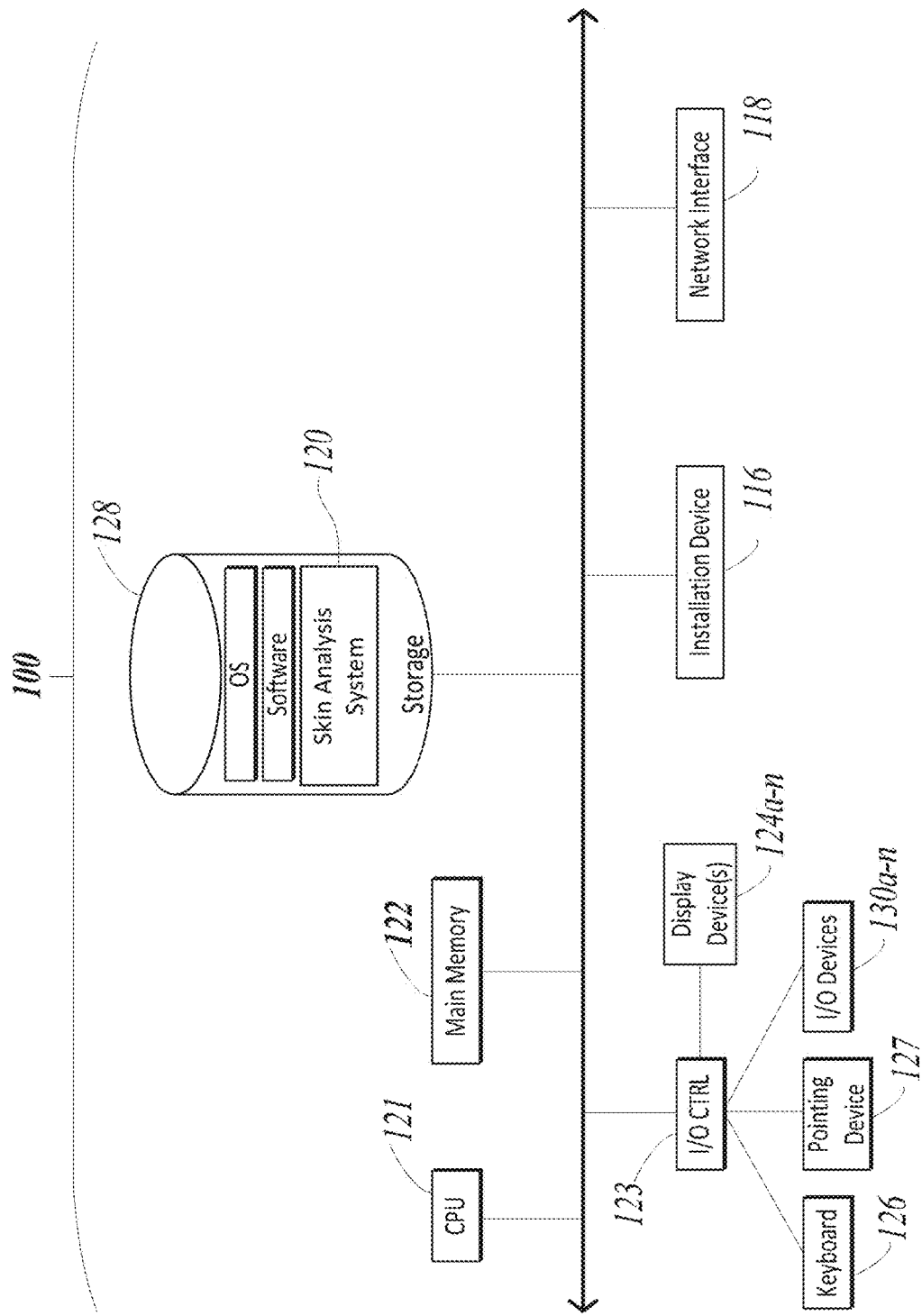
FIGS. 1C and 1D are block diagrams depicting embodiments of computing devices useful in connection with the methods and systems described herein.
Figure 1D:
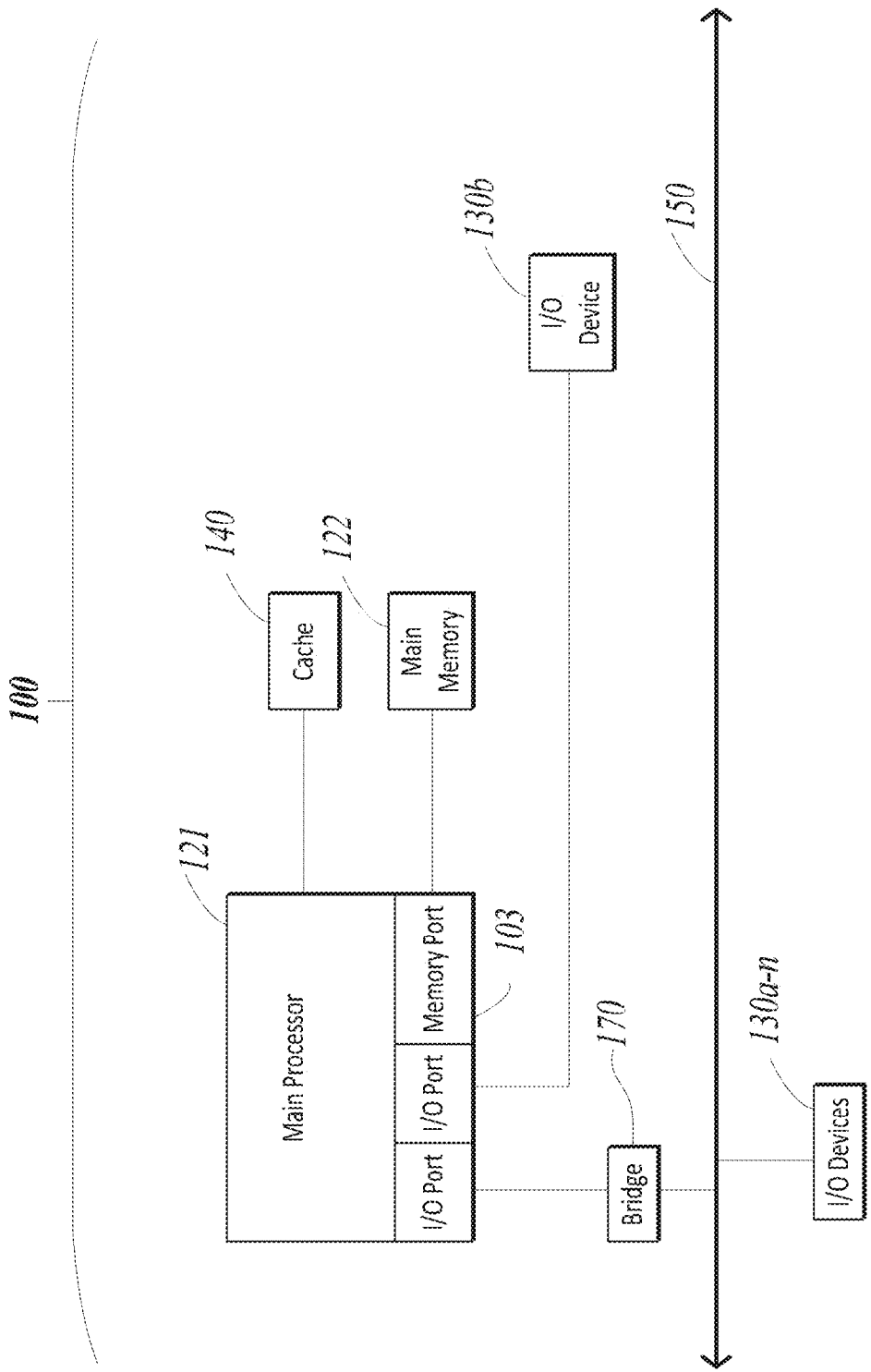

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an implementation of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a skin analysis system 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many implementations, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some implementations, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the implementation shown in FIG. 1C, the processor 121 communicates with main memory 122 via a system bus 150 (described in more detail below). FIG. 1D depicts an implementation of a computing device 100 in which the processor communicates directly with main memory 122 via a memory port 103. For example, in FIG. 1D the main memory 122 may be DRDRAM.

FIG. 1D depicts an implementation in which the main processor 121 communicates directly with cache memory 140 via a secondary bus, sometimes referred to as a backside bus. In other implementations, the main processor 121 communicates with cache memory 140 using the system bus 150. Cache memory 140 typically has a faster response time than main memory 122 and is typically provided by SRAM, BSRAM, or EDRAM. In the implementation shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For implementations in which the I/O device is a video display 124, the processor 121 may use an Advanced Graphics Port (AGP) to communicate with the display 124 or the I/O controller 123 for the display 124. FIG. 1D depicts an implementation of a computer 100 in which the main processor 121 communicates directly with I/O device 130*b* or other processors 121' via HYPER-TRANSPORT, RAPIDIO, or INFINIBAND communications technology. FIG. 1D also depicts an implementation in which local busses and direct communication are mixed: the processor 121 communicates with I/O device 130*a* using a local interconnect bus while communicating with I/O device 130*b* directly.

A wide variety of I/O devices 130*a*-130*n* may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130*a*-130*n* may include a combination of multiple input or output devices, including, e.g., Microsoft KINECT, Nintendo Wiimote for the WII, Nintendo WII U GAMEPAD, or Apple IPHONE. Some devices 130*a*-130*n* allow gesture recognition inputs through combining some of the inputs and outputs. Some devices 130*a*-130*n* provides for facial recognition which may be utilized as an input for different purposes including authentication and other commands. Some devices 130*a*-130*n* provides for voice recognition and inputs, including, e.g., Microsoft KINECT, SIRI for IPHONE by Apple, Google Now or Google Voice Search.

Additional devices 130*a*-130*n* have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130*a*-130*n*, display devices 124*a*-124*n* or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other implementations, the computing device 100 may provide USB connections (not shown) to receive handheld USB storage devices. In further implementations, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some implementations, display devices 124*a*-124*n* may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopic. Display devices 124*a*-124*n* may also be a head-mounted display (HMD). In some implementations, display devices 124*a*-124*n* or the corresponding I/O controllers 123 may be controlled through or have hardware support for OPENGL or DIRECTX API or other graphics libraries.

In some implementations, the computing device 100 may include or connect to multiple display devices 124*a*-124*n*, which each may be of the same or different type and/or form. As such, any of the I/O devices 130*a*-130*n* and/or the I/O controller 123 may include any type and/or form of suitable hardware, software, or combination of hardware and software to support, enable or provide for the connection and use of multiple display devices 124*a*-124*n* by the computing device 100. For example, the computing device 100 may include any type and/or form of video adapter, video card, driver, and/or library to interface, communicate, connect or otherwise use the display devices 124*a*-124*n*. In one implementation, a video adapter may include multiple connectors to interface to multiple display devices 124*a*-124*n*. In other implementations, the computing device 100 may include multiple video adapters, with each video adapter connected to one or more of the display devices 124*a*-124*n*. In some implementations, any portion of the operating system of the computing device 100 may be configured for using multiple displays 124*a*-124*n*. In other implementations, one or more of the display devices 124*a*-124*n* may be provided by one or more other computing devices 100*a* or 100*b* connected to the computing device 100, via the network 104. In some implementations software may be designed and constructed to use another computer's display device as a second display device 124*a* for the computing device 100. For example, in one implementation, an Apple iPad may connect to a computing device 100 and use the display of the device 100 as an additional display screen that may be used as an extended desktop. One ordinarily skilled in the art will recognize and appreciate the various ways and implementations that a computing device 100 may be configured to have multiple display devices 124*a*-124*n*.

Referring again to FIG. 1C, the computing device 100 may comprise a storage device 128 (e.g. one or more hard disk drives or redundant arrays of independent disks) for storing an operating system or other related software, and for storing application software programs such as any program related to the skin analysis system 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102*a*-102*n* may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one implementation, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESS-CARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some implementations, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some implementations, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some implementations, the computing device 100 is a digital audio player such as the Apple IPOD, IPOD Touch, and IPOD NANO lines of devices, manufactured by Apple Computer of Cupertino, California Some digital audio players may have other functionality, including, e.g., a gaming system or any functionality made available by an application from a digital application distribution platform. For example, the IPOD Touch may access the Apple App Store. In some implementations, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some implementations, the computing device 100 is a tablet e.g. the IPAD line of devices by Apple; GALAXY TAB family of devices by Samsung; or KINDLE FIRE, by Amazon.com, Inc. of Seattle, Washington In other implementations, the computing device 100 is an eBook reader, e.g. the KINDLE family of devices by Amazon.com, or NOOK family of devices by Barnes & Noble, Inc. of New York City, New York.

In some implementations, the communications device 102 includes a combination of devices, e.g. a smartphone combined with a digital audio player or portable media player. For example, one of these implementations is a smartphone, e.g. the IPHONE family of smartphones manufactured by Apple, Inc.; a Samsung GALAXY family of smartphones manufactured by Samsung, Inc; or a Motorola DROID family of smartphones. In yet another implementation, the communications device 102 is a laptop or desktop computer equipped with a web browser and a microphone and speaker system, e.g. a telephony headset. In these implementations, the communications devices 102 are web-enabled and can receive and initiate phone calls. In some implementations, a laptop or desktop computer is also equipped with a webcam or other video capture device that enables video chat and video call.

In some implementations, the status of one or more machines 102, 106 in the network 104 is monitored, generally as part of network management. In one of these implementations, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these implementations, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

Figure 2:
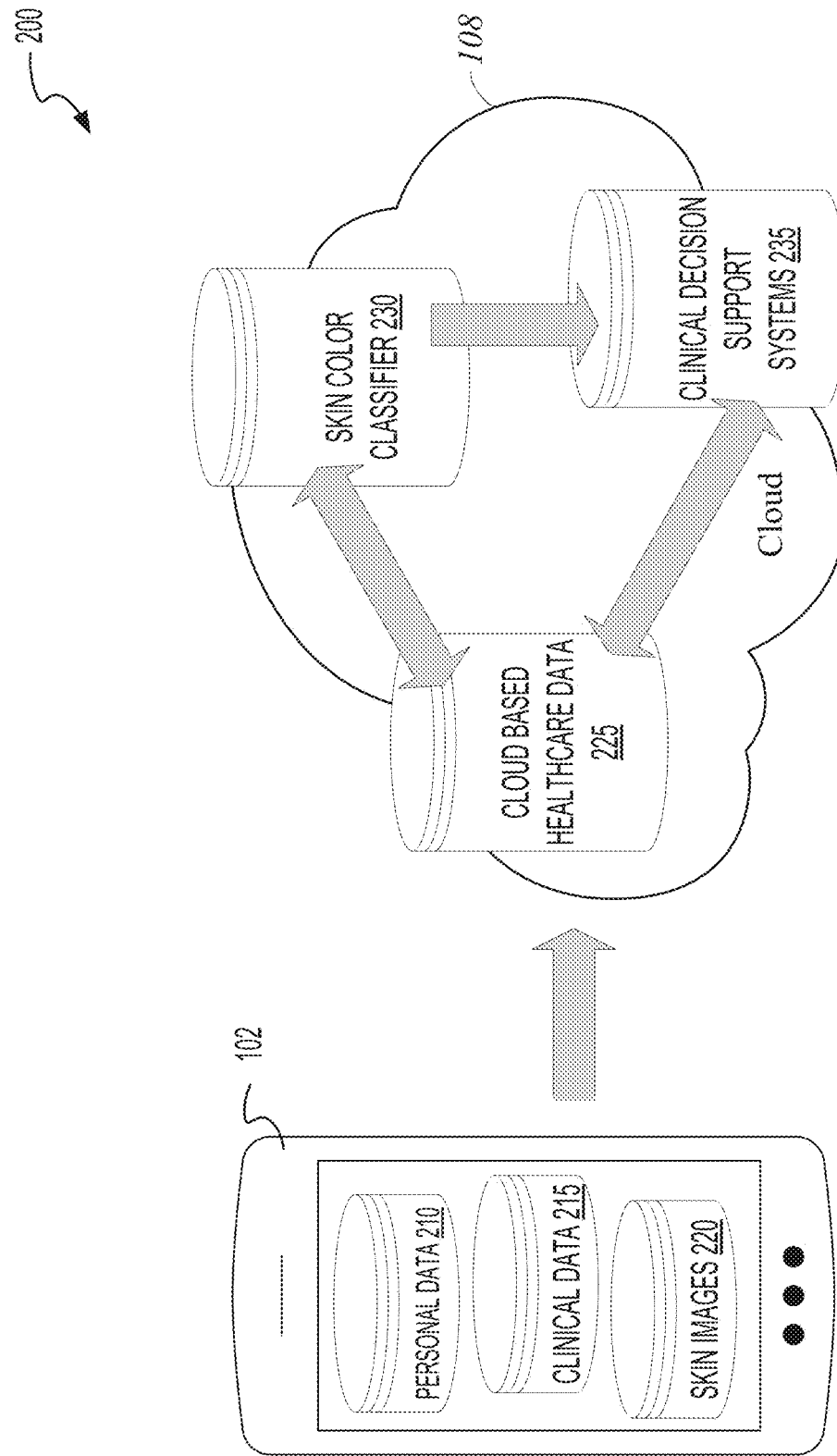
FIG. 2 illustrates a block diagram of an example system for the analysis and classification of various skin characteristics or diseases, and for the selection of user-specific treatment plans based on skin characteristics.

Referring now to FIG. 2, illustrated is a block diagram of an example system 200 for a cloud-based skin analysis, diagnosis, and treatment system. The system 200 can include at least one client device 102, as described herein above in communication with at least one cloud environment 108 described herein above. The cloud based environment can maintain, for example as a part of the skin analysis system 120, at least one cloud based healthcare data 225, at least one skin color classifier 230 and at least one clinical decision support systems 235. Although each of the cloud based healthcare data 225, the skin color classifier 230, and the clinical support systems 235 are depicted in FIG. 2 as separate computing devices, it should be understood that each of those components can be implemented by some or all of the skin analysis system 120 and the components thereof described in further detail below in conjunction with FIGS. 3A-3C.

The personal data 210 can be captured, maintained, or retrieved by the client device 102 (sometimes referred generally as mobile device 102). The mobile device 102 may present a graphical user interface on a display coupled to a processor of the mobile device. The graphical user interface may be, for example, presented in response to executing an application (e.g., the application 320 described herein below in conjunction with FIGS. 3A-3C, etc.) provided by one of the computing devices of the cloud 108, or another computing device external to the mobile device 102. The graphical user interface provided by the mobile device 102 can present questions to a user, with appropriate spaces, input boxes, or other means to provide input to the computing device. The application executing on the mobile device 102 can gather answers to the questions and store the information in one or more data structures in at least one region of the memory of the mobile device 102. For example, the questions may include, but are not limited to: "What color are your eyes?". "What is the natural color of your hair", "What color is your skin (unexposed areas)?, "Do you have freckles on unexposed areas?", or "What happens when you stay too long in the sun?", "To what degree do you turn brown?", "Do you turn brown with several hours of sun exposure?", or "How does your face react to the sun?".

In response to the questions presented to the user in the application, the user may be prompted with one or more suggested answers. Each answer, for example, may be associated is an interactive object such as a checkbox that provide a selection of one or more answers. The questions, and the lists of one or more answers, can be provided in the user interface of the application executing on the mobile device. Example answers to the question related to eye color may include, but are not limited to "light blue", "gray", "green", "dark brown", "brownish black", or any combination thereof. Example answers to the question related to hair color may include "red", "sandy red", "blonde", "chestnut", "dark blonde", "brown", "dark brown", "black", or any combination thereof. Example answers to questions related to skin color may include "reddish", "pale", "very pale", "pale with beige tint", "beige", "light brown", "brown", "dark brown", or any combination thereof. Example answers to questions relating to the presence of freckles on unexposed areas may include "many", "several", "few", "incidental", "none", or any combination thereof. Example answers to questions relating to what happens when the user stays too long in the sun may include "painful redness", "blistering", "peeling", "burns", "rare burns", "never had burns", or any combination thereof. Example answers to questions relating to what degree the user turns brown may include "not at all", "hardly", "light color tan", "reasonable tan", "tan very easily", "turn dark brown very easily", or any combination thereof. Example answers to questions relating to whether the user turns brown with several hours of sun exposure may include "never", "seldom", "sometimes", "often", "always", or any combination thereof. Example answers to questions relating to how the user's face reacts to the sun may include "very sensitive", "sensitive", "normal", "very resistant", "never had a problem", or any combination thereof.

Using the application, the user of the mobile device 102 may utilize or otherwise provide user specific information or clinically relevant data. This information can be any data about the user that may be used to arrive at a skin color classification, diagnosis, or treatment plan. In addition, and in order to establish baseline skin data, the user may be prompted to provide photographs or images of normal (e.g. undiseased, etc.) skin. This data may be used to aid in or determining skin diagnosis, conditions, color classifications, or treatment plans. After the user inputs the data to the application executing on the mobile device 102, the applicant can transmit or upload the data to a secure and encrypted database, such as the cloud based healthcare data 225. The process of skin classification, diagnosis, and identification or selection of individualized treatment plans are described in further detail below in conjunction with FIGS. 3A-3C and 4-6.

The cloud based healthcare data 225 can store or maintain any of the data described herein, including any data provided by the user or any data determined or generated by the various computing devices or modules detailed above or below. The cloud based healthcare data 225 can be an encrypted database, such that it may only be accessed or updated by computing devices that have a private key that is unique to each user in the system. The data in cloud based healthcare data 225 may include one or more data structures that are indexed or associated with a user identifier. Each of the data structures that are indexed or associated with a particular user identifier can maintain or store information from a corresponding unique user. In addition, encryption methods such as public-private key encryption may be used such that only the computing devices with access to the private key can access or modify data. Each user identifier, and the data associated or index therewith, may be encrypted with a private key maintained on the mobile device of the user. The public-private key can be, for example, any type of asymmetric encryption scheme (e.g., Ed25519 signing, X25519 key exchange, Ed448 signing, X448 key exchange, elliptic curve cryptography, RSA encryption, Diffie-Hellman key exchange, DSA encryption, key serialization, ElGamal encryption, etc.), or any other type of encryption scheme for storage.

Figure 3A:
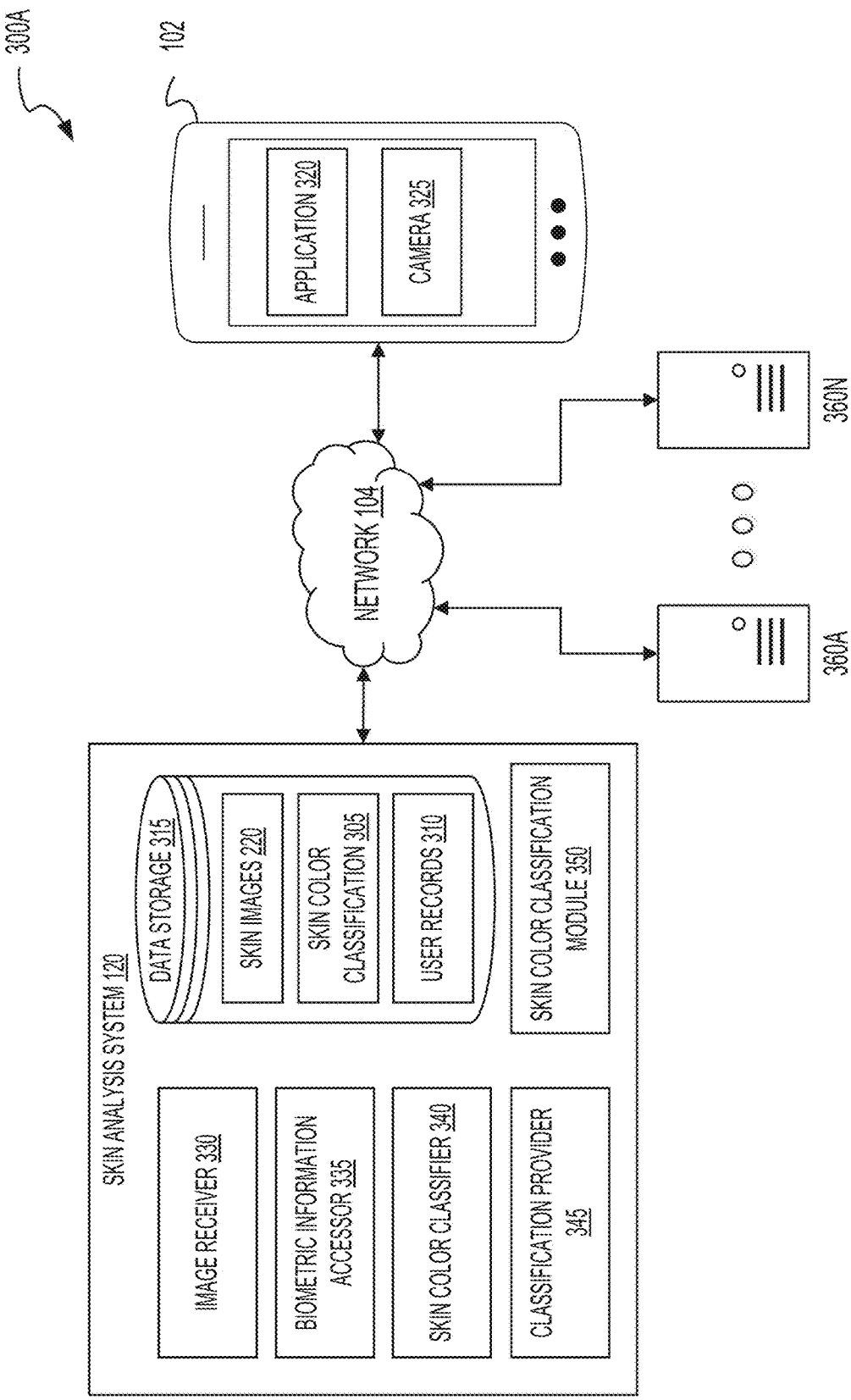
FIG. 3A illustrates a block diagram of an example system for determining a numerical classification of human skin color.
Figure 3B:
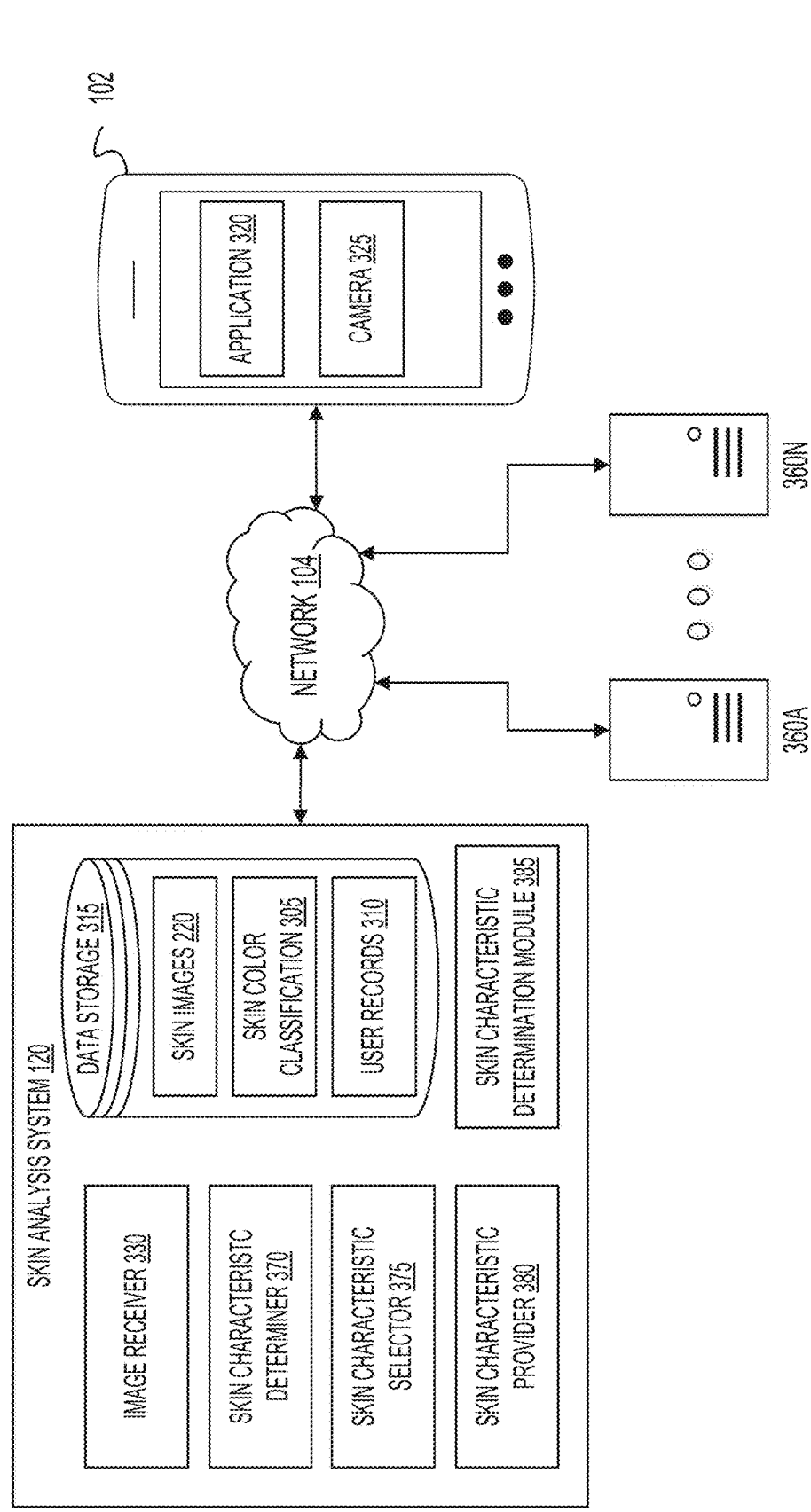
FIG. 3B illustrates a block diagram of an example system for identifying or determining one or more characteristics of human skin.
Figure 3C:
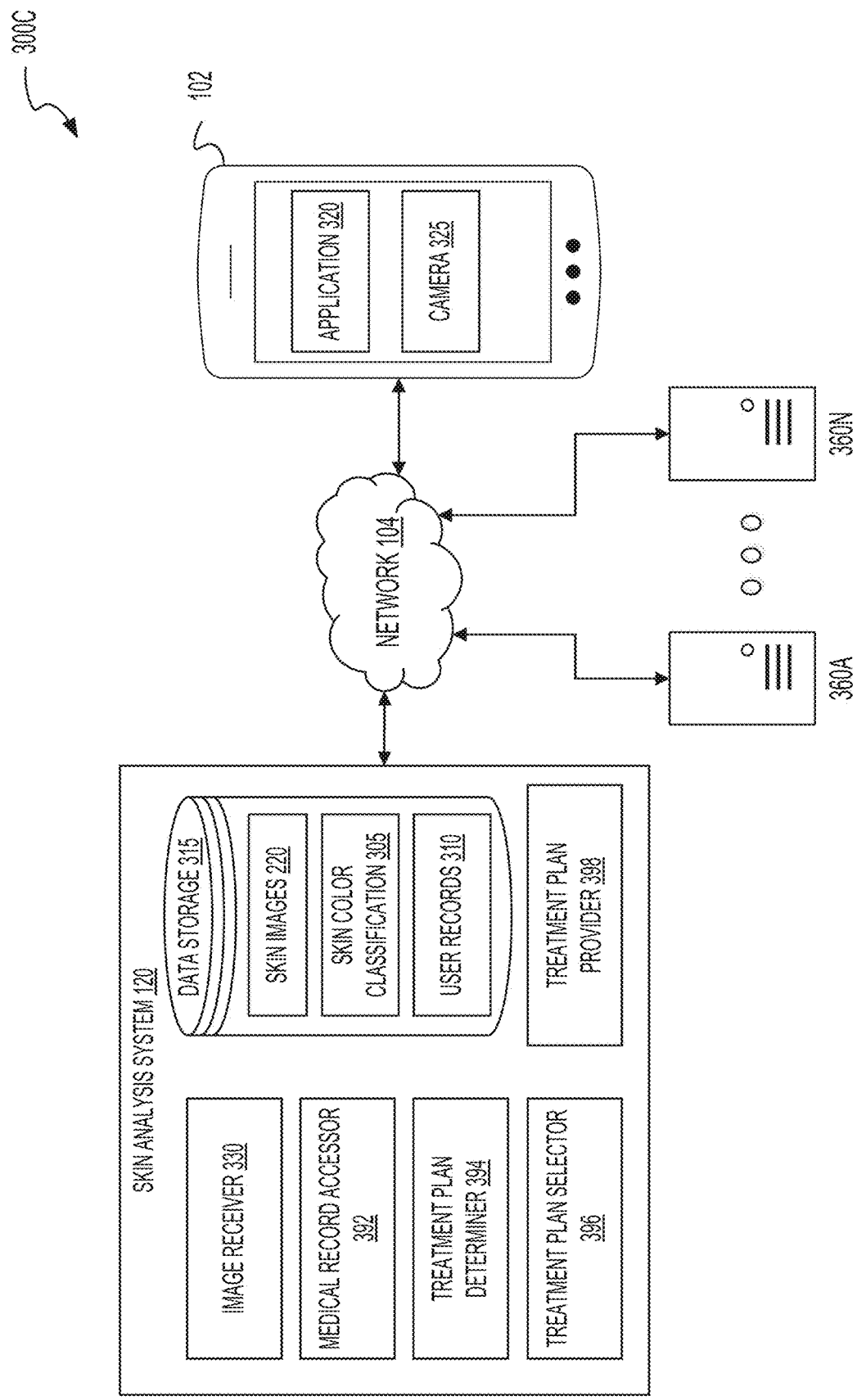
FIG. 3C illustrates a block diagram of an example system for analyzing skin images to determine a personalized treatment plan.

The cloud-based healthcare data 255 can be implemented, for example, to be a part of or any of the data storage 315 described herein in conjunction with FIGS. 3A-3C. The application executing on the can use a private key or another type of decryption key to access, retrieve, update, or otherwise modify the data present in any of the cloud based healthcare data 225 or the data storage 315. For example, the application may maintain a private decryption key that is unique to the user of the mobile device. The decryption key may be configured such that it points to the location of and can decrypt only the associated user's data in the cloud based healthcare data 225 (or the data storage 315, etc.). Thus, the user of the application on the mobile device can access and update any data records associated with the user. The application may permit other computing devices to access private data of the user stored in the cloud based healthcare data 225 or the data storage 315 by distributing the decryption key, or by providing instructions to (e.g., authorizing or otherwise granting access to, etc.) any of the computing devices described herein to provide access to the data of the user stored in the cloud based healthcare data 225 or the data storage 315.

Accordingly, any of the skin color classifier 230, the clinical decision support system 235, each of which may be implemented by the skin analysis system 120, can access or be granted access to (e.g., to receive, retrieve, read from, write to, update, add to, or otherwise alter, etc.) any of the data of the user stored in the data storage 315 (e.g., the skin images 220, skin color classification 305, the user records 310, or any other information as described herein, etc.) the cloud based healthcare data 225. Each of the computing devices of system 200 (e.g., the mobile device 102, the cloud based healthcare data 225, the skin color classifier 230, the clinical support systems 235, etc.) can communicate with each other over a network, such as the network 104 described herein above in conjunction with FIGS. 1A-1D.

Although the skin color classifier 230, the cloud based healthcare data, and the clinical support systems 235 are depicted as separate entities in system 200, it should be understood that each of these entities may be implemented by one or more computing devices or a data processing system, such as the skin analysis system 120 described in g. Indeed, the skin analysis system 120 or the components thereof in the various implementations presented in FIGS. 3A-3C can perform any of the functionalities of any of the computing devices depicted in system 200 of FIG. 2. A comprehensive description of various implementations of the skin analysis system 120 are described herein below in conjunction with FIGS. 3A-3C.

Referring now to FIGS. 3A-3C, depicted are different implementations of the operations of the skin analysis system 120. Although depicted to include different components in each of the systems 300A, 300B, and 300C of the respective FIGS. 3A, 3B, and 3C, it should be understood that each of these implementations are not necessarily separate, and may exist in any combination of components, elements, or features. Indeed, each of the depictions of the skin analysis system 120 of the systems 300A, 300B, or 300C may perform any of the functionalities of the other systems, and may include any combination of computing devices, components, applications, or elements as described in any of those figures. As such, the depictions of the skin analysis system 120 should not necessarily be considered separate embodiments or implementations, and can instead operate or perform any of the functionalities of any embodiment or implementation of the skin analysis system 120 as described herein. The same applies to any of the other computing devices or components thereof of the systems 300A, 300B, or 300C (e.g., the mobile device 102, the other computing devices 360A-N, the network 104, etc.).

Referring specifically now to FIG. 3A, illustrated is a block diagram of an example system 300A for determining a numerical classification of human skin color, in accordance with one or more implementations. The system 300A can, in some implementations, be the same as, perform all of the same operations as, or include the same components as, either or both of the system 300B or the system 300C. The system 300A can include at least one skin analysis system 120, at least one network 104, at least one other computing devices 360A-N (sometimes referred to generally as other computing device(s) 360), and at least one client device 102. The skin analysis system 120 can include at least one image receiver 330, at least one biometric information accessor 335, at least one skin color classifier 340, at least one classification provider 345, and at least one skin classification module 350. Although depicted as a part of the skin analysis system 120, the data storage 315 can be external to and communicatively coupled to the skin analysis system 120 via the network 104. In some implementations, the data storage 315 is internal to the skin analysis system, but may also be accessed by other computing devices via the network 104 with proper authorization (e.g., appropriate private key, password, instructions to authorize, etc.). The data storage 315 can include at least one skin images 220, at least one skin color classification 305, and at least one user records 310. The client device 102 (sometimes referred to as the mobile device 102) can include at least one application 320 and at least one camera 325.

Each of the image receiver 330, biometric information accessor 335, skin color classifier 340, classification provider 345, skin classification module 350, and data storage 315 of the system 300A can be implemented using the hardware components or a combination of software with the hardware components of a computing system (e.g., computing system 100, the skin analysis system 120, any other computing system described herein, etc.) detailed herein in conjunction with FIGS. 1A-1D. Each of the components of the skin analysis system 120 can perform the functionalities detailed herein.

The skin analysis system 120 can include at least one processor and a memory, e.g., a processing circuit. The memory can store processor-executable instructions that, when executed by processor, cause the processor to perform one or more of the operations described herein. The processor may include a microprocessor, an application-specific integrated circuit (ASIC), a field-programmable gate array (FPGA), etc., or combinations thereof. The memory may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The skin analysis system 120 can include one or more computing devices or servers that can perform various functions as described herein. The skin analysis system 120 can include any or all of the components and perform any or all of the functions of the computer system 100 described herein in conjunction with FIGS. 1A-1D.

The network 104 can include computer networks such as the Internet, local, wide, metro or other area networks, intranets, satellite networks, other computer networks such as voice or data mobile phone communication networks, and combinations thereof. The skin analysis system 120 of the systems 300A, 300B, and 300C as described herein in conjunction with FIGS. 3A-3C can communicate via the network 104, for instance with at least one client device 102. The network 104 may be any form of computer network that can relay information between the client device 102, other computing devices 360, and one or more content sources, such as web servers, amongst others. In some implementations, the network 104 may include the Internet and/or other types of data networks, such as a local area network (LAN), a wide area network (WAN), a cellular network, a satellite network, or other types of data networks. The network 104 may also include any number of computing devices (e.g., computers, servers, routers, network switches, etc.) that are configured to receive and/or transmit data within the network 104. The network 104 may further include any number of hardwired and/or wireless connections. Any or all of the computing devices described herein (e.g., the skin analysis system 120, the computer system 100, the client device 102, the other computing devices 360, etc.) may communicate wirelessly (e.g., via WiFi, cellular, radio, etc.) with a transceiver that is hardwired (e.g., via a fiber optic cable, a CAT5 cable, etc.) to other computing devices in the network 104. Any or all of the computing devices described herein (e.g., the skin analysis system 120, the computer system 100, the client device 102, the other computing devices 360, etc.) may also communicate wirelessly with the computing devices of the network 104 via a proxy device (e.g., a router, network switch, or gateway).

The data storage 315 can be a database or other computer storage configured to store and/or maintain any of the information described herein. The data storage 315 can maintain one or more data structures, which may contain, index, or otherwise store each of the values, pluralities, sets, variables, vectors, or thresholds described herein. The data storage 315 can be accessed using one or more memory addresses, index values, or identifiers of any item, structure, or region maintained in the data storage 315. The data storage 315 can be accessed by the components of the skin analysis system 120, or any other computing device described herein, via the network 104. In some implementations, the data storage 315 can be internal to the skin analysis system 120. In some implementations, the data storage 315 can exist external to the skin analysis system 120, and may be accessed via the network 104. The data storage 315 can be distributed across many different computer systems or storage elements, and may be accessed via the network 104 or a suitable computer bus interface. The skin analysis system 120 can store, in one or more regions of the memory of the skin analysis system 120, or in the data storage 315, the results of any or all computations, determinations, selections, identifications, generations, constructions, or calculations in one or more data structures indexed or identified with appropriate values. Any or all values stored in the data storage 315 may be accessed by any computing device described herein, such as the skin analysis system 120, to perform any of the functionalities or functions described herein.

The data storage 315 can maintain one or more skin images of the user. For example, the application 320 may provide, via the network, one or more images of a portion of the user's skin in one or more messages. The messages may include a decryption key, or a key that otherwise authorizes the client device 102 to access the data in the data storage 315 that is associated with the user. The data storage 315 can maintain, in one or more data structures in one or more regions of computer memory, the images of the messages transmitted by the application on the client device 102 via the network 104. These images can be accessed by computing devices that are authorized to access the data associated with the user or the client device 102, such as the skin analysis system 120, the other computing devices 360, or other computing devices as described herein.

The data storage 315 can store the results of the classification of user skin colors as the skin color classification 305 or as part of the skin color classification 305. The skin color classification 305 can be a numerical quantity that represents a skin tone or skin color of the user, and may be stored in one or more data structures in the data storage 315 in association with other data from the user (e.g., skin images 220, the user records 310, etc.). The skin color classification 305 can be, for example, a Fitzpatrick skin score of the user, and can be stored in association with other data of the user such as the medical records of the user. In some implementations, the skin color classification can be stored in association with a respective skin image 220 in the data storage 315.

The data storage 315 can store the user records 310 that include data the user has provided via the application 320. The user records 310 can include information about the user, such as answers to various questions about the user's skin, biometric information, medical records of the user, medical history of the user, diagnoses for the user determined by the skin analysis system 120, and other user information. The user records 310 can be stored in one or more data structures and be indexed by a user identifier that corresponds to the user of the mobile device 102. The data storage 315 can be an encrypted and Health Insurance Portability and Accountability Act (HIPAA) compliant data storage module that can maintain encrypted records of user data in association with one or more user identifiers. The, either through the client device 102 or through another computing device or authorization process, may authorize (e.g., distribute access instructions to, provide a private key to, provide a password to, etc.) the encrypted portions of the data storage 315 that are associated with the user. This can allow computing devices that the user has authorized to access the data in the data storage 315 that is associated with the user. For example, the data in the data storage 315 that is associated with the user may be encrypted, and may only be decrypted using a private key. To authorize access to the data in the data storage, the user may distribute the private key to other computing systems via the network 104 or another communication process.

In some implementations, the user records 310 can include user profile information. For example, the application 320 executing on the client device can register a user profile that can include any of the information associated with the user as described herein. This information can include, for example, any of the skin images 220, the skin color classification 305, or any other information as described herein that can be provided by the application 320 or the user. The user profile information may include information such as the email address of the user, the name of the user, or any other identifying information about the user.

The client device 102 (sometimes referred to as the mobile device 102) can include at least one processor and a memory, e.g., a processing circuit. The memory can store processor-executable instructions that, when executed by a processor, cause the processor to perform one or more of the operations described herein. The processor may include a microprocessor, an application-specific integrated circuit (ASIC), a field-programmable gate array (FPGA), etc., or combinations thereof. The memory may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The client device 102 can include one or more computing devices or servers that can perform various functions as described herein. The skin analysis system 120 can include any or all of the components and perform any or all of the functions of the computer system 100 described herein in conjunction with FIGS. 1A-1D.

The client device 102 can maintain and execute at least one application 320. The application 320 can include computer executable instruction, that when executed by the processor of the client device, cause the client device to display at least one user interface on a display of the client device 102. The application 320 may present a graphical user interface on a display coupled to a processor of the mobile device 102. The graphical user interface may be, for example, presented in response to executing the application 320. The mobile device 102 may receive the application 320 from one of the computing devices of the cloud 108, or another computing device external to the mobile device 102, or from the skin analysis system 120. The graphical user interface provided by the application 320 can present questions to a user (e.g., in the form of text, graphics, or other display objects, etc.), with appropriate spaces, input boxes, or other means to provide input to the computing device. For example, the user may provide a touch input on a virtual keyboard, or may interact with various actionable objections to make selections of various answers to questions displayed by the application 320.

The application 320 executing on the mobile device 102 can gather answers to the questions and store the information in one or more data structures in at least one region of the memory of the mobile device 102. For example, the questions may include, but are not limited to: "What color are your eyes?", "What is the natural color of your hair", "What color is your skin (unexposed areas)?", "Do you have freckles on unexposed areas?", or "What happens when you stay too long in the sun?", "To what degree do you turn brown", "Do you turn brown with several hours of sun exposure", or "How does your face react to the sun".

In response to the questions presented to the user in the application, the user may be prompted with one or more suggested answers. Each answer, for example, may be associated with a respective interactive object such as a checkbox that provide a selection of one or more answers in response to an interaction by the user. The questions, and the lists of one or more answers, can be provided in the user interface of the application 320 executing on the mobile device 102. Example answers to the question related to eye color may include, but are not limited to "light blue", "gray", "green", "dark brown", "brownish black", or any combination thereof. Example answers to the question related to hair color may include "red", "sandy red", "blonde", "chestnut", "dark blonde", "brown", "dark brown", "black", or any combination thereof. Example answers to questions related to skin color may include "reddish", "pale", "very pale", "pale with beige tint", "beige", "light brown", "brown", "dark brown", or any combination thereof. Example answers to questions relating to the presence of freckles on unexposed areas may include "many", "several", "few", "incidental", "none", or any combination thereof. Example answers to questions relating to what happens when the user stays too long in the sun may include "painful redness", "blistering", "peeling", "burns", "rare burns", "never had burns", or any combination thereof. Example answers to questions relating to what degree the user turns brown may include "not at all", "hardly", "light color tan", "reasonable tan", "tan very easily", "turn dark brown very easily", or any combination thereof. Example answers to questions relating to whether the user turns brown with several hours of sun exposure may include "never", "seldom", "sometimes", "often", "always", or any combination thereof. Example answers to questions relating to how the user's face reacts to the sun may include "very sensitive", "sensitive", "normal", "very resistant", "never had a problem", or any combination thereof.

Using the application 320, the user of the mobile device 102 may enter or otherwise provide personal or clinically relevant data. The application 320 can communicate with any of the other computing devices coupled to the network 104. This information can be any data about the user that may be used to arrive at a skin color classification, diagnosis, or treatment plan. For example, the application can allow the user to create a user profile that includes identifying information. The user profile can be stored, for example, in the user records 310 of the data storage 315. In addition, and in order to establish baseline skin data, the user may be prompted to provide photographs or images of normal (e.g. undiseased, etc.) skin, that may be captured using the camera. This data may be used to aid in or determining skin diagnosis, conditions, color classifications, or treatment plans. After the user inputs the data to the application executing on the mobile device 102, the applicant can transmit or upload the data to a secure and encrypted database, such as the cloud based healthcare data 225. The process of skin classification, diagnosis, and identification or selection of individualized treatment plans are described in further detail below in conjunction with FIGS. 3A-3C and 4-6.

The client device 102 can include at least once camera 325. The camera may be integrated with the hardware of the client device 102, such as directly coupled to one or more data busses of the processor of the client device 102. In some implementations, the camera 325 can be coupled to the client device by other means, such as via a universal-serial bus connection or other type of serial or parallel connection. The camera 325 can capture light and produce one or more images. The applications or the operating system executing on the client device 102, such as the application 320, can access the camera 325 to capture one or more images. For example, the application 320 can capture one or more images using the camera and store them in the memory of the client device 102. The images can be captured in a variety of formats, for example a Joint Photographic Experts Group (JPEG) image, a portable network graphics (PNG) image, a Graphics Interchange Format (GIF) image, a Tagged Image File (TIFF) image, a Portable Document Format (PDF) image, or a RAW image format. After capturing one or more images, for example of a healthy portion of skin of the user or a diseased portion of skin of the user, the application 320 can transmit the images, and any other user information gathered by the application 320, to the image receiver 330 of the skin analysis system 120. By way of non-limiting example, the camera may be one of a smart phone, an external camera, a webcam, or external device coupled to the data processing system via a network.

The other computing devices 360A-N (sometimes referred to herein as the other computing devices 360), can be computing devices that are external to the skin analysis system 120 and the client device 102, but communicatively coupled to each via the network 104. For example, the other computing devices 360 can include computing devices of healthcare professionals, such as a skincare specialist that can be communicated with via the application 320 using voice chat or video chat. The other computing devices 360 can include other skin analysis systems 120, such as the other implementations described in herein below in conjunction with FIGS. 3B and 3C. However, it should be understood that the skin analysis system 120 of the system 300A is capable of performing some or all of the functionality of the skin analysis system 120 of the system 300B or the skin analysis system 120 of the system 300C described herein below in conjunction with FIGS. 3B and 3C.

The image receiver 330 can receive one or more images of skin of the user from the camera 325 of the client device 102. The skin can have a skin color. In some implementations, the application may prompt the user to include at least one reference object with a known color in the photo of skin. An example reference object can be, for example, a new United States dollar bill. In some implementations, the application 320 can transmit a request for a skin score color classification to the image receiver 330. In such implementations, the skin receiver 330 can receive the request for a skin color classification (e.g., the skin score or skin color value, etc.), which can include the one or more images of the skin of the user. Upon receiving the one or more images of the skin, the image receiver can store the images, for example, as the skin images 220 or as a part of the skin images 220. For example, if a region of memory in the data storage 315 already exists, the image receiver 330 can update the skin images 220 to include the images received from the application 320. In some implementations the image receiver 330 can receive one or more answers to questions, such as the answers to the various skin related questions provided by the user via the application 320 described herein above. The answers and the questions can be transmitted by the application 320 with the skin images (e.g., stored as the skin images 220, etc.), and can be stored by the image receiver 330 as part of the user records 310. In some implementations, if a user profile is indicated in one or more messages received from the application 320 (e.g., the messages including the images, answers to the questions, or other biometric information, etc.), the image receiver 330 can store the data in the messages received from the application 320 in the data storage 315 in association with the user profile.

The biometric information accessor 335 can access biometric information of the user received from the mobile device 102. The biometric information can include the answers to any of the questions presented to the user via the application 320 as described herein. The biometric information can include, for example, a reported skin color of the user, a natural hair color of the user, an eye color of the user, a reported likelihood of burning in the sun my the user, the height of the user, the weight of the user, or any other biometric information as described herein. Accessing the biometric information can include retrieving other information as needed by the skin color classifier 340 to classify the color of the skin of the user. For example, the biometric information accessor 335 can retrieve information from the data storage 315, such as the user records 310.

The biometric information accessor 335 can numerically encode the biometric information such that it can be provided as an input to a machine learning model. For example, each question may represent a position in a data structure. In a non-limiting example explanation, this data structure could be a vector with one or more coordinates. However, it should be understood that the data structure that encodes the biometric information need not be limited to a vector, and may take the form of the data structures, such as a matrix, a tensor, or other data structure suitable for use with a machine learning model (e.g., dense neural network, recurrent neural network, convolutional neural network, sparse vector machine, linear regression, etc.). Encoding the biometric information can include, for example, assigning each position in the data structure a portion of biometric information (e.g., one position for eye color, another for hair color, another for the first question, another for the second question, etc.). Each of the possible values for the biometric information can be assigned a numerical value (e.g. "blue eyes" can be assigned the number 1, "brown eyes" can be assigned the number 2, etc.). The data structure can then be populated according to the biometric information that is assigned to the user, and the data structure can be subsequently stored in association with the user profile in the user records 310. In a non-limiting example explanation, consider a data structure vector with only two positions: one for eye color, and another for hair color. If the user reports, using the application 320, an eye color of blue, and a hair color of brown, and the numerical assignment for blue eyes is 1 and the numerical assignment for brown hair is 3, the biometric information accessor 335 can generate a data structure as: [1, 3]. Although this non-limiting example has described the biometric information has having only two positions, it should be understood that the data structure can have any number of positions, numerical codes, and parameters.

The skin color classifier 340 can determine a classification of a skin color of the user using the image and the biometric information by providing the image and the biometric information as input to a skin color classification module 350. For example, the skin color classifier 340 can format one or more images (e.g., the skin images 220 received from the application 320, etc.) such that they can be used as input to the skin color classification module 350. Formatting an image can include, for example, adjusting the colors in the image based on a reference color. When an image is captured by application 320 executing on the mobile device 102, the user of the mobile device 102 can be instructed to include a reference object with a known color in the photograph.

Because the reference color is known by the skin color classifier 340 and will generally not change, the color can be used as a normalization color (e.g., a color from which the other colors in the image are compared and compensated). Further, the colors in the image can be adjusted based on a color in the image that is closest to the reference color. Images captured by mobile devices, such as the mobile device 102, can be captured in a variety of different lighting environments. To compensate for the differences in lighting in the image, the skin color classifier 340 can identify a color in the image (e.g., a group of adjacent pixels with an average color that is within a predetermined threshold of the reference color, etc.) that is closest to the reference color (e.g., a red-green-blue (RGB) pixel value, etc.), and determine a difference between the actual reference color (e.g., via subtraction, etc.). Upon determining the difference, the skin color classifier 340 can adjust (e.g., change, modify, etc.) the other colors in the image by adding or subtracting, as the case may be, the compensation value to each of the RGB pixel values the image to generate a compensated image, which can be used in further processing steps and ultimately used as input to the skin color classification module 350. In some implementations, the image may not include a reference color (or the user may not have been instructed to include a reference color, etc.). In such implementations, the system can proceed with further processing steps without compensating for differences in the color or lighting of the image.

To format the image as input to the model, the skin color classifier 340 can construct one or more data structures that represent the image. For example, skin color classifier may extract a pixel value for each pixel in the image. In some implementations, the image may be down scaled to a fixed resolution prior to extracting the pixel values (e.g., to 128×128, 256×256, 512×512, or 1024×1024 pixels, etc.). Extracting the pixel values can include identifying an RGB value for each pixel, and placing it into a corresponding position in the generated data structure. As such, each position in the data structure can have, for example, a three coordinate vector where each position in the vector corresponds to one of a red, green, and blue intensity of the respective pixel in the image. In some implementations, the skin color classifier 340 can average the blue, red, and green values of each pixel together to generate a grayscale image prior to extracting the pixel values to populate the data structure. In such implementations, the data structure generated using the grayscale image can have one coordinate per pixel. In some implementations, the skin color classifier 340 can normalize the data structure that represents the image prior to providing it as input to the skin color classification module 350.

To determine the classification of the skin color of the user, the skin color classifier 340 can provide the data structure that represents the image or the data structure that represents the biometric information as the input layer to the skin color classification module 350. Providing the data structures as an input layer can include normalizing (e.g., scaling the values of the data structures such that their coordinate values are floating point values each between zero and one, etc.). After providing the data structures as input to the skin color classification module 350, the skin color classifier 340 can propagate (e.g., perform the mathematical computations of each layer, etc.) the data through the skin color classification module 350 until the skin classification module 350 produces an output value that is representative of a classification of the skin color. For example, in the case where the skin classification module 350 is trained to determine a Fitzpatrick skin score, the output value can be a value between 1 and 6. In the case of the Fitzpatrick skin score, a value of 1 can refer to skin that is very pale, and a value of 6 can refer to skin that is very dark.

In some implementations, the skin color classifier 340 can receive more than one skin color classification output values from the skin color classification module 350 (e.g., as a series of classification values in an output vector or other output data structure, etc.). In such implementations, the skin color classifier 340 can select a skin color classification from the on one or color classification output values having a value greater than another of the plurality of skin color classification output values. In a non-limiting example implementation, the output vector of the skin color classification module 350 can have six positions, with each position corresponding to a respective one of the six Fitzpatrick skin score values. The skin color classification module 350 can output a confidence score (e.g., floating point value between zero and one, etc.) at each position, and the skin color classifier 340 can select whichever position has the highest confidence score. Thus, if the output vector is [0.1, 0.5, 0.3, 0.04, 0.06, 0.0], and the leftmost value represents a Fitzpatrick skin score of 1 and the rightmost value represents a Fitzpatrick skin score of 6, the skin color classifier can determine the Fitzpatrick skin score of 2 as the classification of the skin color of the user.

The classification provider 345 can provide the classification of the skin color of the user to the mobile device. For example, the classification provider 345 may transmit a message (e.g., which may be a response message to the request for classification, etc.) to the application 320 of the mobile device 102 via the network 104. The message can include, the classification of the skin score of the user (e.g., the Fitzpatrick skin score, etc.), and may include instructions to display the classification of the skin score on the display of the mobile device 102. In some implementations, the classification provider 345 can store the skin score for the user in association with one or more user records 310, such as medical records, a user profile, or other user information in the data storage 315 of the skin analysis system 120.

The skin color classification module 350 can be, for example, a recurrent neural network that is configured to accept one or more data structures that are representative of images or of encoded biometric information. The skin color classification module 350 can be a Fitzpatrick score neural network classifier (e.g., produce an output value that is representative of at least one Fitzpatrick skin score, etc.). Since skin color classification may not depend on fine details in the image, a fairly simple and shallow (e.g., a network with few layers, etc.) network can be used and trained as the skin color classification module 350. In one implementation, the skin color classification module can include a gated recurrent neural network architecture (e.g., the gated neural network architecture depicted in FIG. 7A and described herein below, etc.).

The skin color classification module 350 can take as an input layer the image data and numerically coded biometric information. This data can be configured as an input vector, matrix, or tensor that is commensurate with the structure of the skin color classification module 350 input layer. The gated neural network of the skin color classification module 350 can include several layers of gates, which can feed into a dense or fully connected neural network layer. The output of the densely connected layer or layers can be provided as input into one or activation modules, which can include applying (e.g., performing one or more functions on, etc.) activation functions to the data. The activation functions may include, for example, an identity function, a binary step function, a logistic or sigmoid function, a tan h function, an arctan function, a rectified linear unit (ReLu) function, a leaky ReLu function, or a soft-max function, among others. The output of the activation layer can be provided directly as an output layer, and can be a representative skin score (in this example, a Fitzpatrick classification between 1 and 6, etc.). The output of the skin color classification module 350 can be provided or used by the skin color classifier 340.

In some implementations, the skin color classifier 340 can update the skin color classification module 350 using known training data (e.g., an actual classification of the skin in an image under analysis, etc.). To train the skin color classification module 350, the skin color classifier can input the image associated with the known skin classification value to the skin color classification module 350, and receive an output value of the skin score. The skin color classifier 340 can subtract or otherwise determine a difference between the actual classification of the skin color and the value output by the skin color classification module 350. Using this difference, the skin color classifier 340 can update the weights and biases of each layer in the skin color classification module 350 using the difference value and a machine learning algorithm (e.g., a gradient descent algorithm, etc.).

In some implementations, the skin analysis system 120 can provide the application 320 to the mobile device 102, for example in response to a request to install or download the application 320. In some implementations, the application 320 is a web browser executing on the client device 102, and the skin analysis system can transmit instructions to present, via the application 320 executing on the mobile device 102, a graphical user interface, such as a web interface, that can provide the one or more questions as described herein. In such implementations, the skin analysis system can provide instructions to the application 320 executing on the client device to perform any of the features of the application 320 as described herein.

Referring now to FIG. 3B, illustrated is a block diagram of an example system 300B for determining a classification of one or more skin characteristics, in accordance with one or more implementations. The system 300B can, in some implementations, be the same as, perform all of the same operations as, or include the same components as, either or both of the system 300A or the system 300C. The system 300B can include at least one skin analysis system 120, at least one network 104, at least one other computing devices 360A-N (sometimes referred to generally as other computing device(s) 360), and at least one client device 102. The skin analysis system 120 can include at least one image receiver 330, at least one skin characteristic determiner 370, at least one skin characteristic selector 375, at least one skin characteristic provider 380, and at least one skin characteristic determination module. Although depicted as a part of the skin analysis system 120, the data storage 315 can be external to and communicatively coupled to the skin analysis system 120 via the network 104. In some implementations, the data storage 315 is internal to the skin analysis system, but may also be accessed by other computing devices via the network 104 with proper authorization (e.g., appropriate private key, password, instructions to authorize, etc.). The data storage 315 can include at least one skin images 220, at least one skin color classification 305, and at least one user records 310. The client device 102 (sometimes referred to as the mobile device 102) can include at least one application 320 and at least one camera 325.

Each of the image receiver 330, the skin characteristic determiner 370, the skin characteristic selector 374, the skin characteristic provider 380, the skin characteristic determination module 385, and the data storage 315 of the system 300B can be implemented using the hardware components or a combination of software with the hardware components of a computing system (e.g., computing system 100, the skin analysis system 120, any other computing system described herein, etc.) detailed herein in conjunction with FIGS. 1A-1D. Each of the components of the skin analysis system 120 can perform the functionalities detailed herein.

At least in the context of the system 300B, the skin analysis system 120 can include at least one processor and a memory, e.g., a processing circuit. The memory can store processor-executable instructions that, when executed by processor, cause the processor to perform one or more of the operations described herein. The processor may include a microprocessor, an application-specific integrated circuit (ASIC), a field-programmable gate array (FPGA), etc., or combinations thereof. The memory may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The skin analysis system 120 can include one or more computing devices or servers that can perform various functions as described herein. The skin analysis system 120 can include any or all of the components and perform any or all of the functions of the computer system 100 described herein in conjunction with FIGS. 1A-1D.

At least in the context of the system 300B, the network 104 can include computer networks such as the Internet, local, wide, metro or other area networks, intranets, satellite networks, other computer networks such as voice or data mobile phone communication networks, and combinations thereof. The skin analysis system 120 of the systems 300A, 300B, and 300C as described herein in conjunction with FIGS. 3A-3C can communicate via the network 104, for instance with at least one client device 102. The network 104 may be any form of computer network that can relay information between the client device 102, other computing devices 360, and one or more content sources, such as web servers, amongst others. In some implementations, the network 104 may include the Internet and/or other types of data networks, such as a local area network (LAN), a wide area network (WAN), a cellular network, a satellite network, or other types of data networks. The network 104 may also include any number of computing devices (e.g., computers, servers, routers, network switches, etc.) that are configured to receive and/or transmit data within the network 104. The network 104 may further include any number of hardwired and/or wireless connections. Any or all of the computing devices described herein (e.g., the skin analysis system 120, the computer system 100, the client device 102, the other computing devices 360, etc.) may communicate wirelessly (e.g., via WiFi, cellular, radio, etc.) with a transceiver that is hardwired (e.g., via a fiber optic cable, a CAT5 cable, etc.) to other computing devices in the network 104. Any or all of the computing devices described herein (e.g., the skin analysis system 120, the computer system 100, the client device 102, the other computing devices 360, etc.) may also communicate wirelessly with the computing devices of the network 104 via a proxy device (e.g., a router, network switch, or gateway).

At least in the context of the system 300B, the data storage 315 can be a database or other computer storage configured to store and/or maintain any of the information described herein. The data storage 315 can maintain one or more data structures, which may contain, index, or otherwise store each of the values, pluralities, sets, variables, vectors, or thresholds described herein. The data storage 315 can be accessed using one or more memory addresses, index values, or identifiers of any item, structure, or region maintained in the data storage 315. The data storage 315 can be accessed by the components of the skin analysis system 120, or any other computing device described herein, via the network 104. In some implementations, the data storage 315 can be internal to the skin analysis system 120. In some implementations, the data storage 315 can exist external to the skin analysis system 120, and may be accessed via the network 104. The data storage 315 can be distributed across many different computer systems or storage elements, and may be accessed via the network 104 or a suitable computer bus interface. The skin analysis system 120 can store, in one or more regions of the memory of the skin analysis system 120, or in the data storage 315, the results of any or all computations, determinations, selections, identifications, generations, constructions, or calculations in one or more data structures indexed or identified with appropriate values. Any or all values stored in the data storage 315 may be accessed by any computing device described herein, such as the skin analysis system 120, to perform any of the functionalities or functions described herein.

At least in the context of the system 300B, the data storage 315 can maintain one or more skin images of the user. For example, the application 320 may provide, via the network 104, one or more images of a portion of the user's skin in one or more messages. The messages may include a decryption key, or a key that otherwise authorizes the client device 102 to access the data in the data storage 315 that is associated with the user. The data storage 315 can maintain, in one or more data structures in one or more regions of computer memory, the images of the messages transmitted by the application on the client device 102 via the network 104. These images can be accessed by computing devices that are authorized to access the data associated with the user or the client device 102, such as the skin analysis system 120, the other computing devices 360, or other computing devices as described herein.

At least in the context of the system 300C, the data storage 315 can store the results of the classification of user skin colors as the skin color classification 305 or as part of the skin color classification 305. For example, the skin color classification determined by at least the system 300A described herein above in conjunction with FIG. 3A can be maintained in the data storage 315 as the skin color classification 305. The skin color classification 305 can be a numerical quantity that represents a skin tone or skin color of the user, and may be stored in one or more data structures in the data storage 315 in association with other data from the user (e.g., skin images 220, the user records 310, etc.). The skin color classification 305 can be, for example, a Fitzpatrick skin score of the user, and can be stored in association with other data of the user such as the medical records of the user or a user profile. In some implementations, the skin color classification can be stored in association with a respective skin image 220 in the data storage 315.

At least in the context of the system 300B, the client device 102 can maintain and execute at least one application 320. The application 320 can include computer executable instructions, that when executed by the processor of the client device, cause the client device to display at least one user interface (e.g., a graphical user interface, etc.) on a display of the client device 102. The application 320 may present a graphical user interface on a display coupled to a processor of the mobile device 102. The graphical user interface may be, for example, presented in response to executing the application 320. The mobile device 102 may receive the application 320 from one of the computing devices of the cloud 108, or another computing device external to the mobile device 102, or from the skin analysis system 120. The graphical user interface provided by the application 320 can present questions to a user (e.g., in the form of text, graphics, or other display objects, etc.), with appropriate spaces, input boxes, or other means to provide input to the computing device. For example, the user may provide a touch input on a virtual keyboard, or may interact with various actionable objects to make selections of various answers to questions displayed by the application 320.

At least in the context of the system 300B, the application 320 executing on the mobile device 102 can gather answers to the questions and store the information in one or more data structures in at least one region of the memory of the mobile device 102. For example, the questions may include those that are intended to gather information related to particular skin condition. The answers to these questions can transmitted to the skin analysis system 120 for use in diagnosing one or more skin conditions. The questions displayed or otherwise presented by the application can include, but are not limited to variations of: "What is the duration of the skin condition?", "Have you had any prior treatments?", "Do you have a prior history of skin conditions", "Do you use drugs?", "Do you have a systematic illness?", "Do you have a family history of skin diseases?", "Is the lesion painful or painless?", "Does the lesion itch?", "Is there a burning sensation?", among others. The user can provide one or more answers to the questions via the application executing on a computing device (e.g., mobile device, other computing device described herein) of the user. In response to the questions presented to the user in the application, the user may be prompted with one or more suggested answers. Each answer, for example, may be associated with a respective interactive object such as a checkbox, yes or no answer, scroll menu (e.g., a pop-up menu with one or more selectable objects, such as dates, durations, etc.), or other interactive objects that provide a selection of one or more answers in response to an interaction (e.g., touch input, click, etc.) by the user. The questions, and the one or more answers, can be provided in the user interface of the application 320 executing on the mobile device 102.

Using the application 320, the user of the mobile device 102 may enter or otherwise provide personal or clinically relevant data. The application 320 can communicate with any of the other computing devices coupled to the network 104. This information can be any data about the user that may be used to arrive at a skin color classification, diagnosis, or treatment plan. For example, the application can allow the user to create a user profile that includes identifying information. The user profile can be stored, for example, in the user records 310 of the data storage 315. In addition, and in order to establish baseline skin data, the user may be prompted to provide photographs or images of normal (e.g. undiseased, etc.) skin, that may be captured using the camera. This data may be used to aid in or determining skin diagnosis, conditions, color classifications, or treatment plans. After the user inputs the data to the application executing on the mobile device 102, the applicant can transmit or upload the data to a secure and encrypted database, such as the cloud based healthcare data 225.

The application 320 can provide a menu or interface that allows the user to request a diagnosis for a particular skin condition. Upon selecting the option to request a diagnosis, the user may be prompted to provide one or more skin images of a diseased portion of skin, or an area of skin that may be of concern to the user. For example, the application 320 may present access a camera (e.g. the camera 325) of the mobile device 102 to request that the user take at least one image of a diseased portion of skin. The application 320 may present instructions to the user about the contents of the one or more image, such as requesting that the user present a reference object having a reference color in the same images as the diseased portion of skin. The application 320 may request that the user take a number of images using the camera. For example, the application 320 may request that the user take five photographs of the skin area of concern. After capturing the images of the potentially diseased area of skin, the application 320 can transmit the images and the user information in one or more messages to the skin analysis system 120, for example as part of a request for a skin diagnosis.

The client device 102 can include at least once camera 325. The camera may be integrated with the hardware of the client device 102, such as directly coupled to one or more data busses of the processor of the client device 102. In some implementations, the camera 325 can be coupled to the client device by other means, such as via a universal-serial bus connection or other type of serial or parallel connection. The camera 325 can capture light and produce one or more images. The applications or the operating system executing on the client device 102, such as the application 320, can access the camera 325 to capture one or more images. For example, the application 320 can capture one or more images using the camera and store them in the memory of the client device 102. The images can be captured in a variety of formats, for example a Joint Photographic Experts Group (JPEG) image, a portable network graphics (PNG) image, a Graphics Interchange Format (GIF) image, a Tagged Image File (TIFF) image, a Portable Document Format (PDF) image, or a RAW image format. After capturing one or more images, for example of a healthy portion of skin of the user or a diseased portion of skin of the user, the application 320 can transmit the images, and any other user information gathered by the application 320, to the image receiver 330 of the skin analysis system 120. By way of non-limiting example, the camera may be one of a smart phone, an external camera, a webcam, or external device coupled to the data processing system via a network.

At least in the context of the system 300B, the other computing devices 360A-N (sometimes referred to herein as the other computing devices 360), can be computing devices that are external to the skin analysis system 120 and the client device 102, but communicatively coupled to each via the network 104. For example, the other computing devices 360 can include computing devices of healthcare professionals, such as a skincare specialist that can be communicated with via the application 320 using voice chat or video chat. The other computing devices 360 can include other skin analysis systems 120, such as the other implementations described in herein above in conjunction with FIG. 3A, or below in conjunction with FIG. 3C. However, it should be understood that the skin analysis system 120 of the system 300B is capable of performing some or all of the functionality of the skin analysis system 120 of the system 300A or the skin analysis system 120 of the system 300C, and may include any or all of the components of the skin analysis system 120 as described in the context of those systems.

At least in the context of system 300B, the image receiver 330 can receive one or more images of skin of the user from the camera 325 (e.g., via the application 320, etc.) of the client device 102. The skin can have a skin color. In some implementations, the application may prompt the user to include at least one reference object with a known color in the photo of skin. An example reference object can be, for example, a new United States dollar bill. In some implementations, the application 320 can transmit a request for a skin diagnosis classification to the image receiver 330. In such implementations, the image receiver 330 can receive the request for a skin diagnosis classification (e.g., a disease, status, or characteristic, etc.), which can include the one or more images of the skin of the user. The request for a skin diagnosis can include other information about the user, such as the answers to the questions, any user profile information described herein, or any information received from the user by the application 320 as described in this technical solution. Upon receiving the one or more images of the skin and the user information, the image receiver 330 can store the images, for example, as the skin images 220 or as a part of the skin images 220. For example, if a region of memory in the data storage 315 already exists, the image receiver 330 can update the skin images 220 to include the images received from the application 320.

In some implementations the image receiver 330 can receive one or more answers to questions, such as the answers to the various skin related questions provided by the user via the application 320 described herein above. The answers and the questions can be transmitted by the application 320 with the skin images (e.g., stored as the skin images 220, etc.), and can be stored by the image receiver 330 as part of the user records 310. In some implementations, if a user profile is indicated in one or more messages received from the application 320 (e.g., the messages including the images, answers to the questions, or other biometric information, any other information from the user, etc.), the image receiver 330 can store the data in the messages received from the application 320 in the data storage 315 in association with the user profile (e.g., in the user records 310, etc.).

The skin characteristic determiner 370 can numerically encode the biometric information and other medically relevant user information such that it can be provided as an input to a machine learning model (e.g., the skin characteristic determination module 385, etc.). For example, each portion of medically relevant information may represent a position in a data structure. In a non-limiting example explanation, this data structure could be a vector with one or more coordinates. However, it should be understood that the data structure that encodes the biometric information need not be limited to a vector, and may take the form of the data structures, such as a matrix, a tensor, or other data structure suitable for use with a machine learning model (e.g., dense neural network, recurrent neural network, convolutional neural network, sparse vector machine, linear regression, etc.). Encoding the user information can include, for example, assigning each position in the data structure a portion of user information (e.g., one position for duration of skin condition, another for a whether the condition is itchy, or any other information associated with the user as described herein, etc.). Each of the possible values for the user information can be assigned a numerical value (e.g. a yes/no question can be assigned a binary zero or a binary one, number of days can be assigned the number of days the user has had the condition, etc.). The data structure can then be populated according to the user information that is provided by the user or gathered from any other source as described herein, and the data structure can be subsequently stored in association with the user profile in the user records 310. To access the information to populate the data structures, the skin characteristic determiner 370 can access any of the data present in the data storage 315. In a non-limiting example explanation, consider a data structure vector with only two positions: one for duration of condition, and another for burning sensation. If the user reports, using the application 320, that the condition has been present for 7 days, and that the condition includes a burning sensation, the skin characteristic determiner 370 can generate a data structure as: [7, 1]. Although this non-limiting example has described the user information as having only two positions or portions, it should be understood that the data structure can have any number of positions, numerical codes, and parameters based on the amount of user provided information or the size of the input layer of the skin characteristic determination module 385.

The skin characteristic determiner 370 can format one or more images (e.g., the skin images 220 received from the application 320, etc.) such that they can be used as input to the skin characteristic determination module 385. Formatting an image can include, for example, adjusting the colors in the image based on a reference color, adjusting the color of the image to grayscale, downscaling or upscaling the images to predetermined resolutions, cropping the image to an identified area of interest, or any combination thereof. When an image is captured by application 320 executing on the mobile device 102, the user of the mobile device 102 can be instructed (e.g., in the user interface of the application 320) to include a reference object with a known color in the image.

Because the reference color is known by the skin color classifier 340 and will generally not change, the color can be used as a normalization color (e.g., a color from which the other colors in the image are compared and compensated). Further, the colors in the image can be adjusted based on a color in the image that is closest to the reference color. Images captured by mobile devices, such as the mobile device 102, can be captured in a variety of different lighting environments. To compensate for the differences in lighting in the image, the skin characteristic determiner 370 can identify a color in the image (e.g., a group of adjacent pixels with an average color that is within a predetermined threshold of the reference color, etc.) that is closest to the reference color (e.g., an RGB pixel value, etc.), and determine a difference between the actual reference color (e.g., via subtraction, etc.). Upon determining the difference, the skin characteristic determiner 370 can adjust (e.g., change, modify, etc.) the colors in the image by adding or subtracting, as the case may be, the compensation value to each of the RGB pixel values the image to generate a compensated image, which can be used in further processing steps and ultimately used as input to the skin characteristic determination module 385. In some implementations, the image may not include a reference color (or the user may not have been instructed to include a reference object having a reference color, etc.). In such implementations, the system can proceed with further processing steps without compensating for differences in the color or lighting of the image.

To format the image as input to the model, the skin characteristic determiner 370 can construct one or more data structures that represent the image. For example, the skin characteristic determiner 370 can extract a pixel value for each pixel in the image. In some implementations, the image may be down scaled to a fixed resolution prior to extracting the pixel values (e.g., to 128×128, 256×256, 512×512, or 1024×1024 pixels, etc.). Extracting the pixel values can include identifying an RGB value for each pixel, and placing it into a corresponding position in the generated data structure. As such, each position in the data structure can have, for example, a three coordinate vector where each position in the vector corresponds to one of a red, green, and blue intensity of the respective pixel in the image. In some implementations, the skin color classifier 340 can average (e.g., weighted average, etc.) the blue, red, and green values of each pixel together to generate a grayscale image prior to extracting the pixel values to populate the data structure. In such implementations, the data structure generated using the grayscale image can have one coordinate per pixel. In some implementations, the skin characteristic determiner 370 can normalize the data structure that represents the image prior to providing it as input to the skin characteristic determination module 385. In some implementations, the skin characteristic determiner 370 can perform each of these steps for all of the images in a request for a diagnosis received from the mobile device 102.

To determine a set of output probabilities corresponding to a respective set of possible diagnoses of the diseased skin in the images, the skin characteristic determiner 370 can provide the data structure that represents the images or the data structure that represents the user information as the input layer to the skin characteristic determination module 385. Providing the data structures as an input layer can include normalizing (e.g., scaling the values of the data structures such that their coordinate values are floating point values each between zero and one, etc.). After providing the data structures as input to the skin characteristic determination module 385, the skin characteristic determiner 370 can propagate (e.g., perform the mathematical computations of each layer, etc.) the data through the skin characteristic determination module 385 until the skin characteristic determination module 385 produces a set of output probabilities corresponding to a respective set of possible diagnoses of the diseased skin in the images. In some implementations, the skin characteristic determiner 370 can input the data structures representing each image processed above one at a time. For example, certain neural networks, such as long-short term memory networks or recurrent neural networks, can have output that changes in response to a series of data rather than a single item of input data. Accordingly, the skin characteristic determiner 370 can input each of the data structures of the processed images (e.g., along with the data structure representing the user information held constant, etc.), into the skin characteristic determination module 385 in a series (e.g., one after another). The skin characteristic determiner 370 can receive an output data structure from the skin characteristic determination module 385, which can be provided to the skin characteristic selector 375 for additional processing.

The skin characteristic selector 375 can receive a data structure from the skin characteristic determiner 370 or the skin characteristic determination module 385 that includes a set of output probabilities corresponding to a respective set of possible diagnoses of the diseased skin in the images. For example, the data structure can be a vector that includes a number of coordinates. Each coordinate in the vector be a probability value, such as a probability value that is between zero and one, where zero represents a low likelihood that the skin is afflicted with the respective diagnosis, and where one represents a high likelihood that the skin is afflicted with the respective diagnosis. The skin characteristic selector 375 can select one or more of the positions in the data structure, and the respective diagnosis associated therewith, based on its corresponding probability value. For example, the skin characteristic selector 375 can compare each of the probability values in the data structure to a predetermined probability threshold. If the probability of a particular position or data entry in the data structure is greater than or equal to the threshold, the skin characteristic selector 375 can select the diagnosis associated with that position in the data structure as a likely diagnosis. The skin characteristic selector 375 can repeat this process for each position in the data structure to select a set of likely diagnoses. In some implementations, the skin characteristic selector 375 can sort the positions in the data structure to create a sorted data structure. In such implementations, the skin characteristic selector 375 can select a predetermined number of diagnoses (e.g., top five, top ten, etc.) in the data structure that have the greatest value or probability. The skin diagnoses may include, for example, an acne diagnosis, a cancer diagnosis, a diagnosis of a type of rash, or any other type of skin diagnosis or characteristic (e.g., dry skin, etc.). The skin characteristics can include a diagnosis of a skin condition.

In addition, once the skin characteristic of the skin depicted in the image has been determined, the skin analysis system 120 can determine a severity of the skin condition based on the selected characteristic. To do so, the skin analysis system 120 can utilize a machine learning model, such as the machine learning models implemented as part of the skin characteristic determination module 385 described in greater detail herein. For example, the machine learning model(s) used to determine the severity of a diagnosed skin condition, disease, or characteristic can take, as input, one or more of: the image depicting the skin, information in the medical record of the user, an identifier of the skin characteristic determined by the skin characteristic selector 375, or any other information relating to the user as described herein. Information provided as input to the model used to classify the severity of the skin condition can be similarly encoded, and the output of the model can provide one or more indications of the severity of the skin condition. For example, the output of the model can be a numerical value within a numerical range (e.g., zero to one hundred, etc.), with one end of the numerical range corresponding to the lowest level of severity, and the highest level of the range corresponding to the highest level of severity. In some implementations, the model can be specific to the skin characteristic detected in the image. For example, the skin analysis system 120 can maintain (e.g., store in a memory or database, etc.) a number of models that each correspond to a respective skin characteristic or diagnosis. In some implementations, upon determining the classification of the skin condition, the skin analysis system 120 can select the model corresponding to the skin condition and use the selected model to classify the severity of the skin condition.

The skin characteristic provider 380 can provide the one or more skin diagnoses or characteristics to the application 320 executing on the mobile device 102. For example, the classification provider 345 may transmit a message (e.g., which may be a response message to the request for classification, etc.) to the application 320 of the mobile device 102 via the network 104. The message can include, the classification of the one or more diagnoses (e.g., a type of acne, cancer, type rash, dry skin, etc.), a probability value associated with each diagnosis or characteristic, and any other information about the skin diagnosis or characteristics, such as a description of the diagnosis or characteristic. The message can include instructions to display the classification of the one or more diagnoses, characteristics, probabilities, or description, on the display of the mobile device 102. In some implementations, the skin characteristic provider 380 can store the one or more skin characteristics or diagnoses of the skin in association with one or more user records 310, such as medical records, a user profile, the images of the diseased skin, or other user information in the data storage 315 of the skin analysis system 120.

The skin characteristic determination module 385 can be, for example, a recurrent neural network that is configured to accept one or more data structures that are representative of images or of encoded biometric information. The skin characteristic determination module 385 can be a long-short term memory neural network classifier or a gated neural network classifier that is capable of producing an output vector that represents the probabilities of possible skin diagnoses present in images (e.g., an array of probabilities where each position in the array corresponds to a skin condition, disease, diagnoses, or characteristic, etc.).

The skin characteristic determination module 385 can take as an input layer the image data and numerically coded user information. This data can be configured as an input vector, matrix, or tensor that is commensurate with the structure of the skin characteristic determination module 385 input layer. In some implementations, such as a long-short-term memory implementation, the input layer of the skin characteristic determination module 385 can take a series of images as input (e.g., one after another with the user information data structure held constant, etc.). The gated neural network or the long-short term memory network of the skin color classification module 350 can include several layers of gates, which can feed into a dense or fully connected neural network layer. The output of the densely connected layer or layers can be provided as input into one or activation modules, which can include applying (e.g., performing one or more functions on, etc.) activation functions to the data. The activation functions may include, for example, an identity function, a binary step function, a logistic or sigmoid function, a tan h function, an arctan function, a rectified linear unit (ReLu) function, a leaky ReLu function, or a soft-max function, among others. The output of the activation layer can be provided directly as an output layer, and can a data structure, such as a vector, that has one or more coordinates that each represent a skin diagnosis, condition, or characteristic. The values of each coordinate can be output as a probability of the skin in the images input to the skin characteristic determination module 385 being afflicted with the corresponding condition or characteristic. The output layer of the skin characteristic determination module 385 can be provided or used by the skin characteristic determiner 370 or by the skin characteristic selector 375.

Referring now to FIG. 3C, illustrated is a block diagram of an example system 300C for analyzing skin images to determine at least one personalized treatment plan, in accordance with one or more implementations. The system 300C can, in some implementations, be the same as, perform all of the same operations as, or include the same components as, either or both of the system 300B or the system 300C described herein above in conjunction with FIGS. 3A and 3B. The system 300C can include at least one skin analysis system 120, at least one network 104, at least one other computing devices 360A-N (sometimes referred to generally as other computing device(s) 360), and at least one client device 102. The skin analysis system 120 can include at least one image receiver 330, at least one skin medical record accessor 392, at least one treatment plant determiner 394, at least one skin treatment plan selector 396, and at least one treatment plan provider 398. Although depicted as a part of the skin analysis system 120, the data storage 315 can be external to and communicatively coupled to the skin analysis system 120 via the network 104. In some implementations, the data storage 315 is internal to the skin analysis system 120, but may also be accessed by other computing devices via the network 104 with proper authorization (e.g., appropriate private key, password, instructions to authorize, etc.). The data storage 315 can include at least one skin images 220, at least one skin color classification 305, and at least one user records 310. The client device 102 (sometimes referred to as the mobile device 102) can include at least one application 320 and at least one camera 325.

Each of the image receiver 330, the medical record accessor 392, the treatment plan determiner 394, the treatment plan selector 396, the treatment plan provider, and the data storage 315 of the system 300B can be implemented using the hardware components or a combination of software with the hardware components of a computing system (e.g., computing system 100, the skin analysis system 120, any other computing system described herein, etc.) detailed herein in conjunction with FIGS. 1A-1D. Each of the components of the skin analysis system 120 can perform the functionalities detailed herein.

At least in the context of the system 300C, the skin analysis system 120 can include at least one processor and a memory, e.g., a processing circuit. The memory can store processor-executable instructions that, when executed by processor, cause the processor to perform one or more of the operations described herein. The processor may include a microprocessor, an application-specific integrated circuit (ASIC), a field-programmable gate array (FPGA), etc., or combinations thereof. The memory may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The skin analysis system 120 can include one or more computing devices or servers that can perform various functions as described herein. The skin analysis system 120 can include any or all of the components and perform any or all of the functions of the computer system 100 described herein in conjunction with FIGS. 1A-1D At least in the context of the system 300C, the network 104 can include computer networks such as the Internet, local, wide, metro or other area networks, intranets, satellite networks, other computer networks such as voice or data mobile phone communication networks, and combinations thereof. The skin analysis system 120 of the systems 300A, 300B, and 300C as described herein in conjunction with FIGS. 3A-3C can communicate via the network 104, for instance with at least one client device 102. The network 104 may be any form of computer network that can relay information between the client device 102, other computing devices 360, and one or more content sources, such as web servers, amongst others. In some implementations, the network 104 may include the Internet and/or other types of data networks, such as a local area network (LAN), a wide area network (WAN), a cellular network, a satellite network, or other types of data networks. The network 104 may also include any number of computing devices (e.g., computers, servers, routers, network switches, etc.) that are configured to receive and/or transmit data within the network 104. The network 104 may further include any number of hardwired and/or wireless connections. Any or all of the computing devices described herein (e.g., the skin analysis system 120, the computer system 100, the client device 102, the other computing devices 360, etc.) may communicate wirelessly (e.g., via WiFi, cellular, radio, etc.) with a transceiver that is hardwired (e.g., via a fiber optic cable, a CAT5 cable, etc.) to other computing devices in the network 104. Any or all of the computing devices described herein (e.g., the skin analysis system 120, the computer system 100, the client device 102, the other computing devices 360, etc.) may also communicate wirelessly with the computing devices of the network 104 via a proxy device (e.g., a router, network switch, or gateway)

At least in the context of the system 300C, the data storage 315 can be a database or other computer storage configured to store and/or maintain any of the information described herein. The data storage 315 can maintain one or more data structures, which may contain, index, or otherwise store each of the values, pluralities, sets, variables, vectors, or thresholds described herein. The data storage 315 can be accessed using one or more memory addresses, index values, or identifiers of any item, structure, or region maintained in the data storage 315. The data storage 315 can be accessed by the components of the skin analysis system 120, or any other computing device described herein, via the network 104. In some implementations, the data storage 315 can be internal to the skin analysis system 120. In some implementations, the data storage 315 can exist external to the skin analysis system 120, and may be accessed via the network 104. The data storage 315 can be distributed across many different computer systems or storage elements, and may be accessed via the network 104 or a suitable computer bus interface. The skin analysis system 120 can store, in one or more regions of the memory of the skin analysis system 120, or in the data storage 315, the results of any or all computations, determinations, selections, identifications, generations, constructions, or calculations in one or more data structures indexed or identified with appropriate values. Any or all values stored in the data storage 315 may be accessed by any computing device described herein, such as the skin analysis system 120, to perform any of the functionalities or functions described herein At least in the context of the system 300C, the data storage 315 can maintain one or more skin images of the user. For example, the application 320 may provide, via the network 104, one or more images of a portion of the user's skin in one or more messages. The messages may include a decryption key, or a key that otherwise authorizes the client device 102 to access the data in the data storage 315 that is associated with the user. The data storage 315 can maintain, in one or more data structures in one or more regions of computer memory, the images of the messages transmitted by the application on the client device 102 via the network 104. These images can be accessed by computing devices that are authorized to access the data associated with the user or the client device 102, such as the skin analysis system 120, the other computing devices 360, or other computing devices as described herein.

At least in the context of the system 300C, the data storage 315 can store the results of the classification of user skin colors as the skin color classification 305 or as part of the skin color classification 305. For example, the skin color classification determined by at least the system 300A described herein above in conjunction with FIG. 3A can be maintained in the data storage 315 as the skin color classification 305. The skin color classification 305 can be a numerical quantity that represents a skin tone or skin color of the user, and may be stored in one or more data structures in the data storage 315 in association with other data from the user (e.g., skin images 220, the user records 310, etc.). The skin color classification 305 can be, for example, a Fitzpatrick skin score of the user, and can be stored in association with other data of the user such as the medical records of the user or a user profile. In some implementations, the skin color classification can be stored in association with a respective skin image 220 in the data storage 315.

The data storage 315 can store the user records 310 that include data the user has provided via the application 320. The user records 310 can include information about the user, such as answers to various questions about the user's skin, biometric information, medical records of the user, medical history of the user, diagnoses for the user determined by the skin analysis system 120, and other user information. The user records 310 can include any previous treatment plans that the user has reported to have used (e.g., as located in the medical records of the user, or reported or transmitted from the application 320, etc.). The user records 310 can be stored in one or more data structures and be indexed by a user identifier that corresponds to the user of the mobile device 102. The data storage 315 can be an encrypted and Health Insurance Portability and Accountability Act (HIPAA) compliant data storage module that can maintain encrypted records of user data in association with one or more user identifiers. The, either through the client device 102 or through another computing device or authorization process, may authorize (e.g., distribute access instructions to, provide a private key to, provide a password to, etc.) the encrypted portions of the data storage 315 that are associated with the user. This can allow only computing devices that the user has authorized to access the data in the data storage 315 that is associated with the user. For example, the data in the data storage 315 that is associated with the user pay be encrypted, and may only be decrypted using a private key. To authorize access to the data in the data storage, the user may distribute the private key to other computing systems via the network 104 or another communication process. The user records 310 can store, for example, any skin conditions or characteristics diagnosed or determined by the system 300B described herein above in conjunction with FIG. 3B or the system 300A described herein above in conjunction with FIG. 3A.

The user records 310 can store information about skin conditions, diagnoses, or diseases. Creating a personalized treatment plan for a given skin condition can rely on the most up-to-date information or studies about certain skin conditions or characteristics and their corresponding treatments. To maintain the most up-to-date treatment data, the skin analysis system 120 can query one or more of the other computing devices 360, which can include databases of medical information and treatment information for skin diseases. For example, in response to diagnosing a skin condition based on images and user information received from the mobile device 102, the skin analysis system can query or otherwise access one or more of the other computing devices 360 with a request for treatment data for that skin condition. In response, the other computing devices can transmit information about treatments for the skin disease, such as possible prescriptions, dosage information, or other treatment recommendations, and any associated treatment outcomes (e.g., treatment duration, expected prognosis, expected progress after treating for certain periods of time, etc.). For example, the expected progress of a course treatment can include information about an expected status of skin condition after treating the condition with a particular drug or prescription for predetermined time intervals.

In some implementations, at least one of the other computing devices 360 can provide a message to the skin analysis system 120 including a notification that there is updated information for treatment of a skin condition. In response to receiving the message from the other computing device 360, the skin analysis system 120 can request the updated information for the skin condition, and receive the requested information from at least one of the other computing devices 360 in response to the request. The skin analysis system 120 can store the updated information for a particular treatment in the user records 310 or in another region of memory in the data storage 315.

At least in the context of the system 300C, the client device 102 can maintain and execute at least one application 320. The application 320 can include computer executable instructions, that when executed by the processor of the client device, cause the client device to display at least one user interface (e.g., a graphical user interface, etc.) on a display of the client device 102. The application 320 may present a graphical user interface on a display coupled to a processor of the mobile device 102. The graphical user interface may be, for example, presented in response to executing the application 320. The mobile device 102 may receive the application 320 from one of the computing devices of the cloud 108, or another computing device external to the mobile device 102, or from the skin analysis system 120. The graphical user interface provided by the application 320 can present questions to a user (e.g., in the form of text, graphics, or other display objects, etc.), with appropriate spaces, input boxes, or other means to provide input to the computing device. For example, the user may provide a touch input on a virtual keyboard, or may interact with various actionable objects to make selections of various answers to questions displayed by the application 320.

At least in the context of the system 300C, the application 320 can provide a menu or interface that allows the user to request a treatment plan for a diagnosed skin condition, such as a skin condition diagnosed by skin analysis system 120 of the system 300B as described herein above in conjunction with FIG. 3B. Upon selecting the option to request a treatment plan, the user may be prompted to provide one or more skin images of a diseased portion of skin, or an area of skin that may be of concern to the user. For example, the application 320 may present access a camera (e.g. the camera 325) of the mobile device 102 to request that the user take at least one image of a diseased portion of skin. The application 320 may present instructions to the user about the contents of the one or more image, such as requesting that the user present a reference object having a reference color in the same images as the diseased portion of skin. The application 320 may request that the user take a number of images using the camera. For example, the application 320 may request that the user take five photographs of the skin area of concern. After capturing the images of the potentially diseased area of skin, the application 320 can transmit the images and the user information in one or more messages to the skin analysis system 120, for example as part of a request for a skin diagnosis. In some implementations, the skin analysis system 120 may have already stored images used to diagnose the skin condition (e.g., the skin images 220 of the data store 315, etc.), and therefore does not request that the user provide any additional images. In some implementations, the user need not request a personalized treatment plan for the skin condition, and instead the skin analysis system 120 can perform one or more functions to construct a personalized treatment plan for the user after determining a diagnosis for a skin condition based on the user provided skin images 220.

The client device 102 can include at least one camera 325. The camera may be integrated with the hardware of the client device 102, such as directly coupled to one or more data busses of the processor of the client device 102. In some implementations, the camera 325 can be coupled to the client device by other means, such as via a universal-serial bus connection or other type of serial or parallel connection. The camera 325 can capture light and produce one or more images. The applications or the operating system executing on the client device 102, such as the application 320, can access the camera 325 to capture one or more images. For example, the application 320 can capture one or more images using the camera and store them in the memory of the client device 102. The images can be captured in a variety of formats, for example a Joint Photographic Experts Group (JPEG) image, a portable network graphics (PNG) image, a Graphics Interchange Format (GIF) image, a Tagged Image File (TIFF) image, a Portable Document Format (PDF) image, or a RAW image format. After capturing one or more images, for example of a healthy portion of skin of the user or a diseased portion of skin of the user, the application 320 can transmit the images, and any other user information gathered by the application 320, to the image receiver 330 of the skin analysis system 120. By way of non-limiting example, the camera may be one of a smart phone, an external camera, a webcam, or external device coupled to the data processing system via a network At least in the context of the system 300C, the image receiver 330 can receive one or more images of skin of the user from the camera 325 (e.g., via the application 320, etc.) of the client device 102. The skin can have a skin color. In some implementations, the application may prompt the user to include at least one reference object with a known color in the photo of skin. An example reference object can be, for example, a new United States dollar bill. In some implementations, the application 320 can transmit a request for a skin diagnosis classification to the image receiver 330. In such implementations, the image receiver 330 can receive the request for a skin diagnosis classification (e.g., a disease, status, or characteristic, etc.), which can include the one or more images of the skin of the user. The request for a skin diagnosis can include other information about the user, such as the answers to the questions, any user profile information described herein, or any information received from the user by the application 320 as described in this technical solution. Upon receiving the one or more images of the skin and the user information, the image receiver 330 can store the images, for example, as the skin images 220 or as a part of the skin images 220. For example, if a region of memory in the data storage 315 already exists, the image receiver 330 can update the skin images 220 to include the images received from the application 320. In some implementations, skin images for the diseased areas of skin are extant in the data storage 315, and the image receiver 330 can access and retrieve the skin images 220 from the data storage 315 that are associated with the diagnosed skin condition or case.

The medical record accessor 392 can access medical information of the user received from the mobile device 102, stored in the user records 310, or accessed via at least one of the other computing devices 360. The medical record information can include the answers to any of the questions presented to the user via the application 320 as described herein. The medical record information can include any diagnoses or characteristics of the user that is determined by the skin analysis system 120, such as a diagnosis of a skin condition for a particular case, image, or set of images provided by the user. The medical information can include biometric information, such as a reported skin color of the user, a natural hair color of the user, an eye color of the user, a reported likelihood of burning in the sun my the user, the height of the user, the weight of the user, or any other biometric information as described herein. The medical record accessor 392 can query one or other computing devices 360, such as those that are associated with a previous healthcare provider of the user associated with the skin condition, with at least one request for medical records or other information. The medical record information can include information about the skin condition for which a personalized treatment plan is to be created, such as the duration, severity, and type of diagnosis, characteristics, or other information. The medical records or medical information can include previous treatments attempted by the user, other treatment data, drugs the user has taken or currently takes, or any other medically relevant information. Accessing the medical information can include retrieving other information as needed by the treatment plan determiner to determine a personalized treatment plan of the user. Any such information can be accessed by the medical record accessor 392 via the network 104, the other computing devices 360, the mobile device 102, or the data storage 315.

The medical information accessor 392 can numerically encode the medical information such that it can be provided as an input to a machine learning model. For example, each medically relevant information item can represent a position in a data structure. In a non-limiting example explanation, this data structure can be a vector with one or more coordinates. However, it should be understood that the data structure that encodes the medical information need not be limited to a vector, and may take the form of other data structures, such as a matrix, a tensor, or other data structure suitable for use with a machine learning model (e.g., dense neural network, recurrent neural network, convolutional neural network, sparse vector machine, linear regression, etc.). Encoding the medical information can include, for example, assigning each position in the data structure a portion of medical information (e.g., one position for eye color, another for hair color, one for duration of skin condition, another for a type of pre-existing condition, etc.). Each of the possible values for the medical information can be assigned a numerical value (e.g. "blue eyes" can be assigned the number 1, "brown eyes" can be assigned the number 2, etc.). The data structure can then be populated according to the information accessed by the medical record accessor 392, and the data structure can be subsequently stored in association with the user profile in the user records 310. In a non-limiting example explanation, consider a data structure vector with only two positions: one for duration of skin condition, and another for a location of the skin condition. If the medical record accessor 392 determines an eye color of blue, and a location of the skin condition is on the neck, and the numerical assignment for blue eyes is 4 and the numerical assignment for the neck location is 19, the medical record accessor 392 can generate a data structure as: [4, 19]. Although this non-limiting example has described the data structure representing the medical information has having only two positions, it should be understood that the data structure can have any number of positions, numerical codes, and parameters.

The treatment plan determiner 394 can provide the data structures that represent the medical information and the diagnosis information as an input layer to a treatment determination model. The treatment determination model can be a neural network that is trained to take, as input, one more data structures that represent a skin diagnosis and user medical information to determine a set of output probabilities corresponding to a respective set of possible treatment plans. The output probabilities can be confidence scores representing a likelihood of a positive treatment outcome. Providing the data structures as an input layer can include normalizing (e.g., scaling the values of the data structures such that their coordinate values are floating point values each between zero and one, etc.). After providing the data structures as input to the skin treatment determination model, the treatment plan determiner 392 can propagate (e.g., perform the mathematical computations of each layer, etc.) the input data through the treatment determination model until a set of output probabilities corresponding to a respective set of treatment plans are output at an output layer. The skin treatment plan determiner can receive the output data structure from the treatment determination module, which can be provided to the treatment plan selector 396 for additional processing.

The treatment plan selector 396 can receive a data structure from the treatment plan determiner 394 or the trained treatment determination model that includes a set of output probabilities corresponding to a respective set of treatment plans for a particular skin condition. The probabilities can correspond to the likelihood of a given treatment for the skin condition given the medical information of the user. The data structure can be a vector that includes a number of coordinates, where each coordinate in the vector can be a probability value, such as a probability value that is between zero and one. A probability close to or equal to zero can represent a low likelihood that the corresponding treatment plan will work for the user and the skin condition, and a probability close to or equal to one can represent a high likelihood that the corresponding treatment plan will work for the user and the skin condition. The treatment plan selector 396 can select one or more of the positions in the data structure, and the respective diagnosis associated therewith, based on its corresponding probability value. For example, the treatment plan selector 396 can compare each of the probability values in the data structure to a predetermined probability threshold. If the probability of a particular position or data entry in the data structure is greater than or equal to the threshold, the treatment plan selector 396 can select the treatment plan associated with that position in the data structure as the personalized treatment plan for the skin condition of the user. The treatment plan selector 396 can repeat this process for each position in the data structure to select a set of personalized treatment plans. In some implementations, the treatment plan selector 396 can sort the positions in the data structure to create a sorted data structure. In such implementations, the treatment plan selector 396 can select a predetermined number of treatment plans (e.g., top five, top ten, etc.) in the data structure that have the greatest value or probability. Of a selected set of treatment plans, the treatment plan selector 396 can select the treatment plan associated with the highest probability of success for the user (e.g., the highest probability in the data structure, etc.). The treatment plans can include a description of the treatment plan, the course of the treatment plan, the duration of the treatment plan, one or more prescriptions, instructions for applying the prescriptions, instructions to the user to perform one or more actions to treat the skin condition, or any other information about skin disease treatment.

The treatment plan provider 398 can provide the treatment or characteristics to the application 320 executing on the mobile device 102. For example, the treatment plan provider 398 may transmit a message (e.g., which may be a response message to the request for classification, etc.) to the application 320 of the mobile device 102 via the network 104. The message can include, the classification of the one or more diagnoses (e.g., a type of acne, cancer, type rash, dry skin, etc.), a probability value associated with each diagnosis or characteristic, and any other information about the skin diagnosis or characteristics, such as a description of the diagnosis or characteristic. The message can include the personalized treatment plan, including a description of the treatment plan, the course of the treatment plan, the duration of the treatment plan, one or more prescriptions, instructions for applying the prescriptions, instructions to the user to perform one or more actions to treat the skin condition, or any other information about skin disease treatment.

The message can include instructions to display the personalized treatment plan for the skin condition, including a description of the treatment plan, the course of the treatment plan, the duration of the treatment plan, one or more prescriptions, instructions for applying the prescriptions, instructions to the user to perform one or more actions to treat the skin condition, or any other information about skin disease treatment, on the display of the mobile device 102 (e.g., in the application 320, etc.). In some implementations, the skin characteristic provider 380 can store the personalized skin condition for the user in association with one or more user records 310, such as medical records, the user profile, the images of the diseased skin 220, or other user information in the data storage 315 of the skin analysis system 120. The treatment plan provider 398 can transmit or otherwise provide the personalized treatment plan for the skin condition to one or more computing devices of a healthcare professional that is associated with the user (e.g., at least one of the other computing devices 360).

In addition, the skin analysis system 120 can determine a treatment progress of the skin condition detected in the image by comparing detected characteristics of the skin condition in the image with characteristics detected from an image captured at a later time. For example, the user can provide one or more additional images once the treatment plan has progressed over a period of time. In some implementations, the skin analysis system 120 can request additional images of a skin condition from a user, for example, in response to a message from a medical provider computing device, or in response to a predetermined or configured period of time elapsing. The skin characteristics of the skin condition, as depicted in the image, can be analyzed over time using the artificial intelligence models described herein. As indicated, these characteristics (e.g., including severity of any detected skin condition) can be numerically encoded, such that the values of severity can be easily compared.

The skin analysis system 120 can then track the severity values of the skin condition over time, for example, by iteratively comparing the severity values of the skin condition with historic severity values calculated using the artificial intelligence models described herein. From the change in severity values of the skin condition, the skin analysis system 120 can determine a treatment progress of the skin condition, for example, as the recommended treatment is applied to the skin condition over time. The skin analysis system 120 can therefore recommend treatment plans to treat skin conditions detected using artificial intelligence, and likewise track the progress and efficacy of the treatment plan overtime for each user. If, for example, the tracked progress of the treatment plan does not conform to an expected progress (e.g., an expected decrease in severity over a predetermined amount of time, etc.), the skin analysis system 120 may recommend a different treatment plan for the skin condition. For example, if the skin analysis system 120 determines that the severity of a skin condition has remained relatively constant, or gotten worse (e.g., allergic reaction, ineffective treatment for individual, etc.), the skin analysis system 120 can select a second treatment plan for the skin condition as described herein, and store the overall treatment progress for the skin condition in the medical record of the user. The skin analysis system 120 can transmit the treatment progress to the mobile device 102 of the user.

Figure 4:
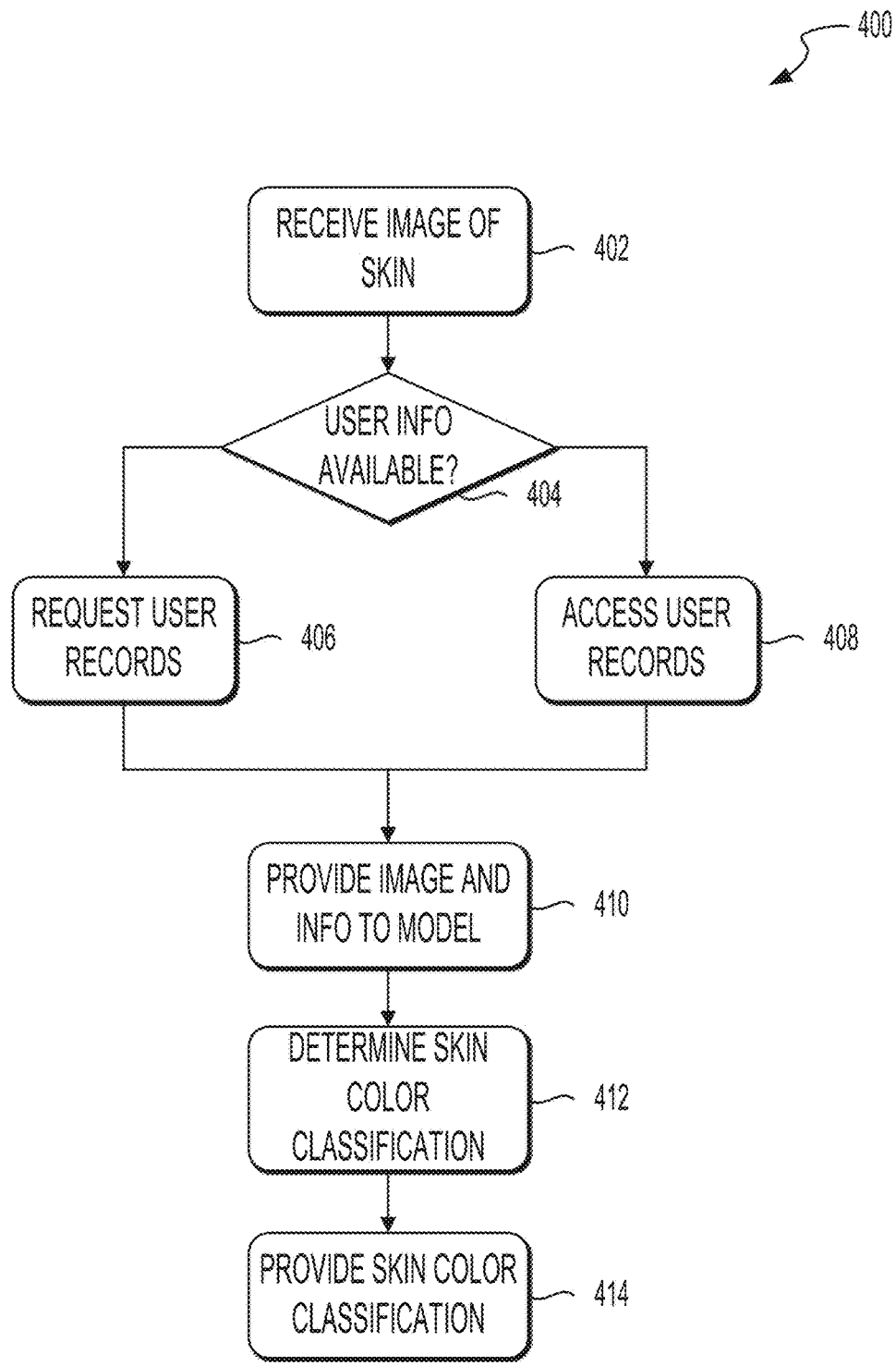
FIG. 4 illustrates an example flow diagram of a method of determining a numerical classification of human skin color.

Referring now to FIG. 4, depicted is an illustrative flow diagram of a method 400 for determining a numerical classification of human skin color. The method 400 can be executed, performed, or otherwise carried out by the skin analysis system 120, the computer system 100 described herein in conjunction with FIG. 1A-1D, or any other computing devices described herein. The method 400 can include any of the steps of method 500 described herein in conjunction with FIG. 5 or any of the steps of method 600 described herein in conjunction with FIG. 6. The skin analysis system (e.g., the skin analysis system 120, etc.) can receive, from a camera, an image captured of a portion of skin having a skin color (STEP 402). The skin analysis system can determine whether user information (e.g. biometric information, user records such as the user records 320, etc.) is available (STEP 404). The skin analysis system can request one or more user records or other user information from the mobile device (e.g., the mobile device 102) of the user (STEP 406). The skin analysis system can access biometric information or user records of the user from a mobile device of the user (STEP 408). The skin analysis system can provide the image and the biometric information as input to a skin color classification module (e.g., the skin color classification module 350, etc.) (STEP 410). The skin analysis system can determine a classification of a skin color of the user based on the output of the skin color classification module (STEP 412). The skin analysis system can provide the classification of the skin color of the user to the mobile device (STEP 414).

The skin analysis system can receive, from a camera, an image captured of a portion of skin having a skin color (STEP 402). In some implementations, the application (e.g., the application 320, etc.) executing on the mobile device may prompt the user to include at least one reference object with a known color in the photo of skin. An example reference object can be, for example, a new United States dollar bill. In some implementations, the application can transmit a request for a skin score color classification to the skin analysis system. In such implementations, the skin analysis system can receive the request for a skin color classification (e.g., the skin score or skin color value, etc.), which can include the one or more images of the skin of the user. Upon receiving the one or more images of the skin, the skin analysis system can store the images in the memory of the skin analysis system. In some implementations the skin analysis system can receive one or more answers to questions, such as the answers to the various skin related questions provided by the user via the application described herein above. The answers and the questions can be transmitted by the application with the skin images (e.g., stored as the skin images 220, etc.), and can be stored by the skin analysis system as part of the user records or a user profile (e.g., the user records 310, etc.). In some implementations, if a user profile is indicated in one or more messages received from the application (e.g., the messages including the images, answers to the questions, or other biometric information, etc.), the skin analysis system can store the data in the messages received from the application in the data storage of the skin analysis system in association with the user profile.

The skin analysis system can determine whether user information (e.g. biometric information, user records such as the user records 320, etc.) is available (STEP 404). For example, the skin analysis system can determine whether the user has provided answers to one or more biometric questions, such as those detailed herein above in conjunction with FIGS. 3A-3C. In some implementations, the skin analysis system can determine whether the user has stored any information, such as a user profile or user records (e.g., the user records 310, etc.) in the memory or the data storage (e.g., the data storage 315, etc.) of the skin analysis system. If the user has not yet provided biometric information or user records, the skin analysis system can perform STEP 406 of the method 400. If the user has provided biometric information or user records, the skin analysis system can perform STEP 408 of the method 400.

The skin analysis system can request one or more user records or other user information from the mobile device (e.g., the mobile device 102) of the user (STEP 406). In particular, the skin analysis system can provide or present the user with one or more questions by sending instructions to the application executing on the mobile device. The instructions can be transmitted via a network to the mobile device of the user as part of a request for biometric information or user records or user information. The questions, biometric information, or requests for user information can be any of those described herein above in conjunction with FIG. 2, 3A, 3B, or 3C, or any combination thereof. The skin analysis system can access biometric information of the user received from the mobile device in response to any such requests. The biometric information can include the answers to any of the questions presented to the user via the application executing in the mobile device as described herein above. The biometric information can include, for example, a reported skin color of the user, a natural hair color of the user, an eye color of the user, a reported likelihood of burning in the sun my the user, the height of the user, the weight of the user, or any other biometric information as described herein.

The skin analysis system can access biometric information or user records of the user from a mobile device of the user (STEP 408). The skin analysis system can access the biometric information or user records of the user by accessing one or more regions of a data store that maintains said information. In some implementations, this information may be encrypted, and may require a passkey, private key, or other means to decrypt the data stored therein. In some implementations, the skin analysis system can request authorization to access said information from the mobile device, and receive a response including a decryption key, passkey, or other means to decrypt the data in response. Upon decrypting the data, the skin analysis system can retrieve any data necessary to accurately determine a classification of the skin color of the user. The questions, biometric information, or requests for user information can be any of those described herein above in conjunction with FIG. 2, 3A, 3B, or 3C, or any combination thereof. The skin analysis system can access biometric information of the user received from the mobile device in response to any such requests. The biometric information can include the answers to any of the questions presented to the user via the application executing in the mobile device as described herein above. The biometric information can include, for example, a reported skin color of the user, a natural hair color of the user, an eye color of the user, a reported likelihood of burning in the sun my the user, the height of the user, the weight of the user, or any other biometric information as described herein.

The skin analysis system can provide the image and the biometric information as input to a skin color classification module (e.g., the skin color classification module 350, etc.) (STEP 410). The skin color classification module can be a part of the skin analysis system. The skin analysis system can numerically encode the biometric information such that it can be provided as an input to a machine learning model. For example, each question or item of user information may represent a position or memory location in a data structure. In a non-limiting example explanation, this data structure could be a vector with one or more coordinates. However, it should be understood that the data structure that embodies the encoded biometric information need not be limited to a vector, and may take the form of other data structures, such as a matrix, a tensor, or another data structure suitable for use with a machine learning model (e.g., dense neural network, recurrent neural network, convolutional neural network, sparse vector machine, linear regression, etc.). Encoding the biometric information can include, for example, assigning each position in the data structure a portion of biometric information (e.g., one position for eye color, another for hair color, another for the first question, another for the second question, etc.). Each of the possible values for a respective portion of the biometric information can be assigned a numerical value (e.g. "blue eyes" can be assigned the number 1, "brown eyes" can be assigned the number 2, etc.). The data structure can then be populated according to the biometric information that is associated with the user, and the data structure can be subsequently stored in association with the user profile in the memory of the skin analysis system. In a non-limiting example explanation, consider a data structure vector with only two positions: one for eye color, and another for hair color. If the user reports, using the application of the mobile device, an eye color of blue, and a hair color of brown, and the numerical assignment for blue eyes is 1 and the numerical assignment for brown hair is 3, the skin analysis system can generate an encoded data structure of: [1, 3]. Although this non-limiting example has described the biometric information has having only two positions, it should be understood that the data structure can have any number of positions, numerical codes, and parameters.

The skin analysis system can format one or more images (e.g., the skin images received from the application, etc.) such that they can be used as input to the skin color classification module. Formatting an image can include, for example, adjusting the colors in the image based on a reference color. When an image is captured by the application executing on the mobile device, the user of the mobile device 102 can be instructed to include a reference object with a known color in the photograph.

Because the reference color is known by the skin analysis system and will generally not change, the color can be used as a normalization color (e.g., a color from which the other colors in the image are compared and compensated). The colors in the image can be adjusted based on a color in the image that is closest to the reference color. Images captured by mobile devices, such as the mobile device of the user, can be captured in a variety of different lighting environments. To compensate for the differences in lighting in the image, the skin analysis system can identify a color (e.g., a red-green-blue (RGB) pixel value, etc.) in the image that is closest to the reference color (e.g., a group of adjacent pixels with an average color that is within a predetermined threshold of the reference color, etc.), and determine a difference between the actual reference color (e.g., via subtraction, etc.). Upon determining the difference, the skin analysis system can adjust (e.g., change, modify, etc.) the other colors in the image by adding or subtracting, as the case may be, the compensation value to each of the RGB pixel values the image to generate a compensated image, which can be used in further processing steps and ultimately used as input to the skin color classification module. In some implementations, the image may not include a reference color (or the user may not have been instructed to include a reference color, etc.). In such implementations, the skin analysis system can proceed with further processing steps without compensating for differences in the color or lighting of the image.

To format the image as input to the model, the skin analysis system can construct one or more data structures that represent the image. For example, the skin analysis system can extract a pixel value for each pixel in the image. In some implementations, the image may be down scaled to a fixed resolution prior to extracting the pixel values (e.g., to 128×128, 256×256, 512×512, or 1024×1024 pixels, etc.). Extracting the pixel values can include identifying an RGB value for each pixel, and placing it into a corresponding position in the generated data structure. As such, each position in the data structure can have, for example, a three coordinate vector where each position in the vector corresponds to one of a red, green, and blue intensity of the respective pixel in the image. In some implementations, the skin analysis system can average the blue, red, and green values of each pixel together to generate a grayscale image prior to extracting the pixel values to populate the data structure. In such implementations, the data structure generated using the grayscale image can have one coordinate per pixel. In some implementations, the skin analysis system can normalize the data structure that represents the image prior to providing it as input to the skin color classification module.

After pre-processing the image, the skin analysis system can provide the data structure that represents the image or the data structure that represents the biometric information as the input layer to the skin color classification module. Providing the data structures as an input layer can include normalizing (e.g., scaling the values of the data structures such that their coordinate values are floating point values each between zero and one, etc.).

The skin analysis system can determine a classification of a skin color of the user based on the output of the skin color classification module (STEP 412). After providing the data structures as input to the skin color classification module, the skin analysis system can propagate (e.g., perform the mathematical computations of each layer, etc.) the data of the input layer through the skin color classification module until the skin classification module produces an output value that is representative of a classification of the skin color. For example, in the case where the skin classification module is trained to determine a Fitzpatrick skin score, the output value can be a value between 1 and 6. In the case of the Fitzpatrick skin score, a value of 1 can refer to skin that is very pale, and a value of 6 can refer to skin that is very dark.

In some implementations, the skin analysis system can receive more than one skin color classification output values from the skin color classification module (e.g., as a series of classification values in an output vector or other output data structure, etc.). In such implementations, the skin color classifier can select a skin color classification from the on one or color classification output values having a value greater than another of the plurality of skin color classification output values. In a non-limiting example implementation, the output vector of the skin color classification module can have six positions, with each position corresponding to a respective one of the six Fitzpatrick skin score values. The skin color classification module can output a confidence score (e.g., floating point value between zero and one, etc.) at each position, and the skin analysis system can select whichever position has the highest confidence score. Thus, if the output vector is [0.1, 0.5, 0.3, 0.04, 0.06, 0.0], and the leftmost value represents a Fitzpatrick skin score of 1 and the rightmost value represents a Fitzpatrick skin score of 6, the skin color classifier can determine the Fitzpatrick skin score of 2 as the classification of the skin color of the user The skin analysis system can provide the classification of the skin color of the user to the mobile device (STEP 414). For example, the skin analysis system may transmit a message (e.g., which may be a response message to the request for classification received from the mobile device, etc.) to the application executing on the mobile device via a network (e.g., the network 104, etc.). The message can include the classification of the skin score of the user (e.g., the Fitzpatrick skin score, etc.), and may include instructions to display the classification of the skin score on the display of the mobile device of the user. In some implementations, the skin analysis system can store the skin score for the user in association with one or more user records, such as medical records, a user profile, or other user information in the data storage of the skin analysis system.

Figure 5:
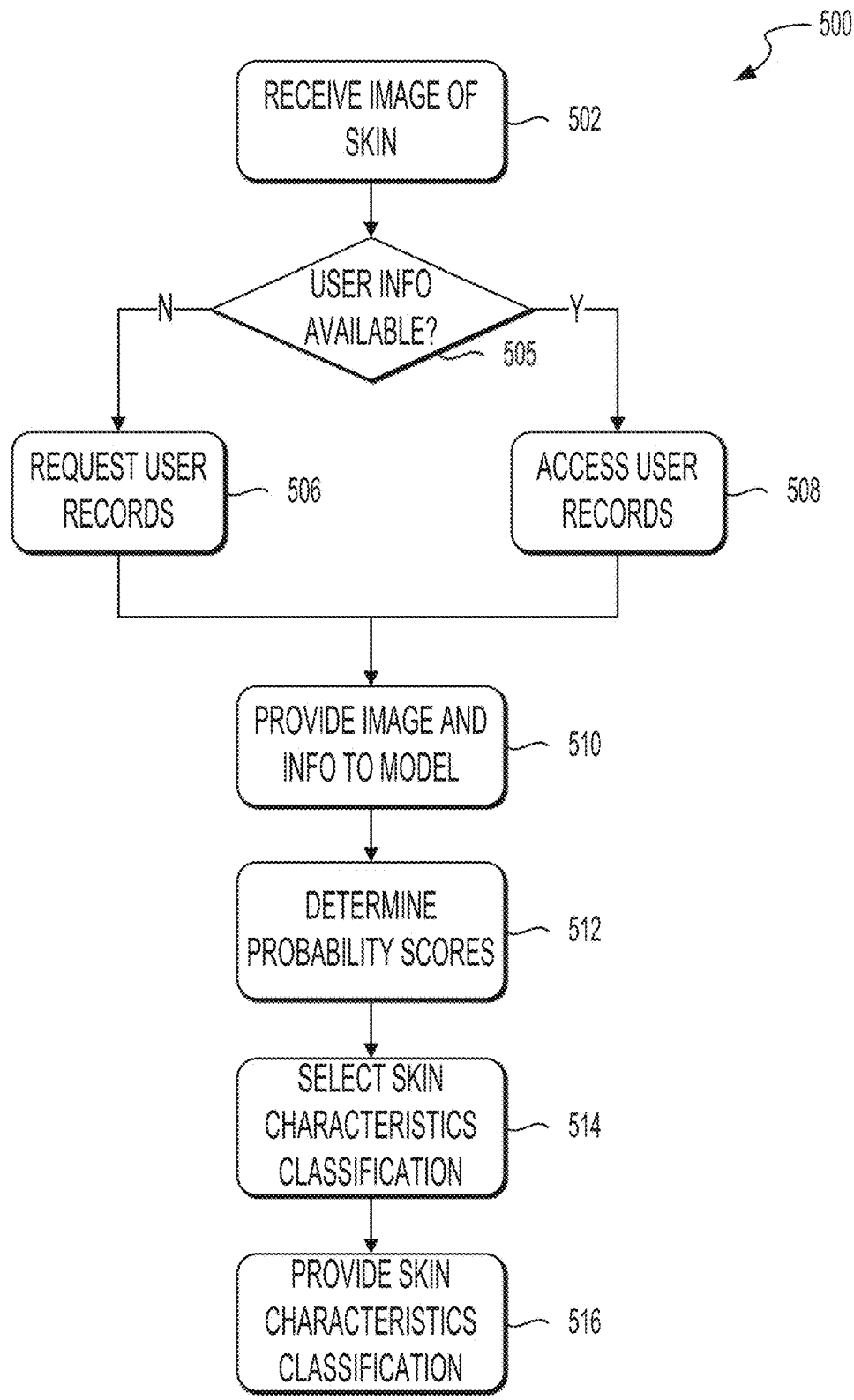
FIG. 5 illustrates an example flow diagram of a method of identifying or determining one or more characteristics of human skin.

Referring now to FIG. 5, depicted is an illustrative flow diagram of a method 500 for determining one or more characteristics of skin present in an image. The method 500 can be executed, performed, or otherwise carried out by the skin analysis system 120, the computer system 100 described herein in conjunction with FIG. 1A-1D, or any other computing devices described herein. The method 500 can include any of the steps of method 400 described herein in conjunction with FIG. 4 or any of the steps of method 600 described herein in conjunction with FIG. 6. The skin analysis system (e.g., the skin analysis system 120, etc.) can receive, from a camera, one or more images captured of a portion of skin having a potential skin condition (STEP 502). The skin analysis system can determine whether user information (e.g. biometric information, user records such as the user records 320, etc.) is available (STEP 504). The skin analysis system can request one or more user records or other user information from the mobile device (e.g., the mobile device 102) of the user (STEP 506). The skin analysis system can access user information or user records of the user from a mobile device of the user (STEP 508). The skin analysis system can provide the image and the biometric information as input to a skin characteristic determination module (e.g., the skin characteristic determination module 385, etc.) (STEP 510). The skin analysis system can determine one or more probability scores of characteristics of the skin represented in the images based on the output of the skin characteristics determination module (STEP 512). The skin analysis system can select one or more of skin characteristics based on the probability scores (STEP 514). The skin analysis system can provide the one or more skin characteristics of the skin represented in the images to the mobile device (STEP 516).

The skin analysis system (e.g., the skin analysis system 120, etc.) can receive, from a camera, one or more images captured of a portion of skin having a potential skin condition (STEP 502). In some implementations, an application (e.g., the application 320) executing on the mobile device (e.g., the mobile device 102) may prompt the user to include at least one reference object with a known color in the photo of skin. An example reference object can be, for example, a new United States dollar bill. In some implementations, the application can transmit a request for a skin diagnosis classification to the image receiver 330. The skin analysis system can receive the request for a skin diagnosis classification (e.g., a disease, status, or characteristic, etc.), which can include the one or more images of the skin of the user. The request for a skin diagnosis can include other information about the user, such as the answers to questions provided the application, such as questions relating to the area of skin, any user profile information described herein, or any information received from the user by the application 320 as described in this technical solution. In some implementations, the request can include data that points to one or more medical records of the user. Upon receiving the one or more images of the skin and the user information, the skin analysis system can store the images, for example, in one or more data structures in the memory of the skin analysis system.

The skin analysis system can determine whether user information (e.g. biometric information, user records such as the user records 310, medical records of the user, historical treatment data of the user, etc.) is available (STEP 504). For example, the skin analysis system can determine whether the user has provided answers to one or more biometric questions, medical history questions, answers relating to a potential skin condition (e.g., duration of condition, burning sensation, itching, etc.) such as those detailed herein above in conjunction with FIGS. 3A-3C. In some implementations, the skin analysis system can determine whether the user has stored or provided any information, such as a user profile or user records (e.g., the user records 310, etc.) in the memory or the data storage (e.g., the data storage 315, etc.) of the skin analysis system. For example, the skin analysis system can access one or more regions of the memory or data storage of the skin analysis system to identify if there is any user information present, such as user profile, or any other user information described herein. If the user has not yet provided user information, medical records, or user records, the skin analysis system can perform STEP 506 of the method 500. If the user has provided biometric information or user records, the skin analysis system can perform STEP 508 of the method 500.

The skin analysis system can request one or more user records or other user information from the mobile device (e.g., the mobile device 102) of the user (STEP 506). The skin analysis system can provide or present the user with one or more questions by sending instructions to the application executing on the mobile device. The instructions can be transmitted via a network to the mobile device of the user as part of a request for biometric information, user medical records or user records or user information. The questions, user information, or requests for user information can be any of those described herein above in conjunction with FIG. 2, 3A, 3B, or 3C, or any combination thereof. The skin analysis system can access the user information received from the mobile device in response to any such requests. The user information can include the answers to any of the questions presented to the user via the application executing in the mobile device as described herein above. The user information can include, for example, biometric information of the user, previous or current skin conditions or other previous or current medical conditions of the user, drugs taken by the user, other clinically relevant information, or any other user information as described herein.

The skin analysis system can access user information or user records of the user from a mobile device of the user (STEP 508). The skin analysis system can access the user information or user records by accessing one or more regions of a data store that maintains said information. In some implementations, this information may be encrypted, and may require a passkey, private key, or other means to decrypt and subsequently access the data stored therein. In some implementations, the skin analysis system can request authorization to access said information from the mobile device, and receive a response including a decryption key, passkey, or other means to decrypt the data in response. Upon decrypting the user information data (e.g., the user records, user medical information, etc.), the skin analysis system can retrieve any data necessary to accurately determine one or more characteristics of the skin present in images provided by the application executing on the mobile device of the user. The user information or requests for user information can be any of those described herein above in conjunction with FIG. 2, 3A, 3B, or 3C, or any combination thereof. The skin analysis system can access user information received from the mobile device in response to any such requests. The user information can include the answers to any of the questions presented to the user via the application executing in the mobile device as described herein above. The user information can include, for example, biometric information of the user, previous or current skin conditions or other previous or current medical conditions of the user, drugs taken by the user, the duration of the skin condition, any other clinically relevant information, or any other user information as described herein The skin analysis system can provide one or more images and the user information as input to a skin characteristic determination module (e.g., the skin characteristic determination module 385, etc.) (STEP 510). To do so, the skin analysis system can numerically encode the biometric information and other medically relevant user information such that it can be provided as an input to a machine learning model (e.g., the skin characteristic determination module 385, etc.). For example, each portion of medically relevant information may represent a position in a data structure. In a non-limiting example explanation, this data structure could be a vector with one or more coordinates. However, it should be understood that the data structure that encodes the biometric information need not be limited to a vector, and may take the form of the data structures, such as a matrix, a tensor, or other data structure suitable for use with a machine learning model (e.g., dense neural network, recurrent neural network, convolutional neural network, sparse vector machine, linear regression, etc.). Encoding the user information can include, for example, assigning each position in the data structure a portion of user information (e.g., one position for duration of skin condition, another for a whether the condition is itchy, or any other information associated with the user as described herein, etc.). Each of the possible values for the user information can be assigned a numerical value (e.g. a yes/no question can be assigned a binary zero or a binary one, number of days can be assigned the number of days the user has had the condition, a particular code if a user is currently using a drug, etc.). The data structure can then be populated according to the user information that is provided by the user or gathered from any other source as described herein, and the data structure can be subsequently stored in association with the user profile in the memory of the skin analysis system. In a non-limiting example explanation, consider a data structure vector with only two positions: one for duration of condition, and another for burning sensation. If the user reports, using the application executing on the mobile device, that the potential skin condition has been present for 7 days, and that the condition includes a burning sensation, the skin characteristic determiner 370 can generate a data structure as: [7, 1]. Although this non-limiting example has described the user information has having only two positions or portions, it should be understood that the data structure can have any number of positions, numerical codes, and parameters based on the amount of user provided information or the size of the input layer of the skin characteristic determination module.

The skin analysis system can format one or more images (e.g., the skin images received from the application on the mobile device, etc.) such that they can be used as input to the skin characteristic determination module. Formatting an image can include, for example, adjusting the colors in the image based on a reference color, adjusting the color of the image to grayscale, downscaling or upscaling the images to predetermined resolutions, cropping the image to an identified area of interest, or any combination thereof. When an image is captured by application executing on the mobile device, the user of the mobile device can be instructed (e.g., via text presented in the user interface of the application) to include a reference object with a known color in the image.

Because the reference color is known and will generally not change, the color can be used as a normalization color (e.g., a color from which the other colors in the image are compared and compensated). Further, the colors in the image can be adjusted based on a color in the image that is closest to the reference color. Images captured by mobile devices may be captured in a variety of different lighting environments. To compensate for the differences in lighting in the images, the skin analysis system can identify a color in the image (e.g., a group of adjacent pixels with an average color that is within a predetermined threshold of the reference color, etc.) that is closest to the reference color (e.g., an RGB pixel value, etc.), and determine a difference between the actual reference color (e.g., via subtraction, etc.). Upon determining the difference, the skin analysis system can adjust (e.g., change, modify, etc.) the colors in the image by adding or subtracting, as the case may be, the compensation value to each of the RGB pixel values the image to generate a compensated image, which can be used in further processing steps and ultimately used as input to the skin analysis system. In some implementations, the image may not include a reference color (or the user may not have been instructed to include a reference object having a reference color, etc.). In such implementations, the system can proceed with further processing steps without compensating for differences in the color or lighting of the image.

To format the image as input to the model, the skin characteristic determiner 370 can construct one or more data structures that represent the image. For example, the skin analysis system can extract a pixel value for each pixel in the image. In some implementations, the image may be down scaled to a fixed resolution prior to extracting the pixel values (e.g., to 128×128, 256×256, 512×512, or 1024×1024 pixels, etc.). Extracting the pixel values can include identifying an RGB value for each pixel, and placing it into a corresponding position in the generated data structure. As such, each position in the data structure can have, for example, a three coordinate vector where each position in the vector corresponds to one of a red, green, and blue intensity of the respective pixel in the image. In some implementations, the skin analysis system can average (e.g., weighted average, etc.) the blue, red, and green values of each pixel together to generate a grayscale image prior to extracting the pixel values to populate the data structure. In such implementations, the data structure generated using the grayscale image can have one coordinate per pixel. In some implementations, the skin analysis system can normalize the data structure that represents the image prior to providing it as input to the skin analysis system. In some implementations, the skin analysis system can perform each of these steps for all of the images in a request for a diagnosis received from the mobile device.

To determine a set of output probabilities corresponding to a respective set of possible diagnoses of the diseased skin in the images, the skin analysis system can provide the data structure that represents the images or the data structure that represents the user information as the input layer to a skin characteristic determination module (e.g., the skin characteristic determination module 385, etc.). Providing the data structures as an input layer can include normalizing (e.g., scaling the values of the data structures such that their coordinate values are floating point values each between zero and one, etc.). After providing the data structures as input to the skin characteristic determination module, the skin analysis system can propagate (e.g., perform the mathematical computations of each layer, etc.) the data through the skin characteristic determination module until the skin characteristic determination module produces a set of output probabilities corresponding to a respective set of possible diagnoses of the diseased skin in the images. In some implementations, the skin analysis system can input the data structures representing each image processed above one at a time. For example, certain neural networks, such as long-short term memory networks or recurrent neural networks, can provide an output in response to a series of data inputs. Accordingly, the skin analysis system can input each of the data structures of the processed images (e.g., along with the data structure representing the user information held constant, etc.), into the skin characteristic determination module in a series (e.g., one after another).

The skin analysis system can determine one or more probability scores of characteristics of the skin represented in the images based on the output of the skin characteristics determination module (STEP 512). The skin characteristic determination module can be, for example, a recurrent neural network that is configured to accept one or more data structures that are representative of images or of encoded biometric information. The skin characteristic determination module can be a long-short term memory neural network classifier or a gated neural network classifier that is capable of producing an output vector that represents the probabilities of possible skin diagnoses present in images (e.g., an array of probabilities where each position in the array corresponds to a skin condition, disease, diagnoses, or characteristic, etc.). The skin characteristics determination module can be implemented by the skin analysis system.

The skin characteristic determination module can take as an input layer the image data and numerically coded user information. This data can be configured as an input vector, matrix, or tensor that is commensurate with the structure of the skin characteristic determination module input layer. In some implementations, such as a long-short-term memory implementation, the input layer of the skin characteristic determination module 385 can take a series of images as input (e.g., one after another with the user information data structure held constant, etc.). The gated neural network or the long-short term memory network of the skin color classification module can include several layers of gates, which can feed into a dense or fully connected neural network layer. The output of the densely connected layer or layers can be provided as input into one or activation modules, which can include applying (e.g., performing one or more functions on, etc.) activation functions to the data. The activation functions may include, for example, an identity function, a binary step function, a logistic or sigmoid function, a tan h function, an arctan function, a rectified linear unit (ReLu) function, a leaky ReLu function, or a soft-max function, among others. The output of the activation layer can be provided directly as an output layer, and can a data structure, such as a vector, that has one or more coordinates that each represent a skin diagnosis, condition, or characteristic. The values of each coordinate can be output as a probability of the skin in the images input to the skin characteristic determination module being afflicted with the corresponding condition or characteristic. The output layer of the skin characteristic determination module can be provided to or used by the skin analysis system for further processing.

The skin analysis system can select one or more of skin characteristics based on the probability scores (STEP 514). The skin analysis system can utilize the data structure from the skin characteristics determination module that includes a set of output probabilities corresponding to a respective set of possible diagnoses of the diseased skin in the images. For example, the data structure can be a vector that includes a number of coordinates. Each coordinate in the vector can be a probability value, such as a probability value that is between zero and one, where zero represents a low likelihood that the skin is afflicted with the respective diagnosis, and where one represents a high likelihood that the skin is afflicted with the respective diagnosis. The skin analysis system can select one or more of the positions in the data structure, and the respective diagnosis associated therewith, based on its corresponding probability value. For example, the skin analysis system can compare each of the probability values in the data structure to a predetermined probability threshold. If the probability of a particular position or data entry in the data structure is greater than or equal to the threshold, the skin analysis system can select the diagnosis associated with that position in the data structure as a likely diagnosis. The skin analysis system can repeat this process for each position in the data structure to select a set of likely diagnoses. In some implementations, the skin analysis system can sort the positions in the data structure to create a sorted data structure. In such implementations, the skin analysis system can select a predetermined number of diagnoses (e.g., top five, top ten, etc.) in the data structure that have the greatest value or probability. The skin diagnoses may include, for example, an acne diagnosis, a cancer diagnosis, a diagnosis of a type of rash, or any other type of skin diagnosis or characteristic (e.g., dry skin, etc.). The skin characteristics can include a diagnosis of a skin condition.

The skin analysis system can provide the one or more skin characteristics of the skin represented in the images to the mobile device (STEP 516). For example, the skin analysis system may transmit a message (e.g., which may be a response message to the request for classification, etc.) to the application executing on the mobile device via a network (e.g., the network 104, etc.). The message can include, the classification of the one or more diagnoses (e.g., a type of acne, cancer, type rash, dry skin, etc.), a probability value associated with each diagnosis or characteristic, and any other information about the skin diagnosis or characteristics, such as a description of the diagnosis or characteristic. The message can include instructions to display the classification of the one or more diagnoses, characteristics, probabilities, or description, on the display of the mobile device. In some implementations, the skin analysis system can store the one or more skin characteristics or diagnoses of the skin in association with one or more user records, such as medical records, a user profile, the images of the diseased skin, or other user information in the data storage or the memory of the skin analysis system.

Figure 6:
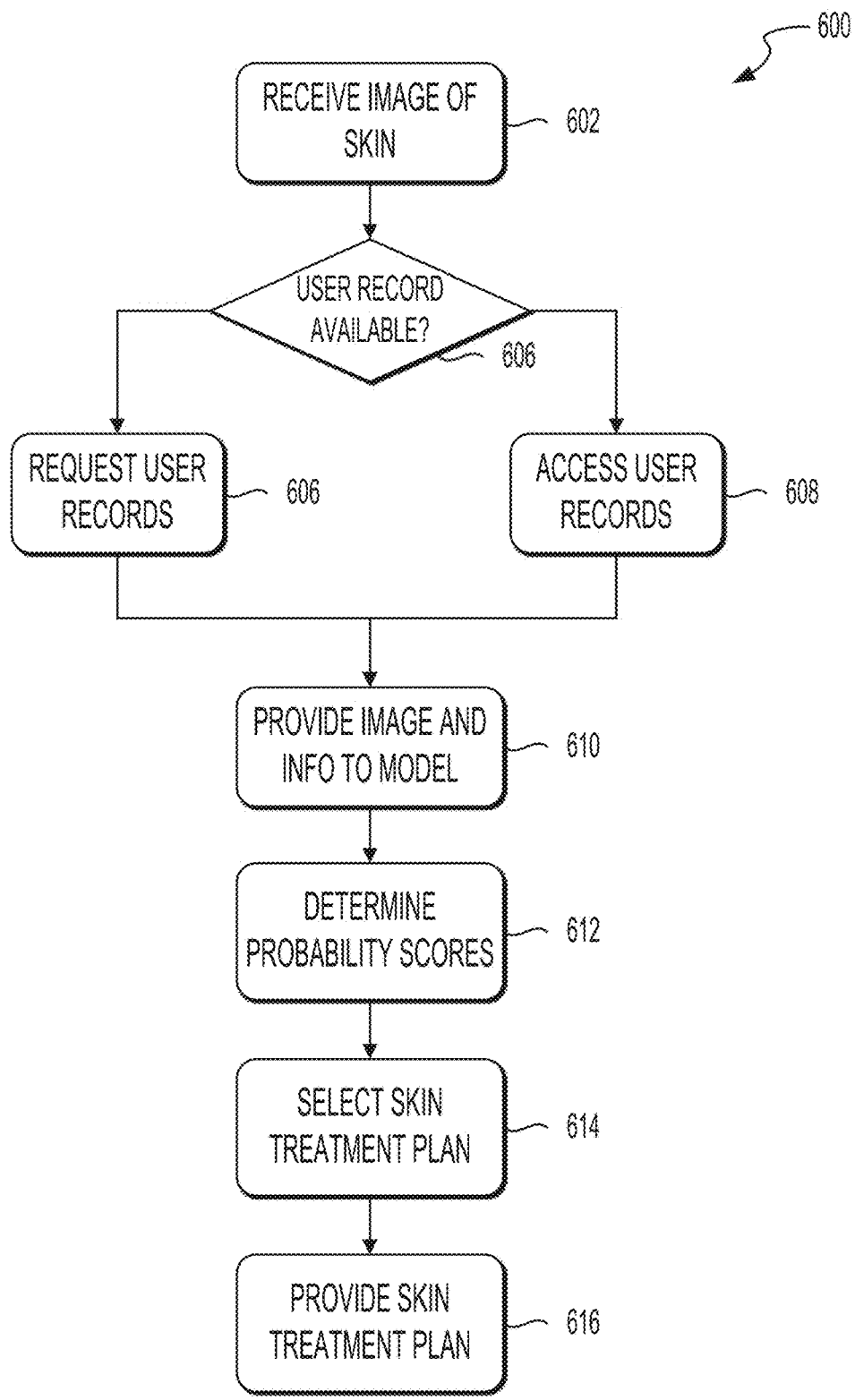
FIG. 6 illustrates an example flow diagram of a method of analyzing skin images to determine a personalized treatment plan.

Referring now to FIG. 6, depicted is an illustrative flow diagram of a method 600 for determining a treatment plan for a classified skin disease or characteristic. The method 600 can be executed, performed, or otherwise carried out by the skin analysis system 120, the computer system 100 described herein in conjunction with FIG. 1A-1D, or any other computing devices described herein. The method 600 can include any of the steps of method 400 described herein in conjunction with FIG. 4 or any of the steps of method 500 described herein in conjunction with FIG. 5. The skin analysis system (e.g., the skin analysis system 120, etc.) can receive, from a camera, one or more images captured of a portion of skin having a potential skin condition (STEP 602). The skin analysis system can determine whether user information (e.g. biometric information, user records such as the user records 320, etc.) is available (STEP 604). The skin analysis system can request one or more medical records or other user information from the mobile device (e.g., the mobile device 102) of the user (STEP 606). The skin analysis system can access user information or medical records of the user from a mobile device of the user (STEP 608). The skin analysis system can provide the image and the medical information as input to a treatment plan determination model. (STEP 610). The skin analysis system can determine one or more probability scores of a set of potential treatment plans based on the output of the treatment determination model (STEP 612). The skin analysis system can select one or more treatment plans based on the probability scores (STEP 614). The skin analysis system can provide the one or more for the user to the mobile device (STEP 616).

The skin analysis system (e.g., the skin analysis system 120, etc.) can receive, from a camera, one or more images captured of a portion of skin having a potential skin condition (STEP 602). In some implementations, an application (e.g., the application 320, etc.) may prompt the user to include at least one reference object with a known color in the photo of skin. An example reference object can be, for example, a new United States dollar bill. In some implementations, the application can transmit a request for a skin diagnosis classification to the skin analysis system. In such implementations, the skin analysis system can receive the request for a skin diagnosis classification (e.g., a disease, status, or characteristic, etc.), which can include the one or more images of the skin of the user. The request for a skin diagnosis can include other information about the user, such as the answers to the questions, any user profile information described herein, or any information received from the user by the application 320 as described in this technical solution. In some implementations, the skin analysis system can receive a request for a personalized treatment plan for a particular skin condition associated with the one or more images. Upon receiving the one or more images of the skin and the user information, the skin analysis system can store the images in the memory of the skin analysis system (e.g., as the skin images 220 or as a part of the skin images 220 in the data storage 315, etc.). In some implementations, skin images for the diseased areas of skin are extant in the data storage 315, and the image receiver 330 can access and retrieve the skin images 220 from the data storage 315 that are associated with the diagnosed skin condition or case.

The skin analysis system can determine whether user information (e.g. biometric information, user records such as the user records 320, etc.) is available (STEP 604). For example, the skin analysis system can determine whether the user has provided answers to one or more biometric questions, medical history questions, answers relating to a potential skin condition (e.g., duration of condition, burning sensation, itching, etc.) such as those detailed herein above in conjunction with FIGS. 3A-3C. In some implementations, the skin analysis system can determine whether the user has stored or provided any information, such as a user profile or user records (e.g., the user records 310 including medical records, medical history, current treatments, etc.) in the memory or the data storage (e.g., the data storage 315, etc.) of the skin analysis system. For example, the skin analysis system can access one or more regions of the memory or data storage of the skin analysis system to identify if there is any user information present, such as a user profile, or any other user information described herein. If the user has not yet provided user information, medical records, or user records, the skin analysis system can perform STEP 606 of the method 600. If the user has provided biometric information or user records, the skin analysis system can perform STEP 608 of the method 600

The skin analysis system can request one or more medical records or other user information from the mobile device (e.g., the mobile device 102) of the user (STEP 606). The skin analysis system can query one or other computing devices (e.g., the other computing devices 360, etc.), such as those that are associated with a previous healthcare provider of the user associated with the skin condition, with at least one request for medical records or other information. The medical record information can include information about the skin condition for which a personalized treatment plan is to be created, such as the duration, severity, and type of diagnosis, characteristics, or other information. The medical records or medical information can include previous treatments attempted by the user, other treatment data, drugs the user has taken or currently takes, or any other medically relevant information. Accessing the medical information can include retrieving other information as needed by the treatment plan determiner to determine a personalized treatment plan of the user. Any such information can be accessed by the skin analysis system via a network 104, the other computing devices, the mobile device, or the data storage of the skin analysis system. For example, the skin analysis system can present one or more questions to the user via the application executing on the mobile device of the user. The skin analysis system can then receive answers to the questions from the mobile device and store in them in association with other user information or case information, such as a user profile, the skin images, or other user provided information or other information gathered about the user.

The skin analysis system can access user information or medical records of the user from a mobile device of the user (STEP 608). The skin analysis system can access medical information of the user received from the mobile device, stored in the user records in the data storage of the skin analysis system, or accessed via at least one of the other computing devices (e.g., the other computing devices 360, etc.). The medical record information can include the answers to any of the questions presented to the user via the application executing on the mobile device as described herein. The medical record information can include any diagnoses or characteristics of the user that is determined by the skin analysis system, such as a diagnosis of a skin condition for a particular case, image, or set of images provided by the user. The medical information can include biometric information, such as a reported skin color of the user, a natural hair color of the user, an eye color of the user, a reported likelihood of burning in the sun my the user, the height of the user, the weight of the user, or any other biometric information as described herein. The skin analysis system can query one or other computing devices, such as those that are associated with a healthcare provider of the user associated with the skin condition, with at least one request for medical records or other information. The medical record information can include information about the skin condition for which a personalized treatment plan is to be created, such as the duration, severity, and type of diagnosis, characteristics, or other information. The medical records or medical information can include previous treatments by the user, treatment data such as previous treatment outcomes, drugs or medications the user has taken or currently takes, or any other medically relevant information. Accessing the medical information can include retrieving other information as needed by the skin analysis system to determine a personalized treatment plan of the user. Any such information can be accessed by the skin analysis system via a network (e.g., the network 104), the other computing devices, the mobile device, or the data storage of the skin analysis system.

The skin analysis system can provide the image and the medical information as input to a treatment plan determination model. (STEP 610). The skin analysis system can provide the data structures that represent the medical information and the diagnosis information as an input layer to a treatment determination model. The treatment determination model can be a neural network that is trained to take, as input, one more data structures that represent a skin diagnosis and user medical information to determine a set of output probabilities corresponding to a respective set of possible treatment plans. The output probabilities can be confidence scores representing a likelihood of a positive treatment outcome. Providing the data structures as an input layer can include normalizing (e.g., scaling the values of the data structures such that their coordinate values are floating point values each between zero and one, etc.). After providing the data structures as input to the skin treatment determination model, the skin analysis system can propagate (e.g., perform the mathematical computations of each layer, etc.) the input data through the treatment determination model until a set of output probabilities corresponding to a respective set of treatment plans are output at an output layer.

The skin analysis system can determine one or more probability scores of a set of potential treatment plans based on the output of the treatment determination model (STEP 612). The skin analysis system can receive a data structure from the trained treatment determination model that includes a set of output probabilities corresponding to a respective set of treatment plans for a particular skin condition. The trained treatment determination model can be implemented by the skin analysis system. The probabilities can correspond to the likelihood of a positive treatment outcome for a treatment for the skin condition given the medical information of the user. The data structure can be a vector that includes a number of coordinates, where each coordinate in the vector can be a probability value, such as a probability value that is between zero and one.

The skin analysis system can select one or more treatment plans based on the probability scores (STEP 614). A probability close to or equal to zero can represent a low likelihood that the corresponding treatment plan will work for the user and the skin condition, and a probability close to or equal to one can represent a high likelihood that the corresponding treatment plan will work for the user and the skin condition. The skin analysis system can select one or more of the positions in the data structure, and the respective diagnosis associated therewith, based on its corresponding probability value. For example, the skin analysis system can compare each of the probability values in the data structure to a predetermined probability threshold. If the probability of a particular position or data entry in the data structure is greater than or equal to the threshold, the skin analysis system can select the treatment plan associated with that position in the data structure as the personalized treatment plan for the skin condition of the user.

The skin analysis system can repeat this process for each position in the data structure to select a set of personalized treatment plans. In some implementations, the skin analysis system can sort the positions in the data structure to create a sorted data structure. In such implementations, the skin analysis system can select a predetermined number of treatment plans (e.g., top five, top ten, etc.) in the data structure that have the greatest value or probability. Of a selected set of treatment plans, the skin analysis system can select the treatment plan associated with the highest probability of success for the user (e.g., the highest probability in the data structure, etc.) The treatment plans can include a description of the treatment plan, the course of the treatment plan, the duration of the treatment plan, one or more prescriptions, instructions for applying the prescriptions, instructions to the user to perform one or more actions to treat the skin condition, or any other information about skin disease treatment The skin analysis system can provide the one or more for the user to the mobile device (STEP 616). For example, the v may transmit a message (e.g., which may be a response message to the request for a personalized treatment plan or a request for a classification of a skin condition, etc.) to the application executing on the mobile device via the network. The message can include, the classification of the one or more diagnoses (e.g., a type of acne, cancer, type rash, dry skin, etc.), a probability value associated with each diagnosis or characteristic, and any other information about the skin diagnosis or characteristics, such as a description of the diagnosis or characteristic. The message can include the personalized treatment plan, including a description of the treatment plan, the course of the treatment plan, the duration of the treatment plan, one or more prescriptions, instructions for applying the prescriptions, instructions to the user to perform one or more actions to treat the skin condition, or any other information about skin disease treatment. The message can include instructions to display the personalized treatment plan for the skin condition, including a description of the treatment plan, the course of the treatment plan, the duration of the treatment plan, one or more prescriptions, instructions for applying the prescriptions, instructions to the user to perform one or more actions to treat the skin condition, or any other information about skin disease treatment, on the display of the mobile device (e.g., in the application 320, etc.). In some implementations, the skin analysis system can store the personalized skin condition for the user in association with one or more user records, such as medical records, the user profile, the images of the diseased skin, or other user information in the data storage of the skin analysis system. The skin analysis system can transmit or otherwise provide the personalized treatment plan for the skin condition to one or more computing devices of a healthcare professional that is associated with the user (e.g., at least one of the other computing devices 360).

Figure 7A:
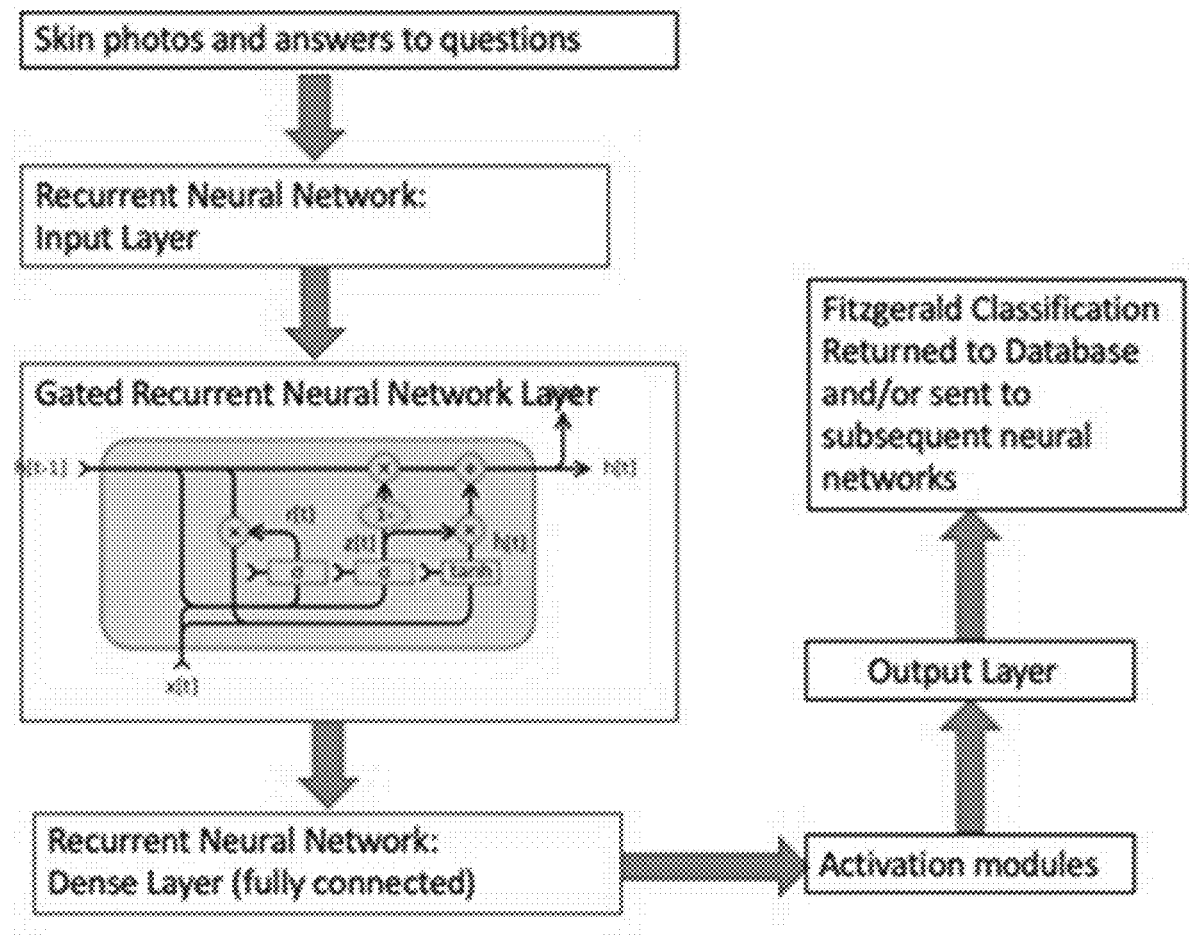
FIG. 7A illustrates an example flow diagram of using a neural network in the classification or identification of a skin score.

Referring now to FIG. 7A, depicted is an example diagram of the use of a recurrent neural network to determine one or more skin color classifications. As depicted in FIG. 7A, the recurrent neural network can be a Fitzpatrick score neural network classifier. Since skin color classification may not depend on fine details in the image, a fairly simple and shallow (e.g., a network with few layers, etc.) network can be used. In one implementation, the classifier can include a gated recurrent neural net architecture.

The systems and methods described herein above can utilize the image data and numerically coded answers to several question as input to the network. This can include numerically coding answers to questions and other data such that the input data is configured as an input vector, matrix, or tensor that is commensurate with the recurrent neural network input layer. The gated neural network can include several layers of gates, which can feed into a dense or fully connected neural network layer. The output of the densely connected layer or layers can be provided as input into one or activation modules, which can include applying (e.g., performing one or more functions on, etc.) activation functions to the data. The activation functions may include, for example, an identity function, a binary step function, a logistic or sigmoid function, a tan h function, an arctan function, a rectified linear unit (ReLu) function, a leaky ReLu function, or a soft-max function, among others. The output of the activation layer can be provided directly as an output layer, and can be a representative skin score (in this example, a Fitzpatrick classification between 1 and 6, etc.). The features and processes associated with the classification of the skin score depicted in FIG. 7A can be carried out, for example, by the skin analysis system 120 described herein above in conjunction with FIGS. 3A-3C. In some implementations, the classification process depicted in FIG. 7A can be carried out by the application 320 executing on the mobile device 102.

Figure 7B:
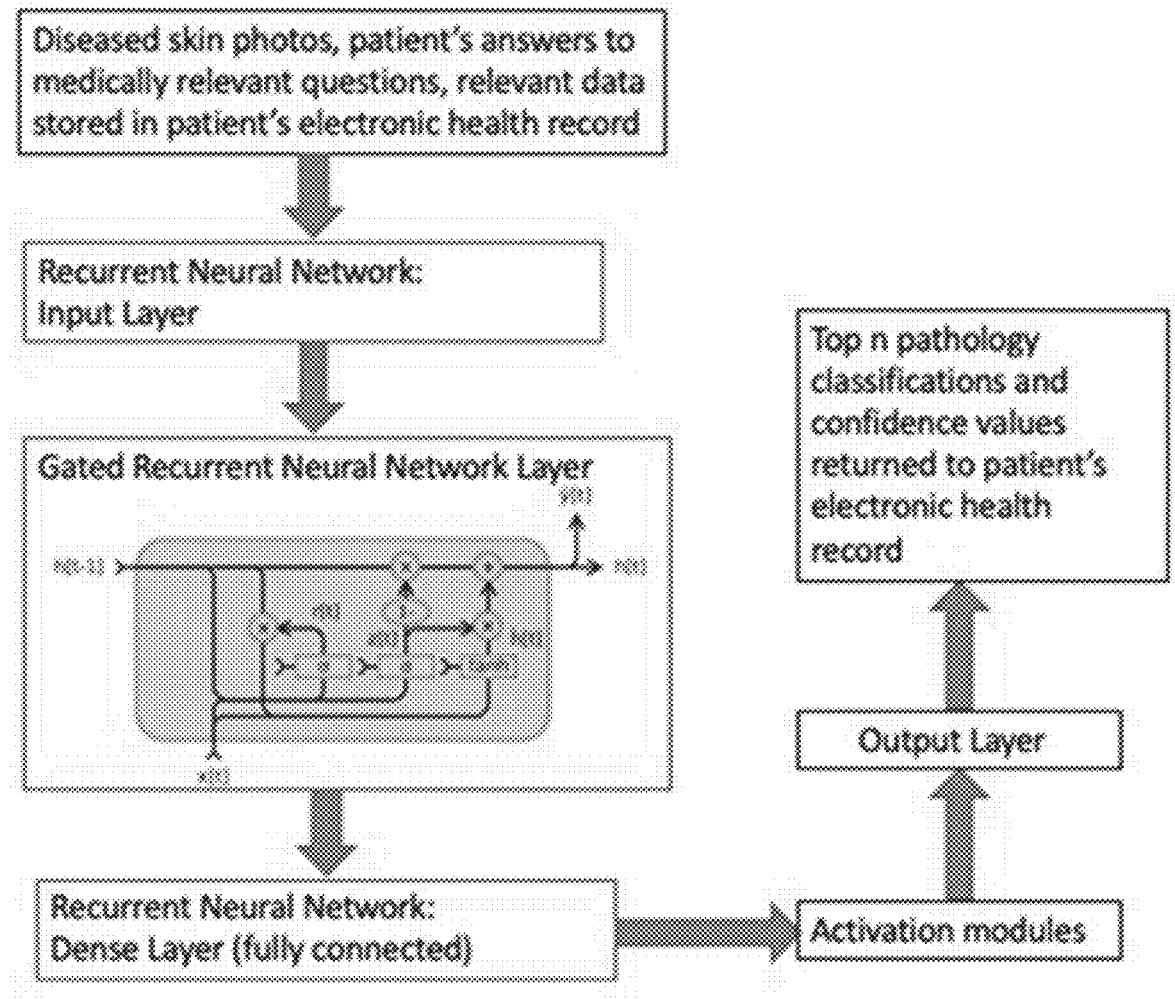
FIG. 7B illustrates an example flow diagram of using a neural network in the determination or selection of one or more skin pathology classifications.

Referring now to FIG. 7B, depicted is an example flow diagram of using a neural network in the determination or selection of one or more skin pathology classifications. The systems and methods of this technical solution can reduce the calculation burden for this neural net by carefully tuning of the number and type of layers and number of parameters while maintaining a high accuracy as measured by the area under the ROC (receiver operating characteristic) curve. In FIG. 7B, the skin pathology classification process can utilize a generalized gated recurrent neural network. In some implementations, a full long-short term memory architecture may be used based on the desired accuracy.

Figure 8A:
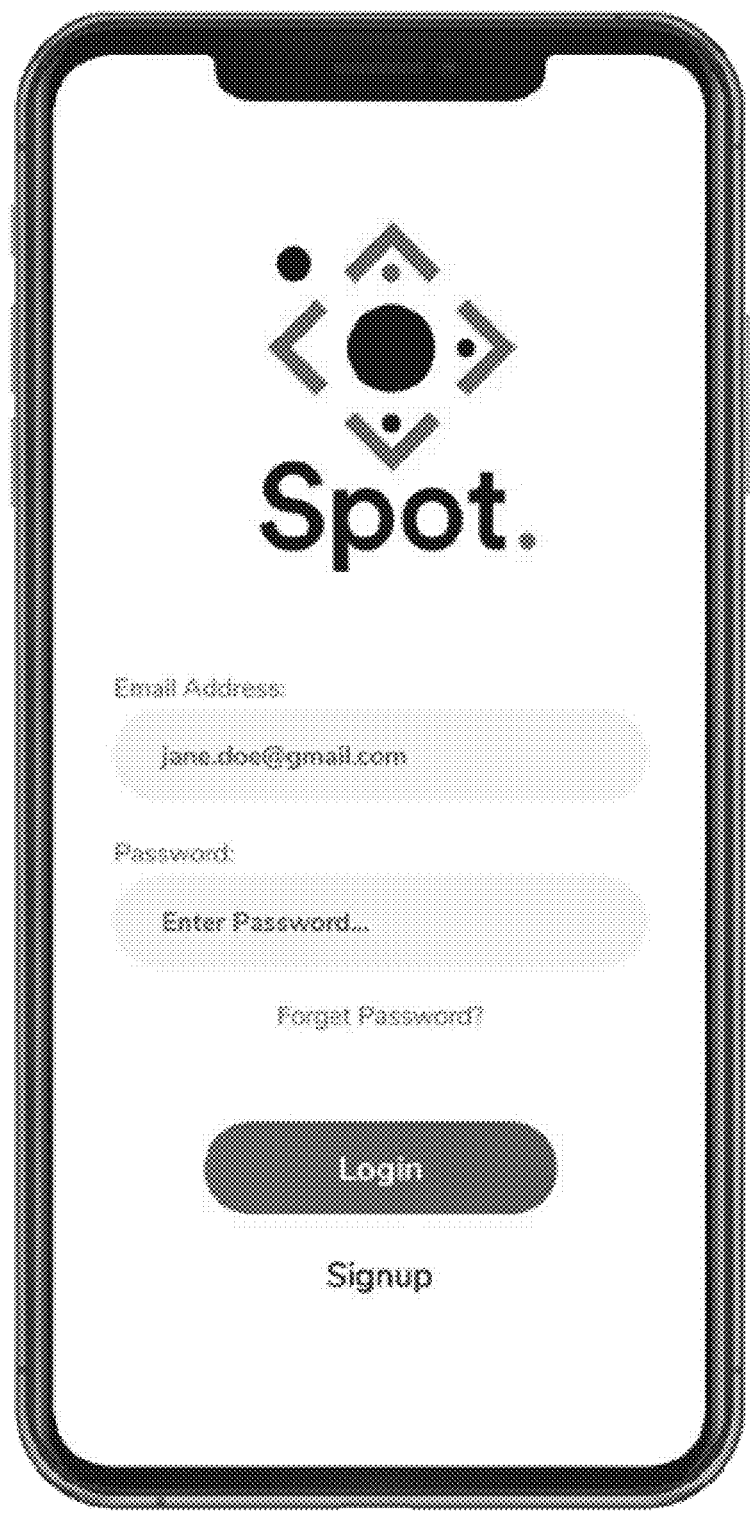
Figure 8B:
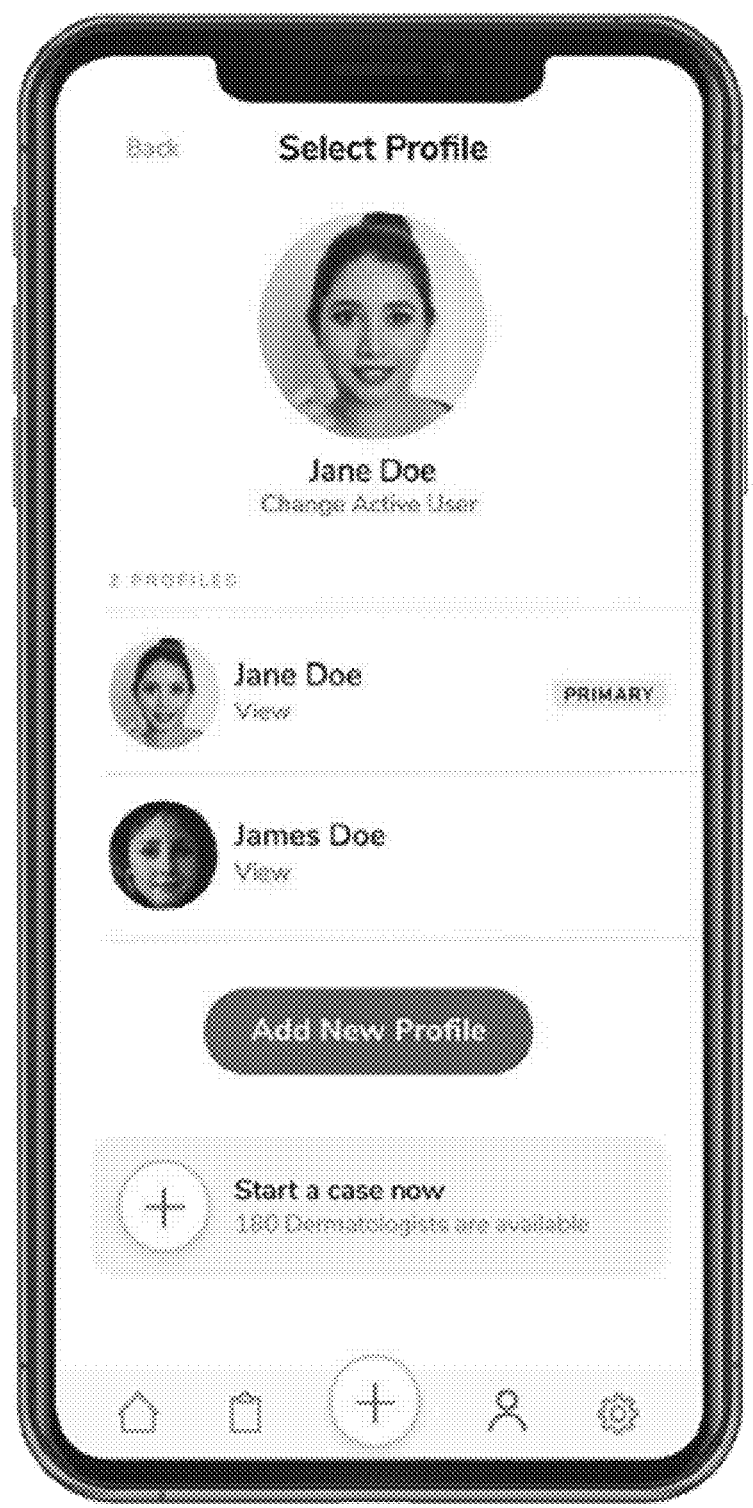
Figure 8C:
Figure 8D:
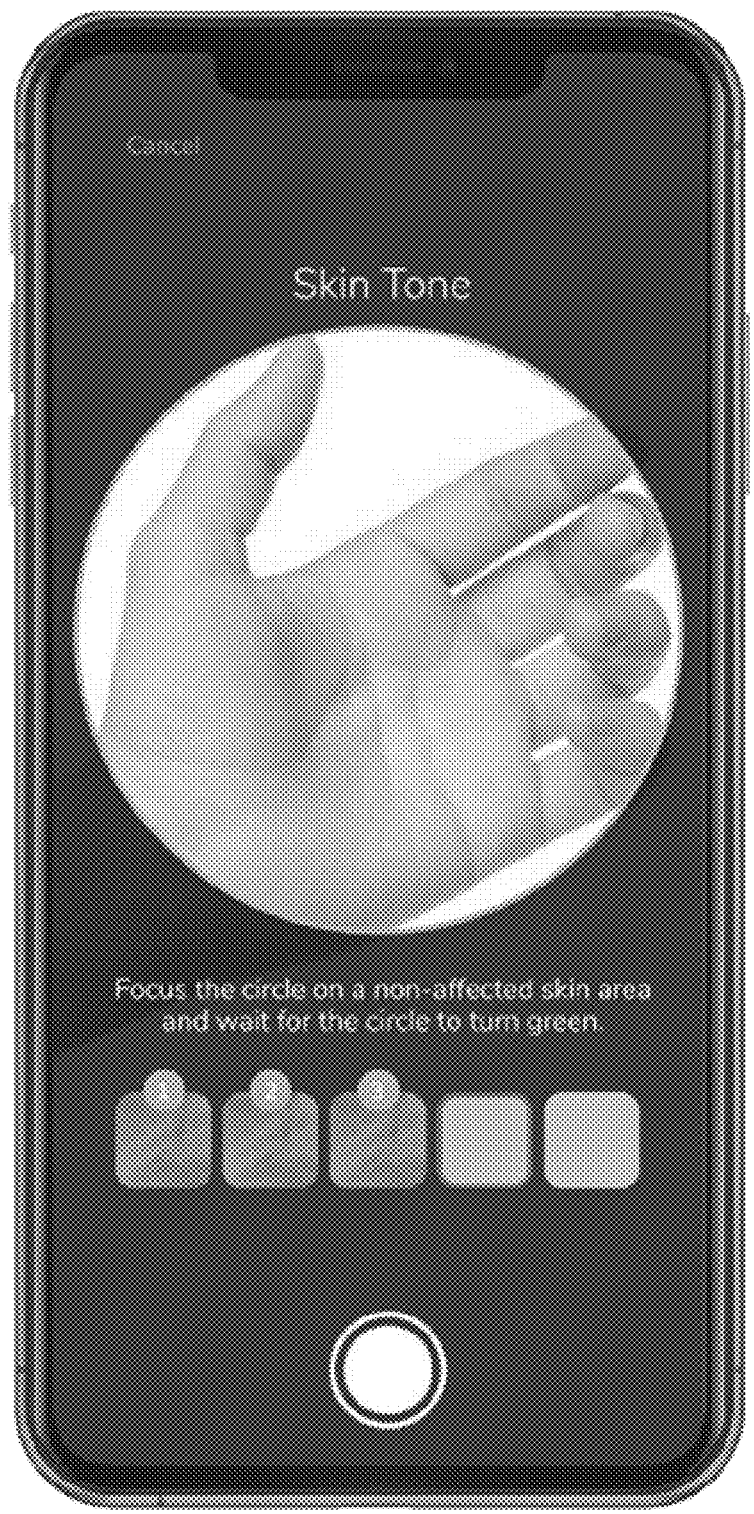
Figure 8E:
Figure 8F:
Figure 8G:
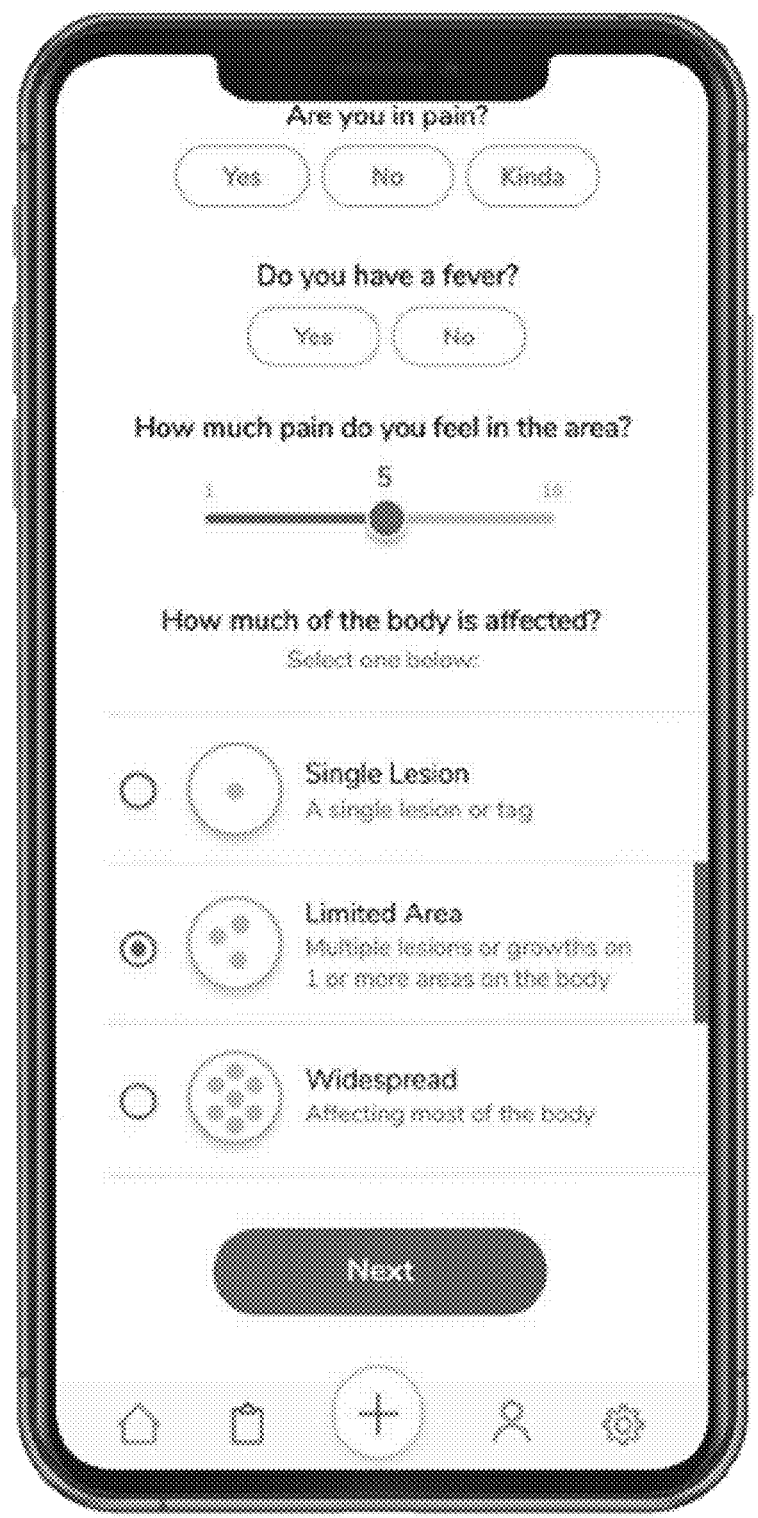
Figure 8H:
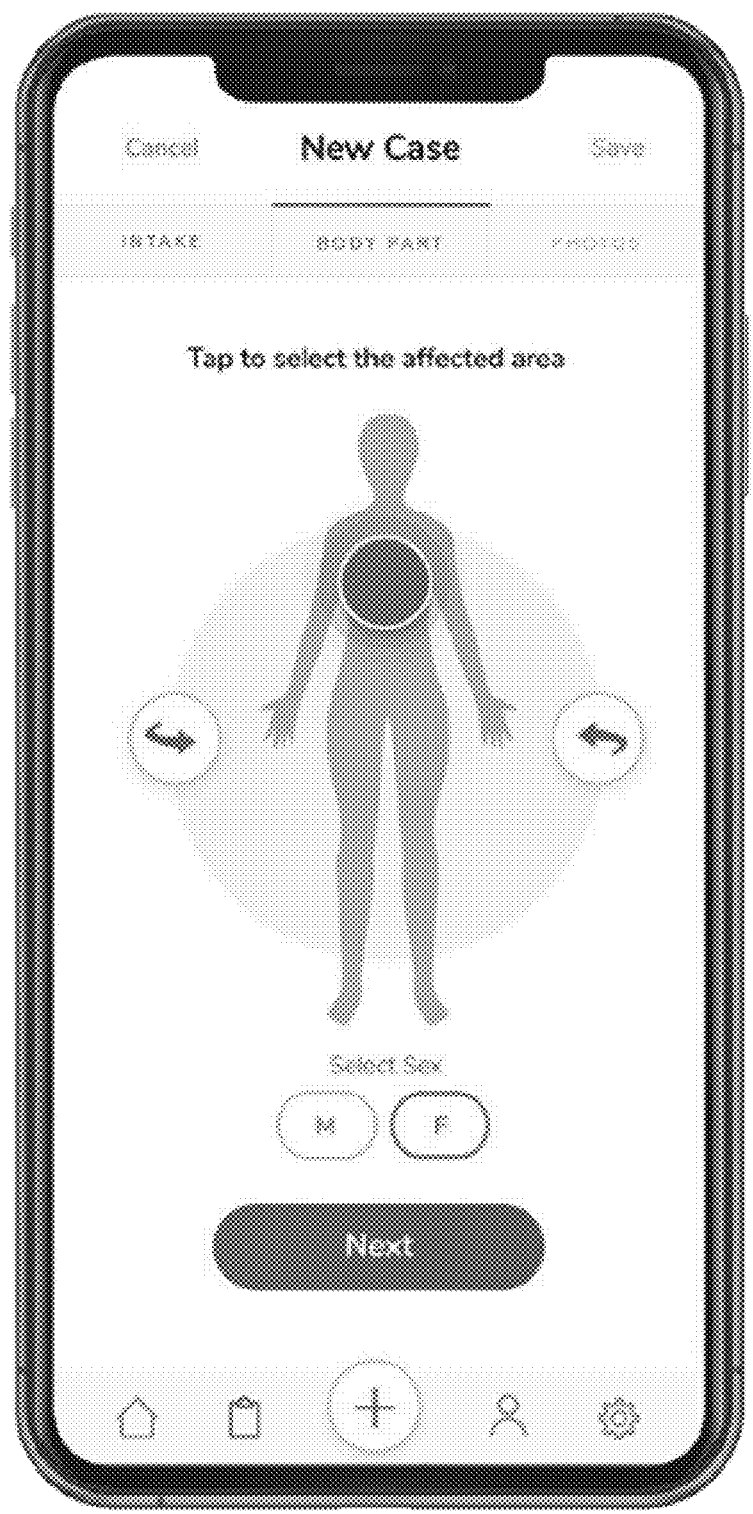
Figure 8I:
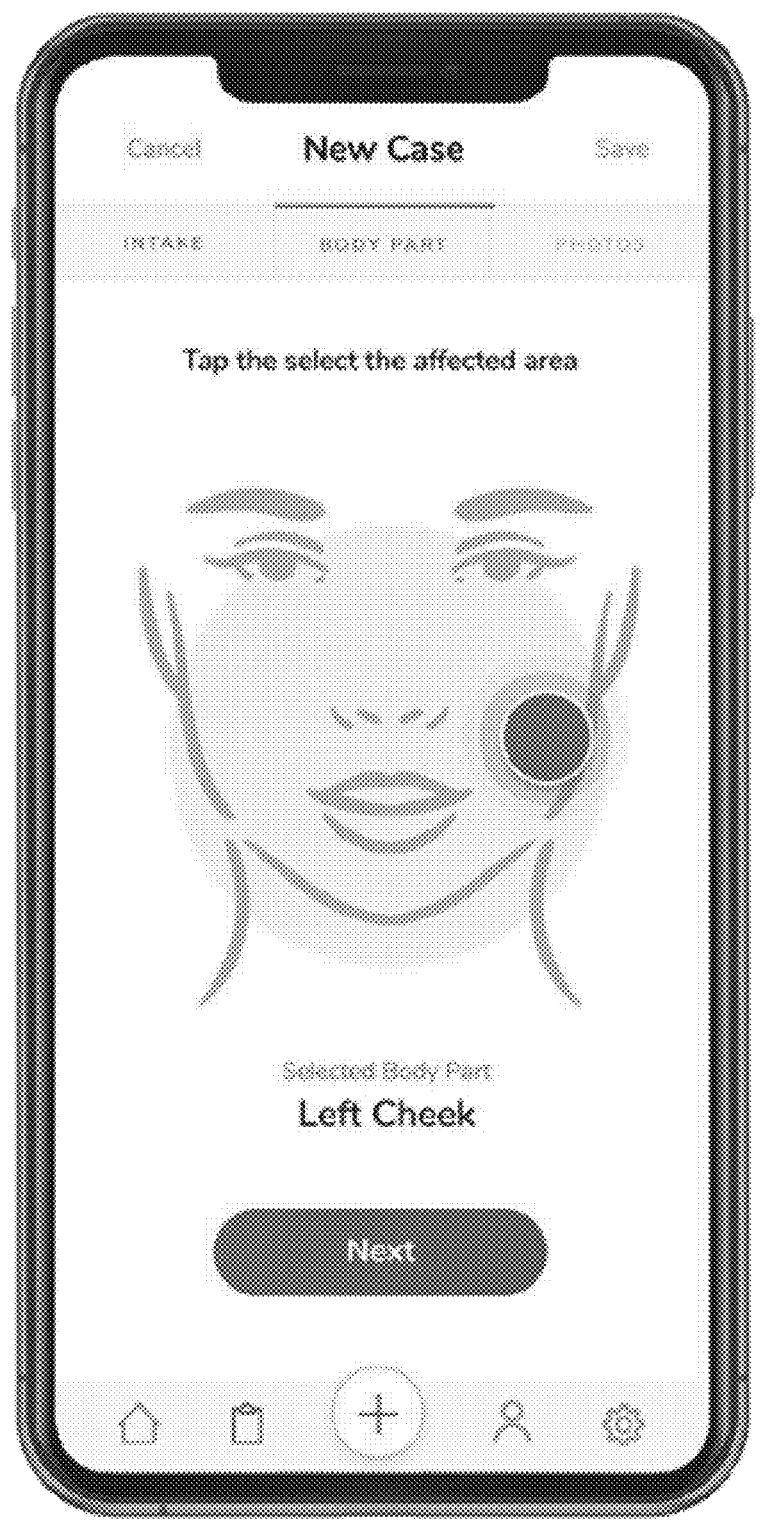
Figure 8J:
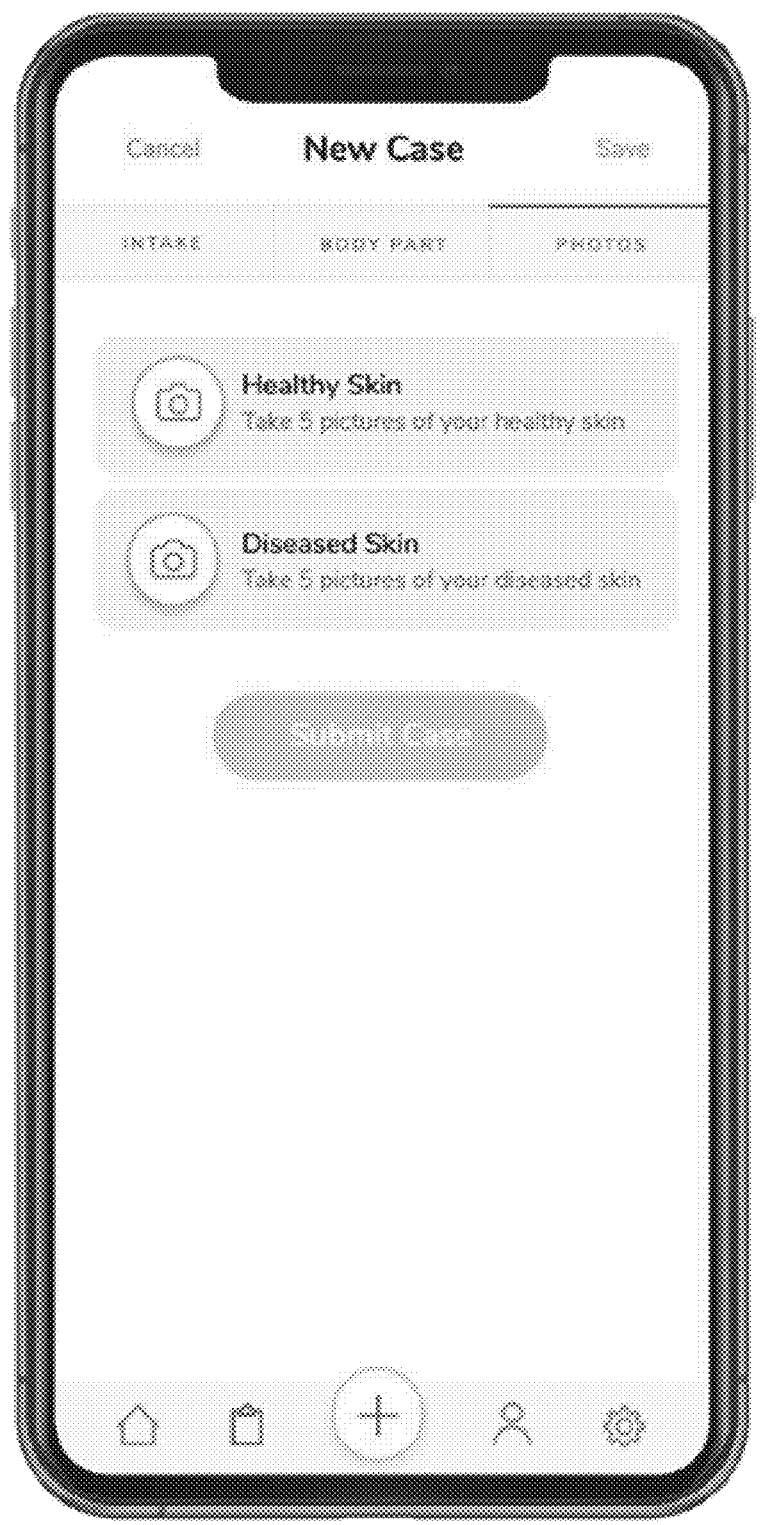
Figure 8K:
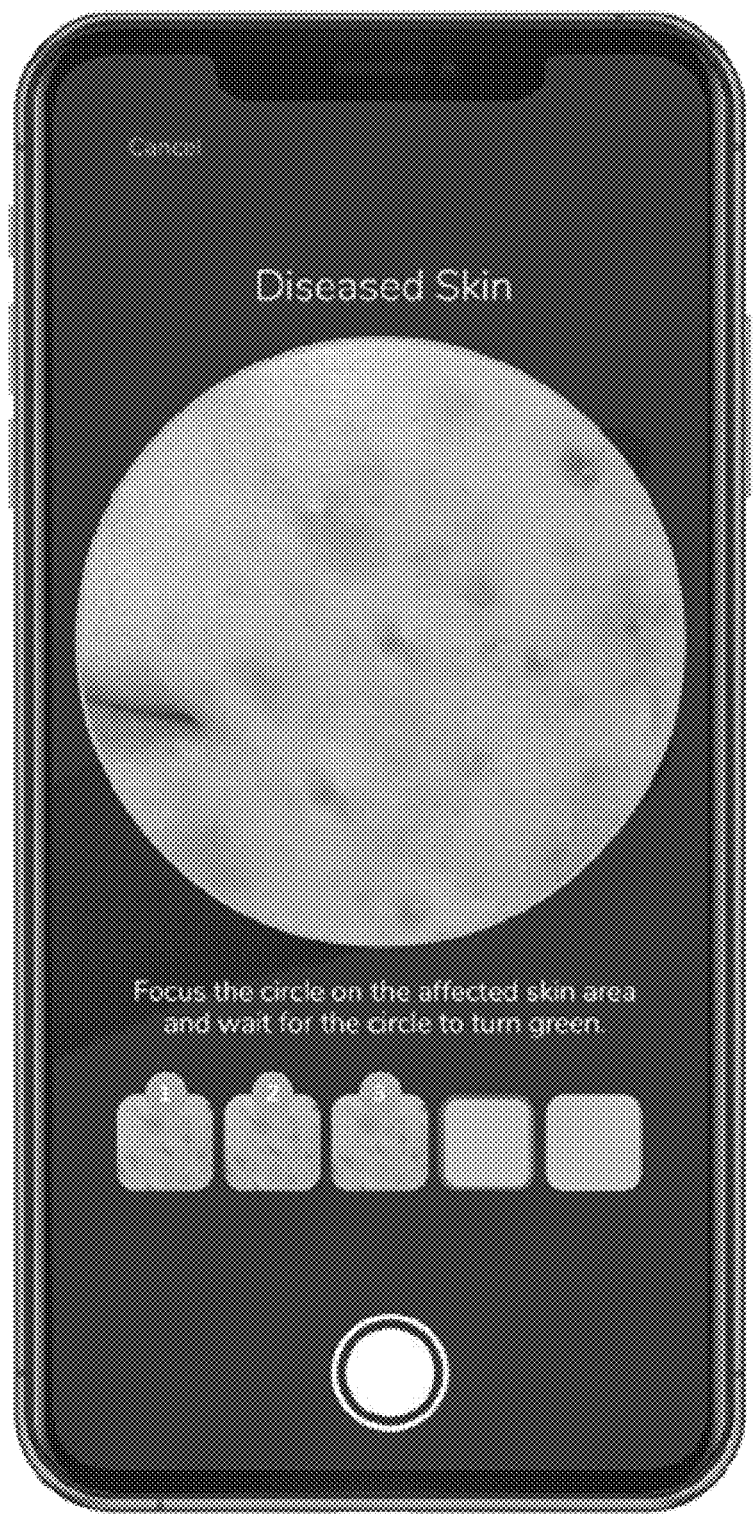
Figure 8L:
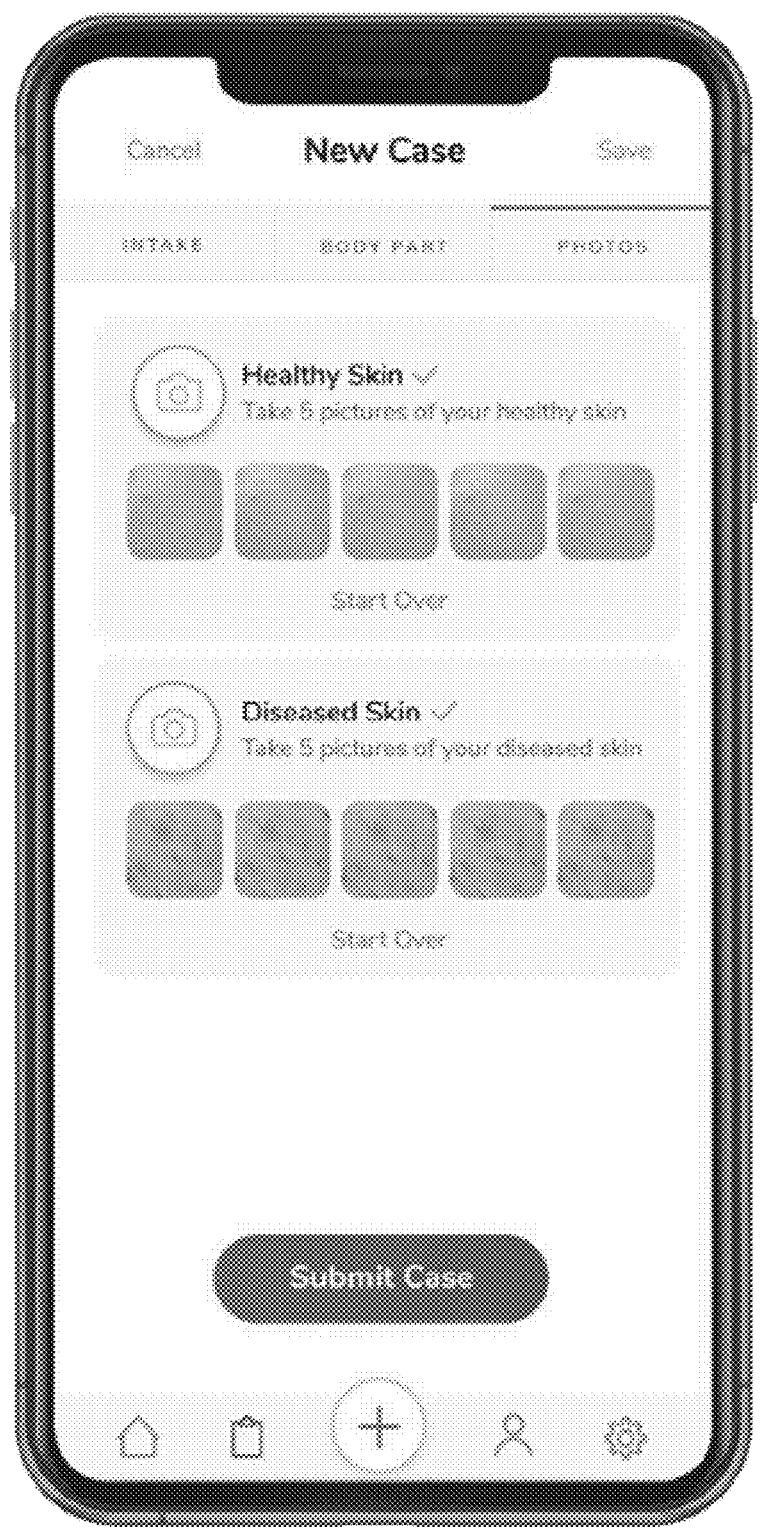
Figure 8M:
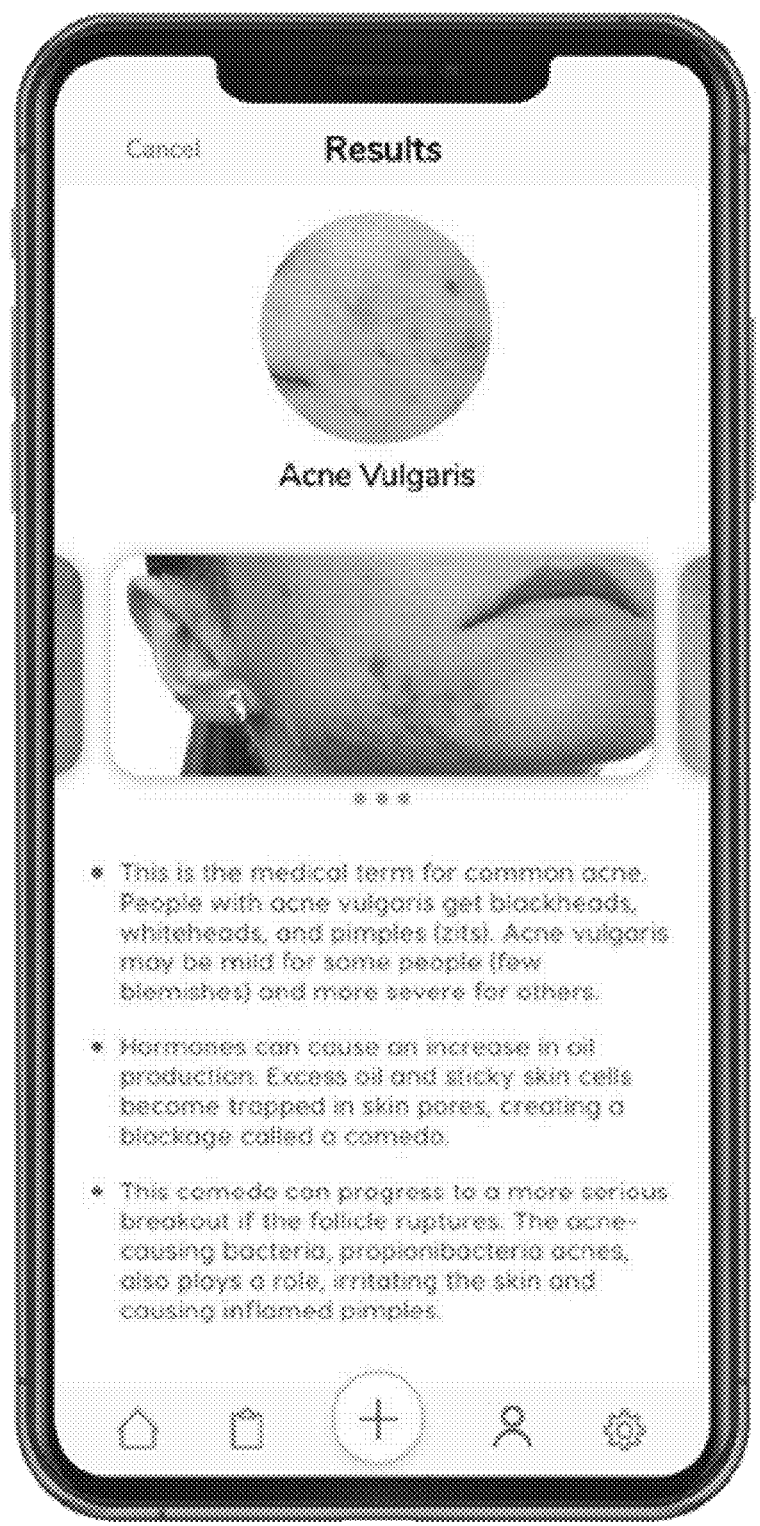
Figure 8N:
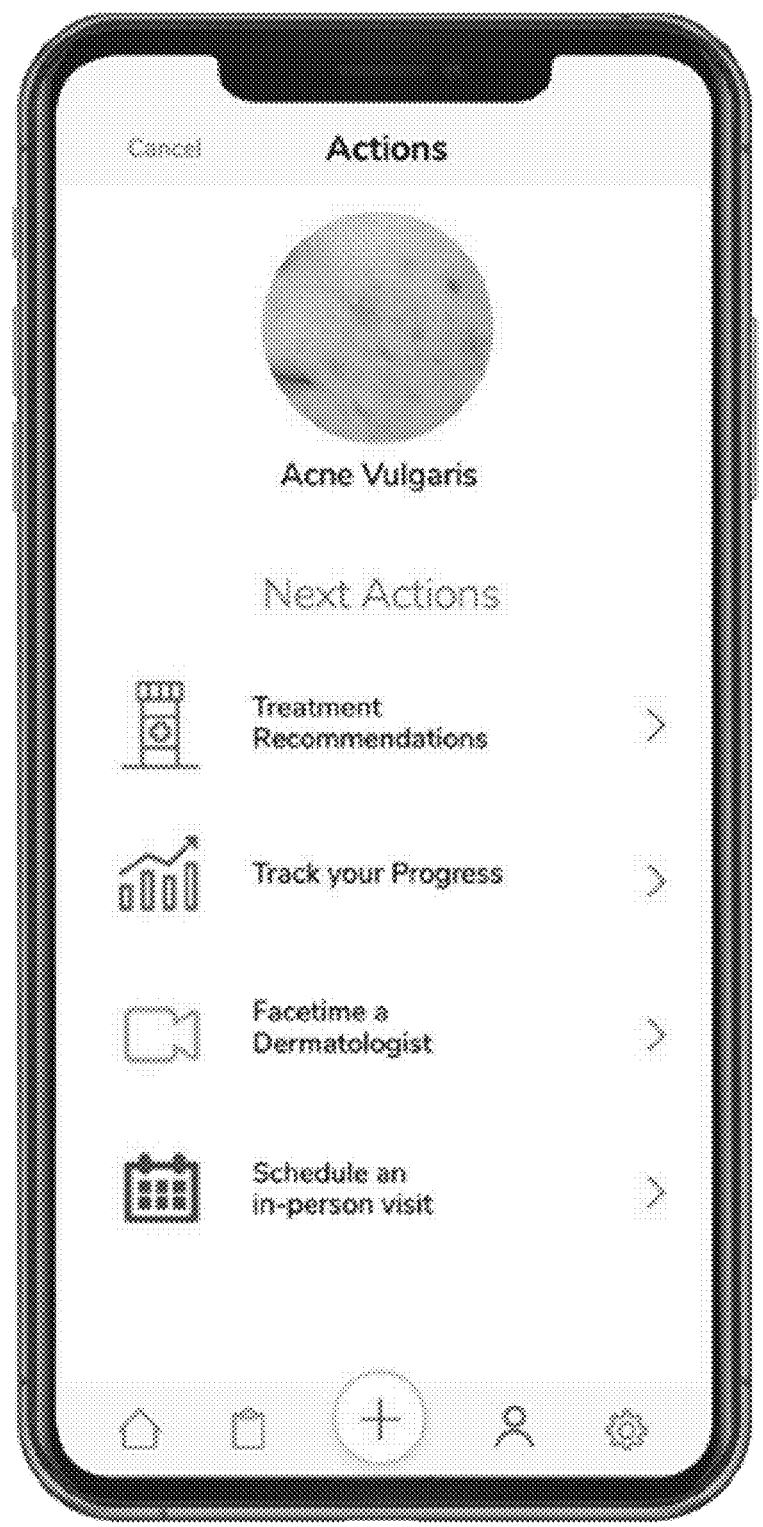
Figure 80:
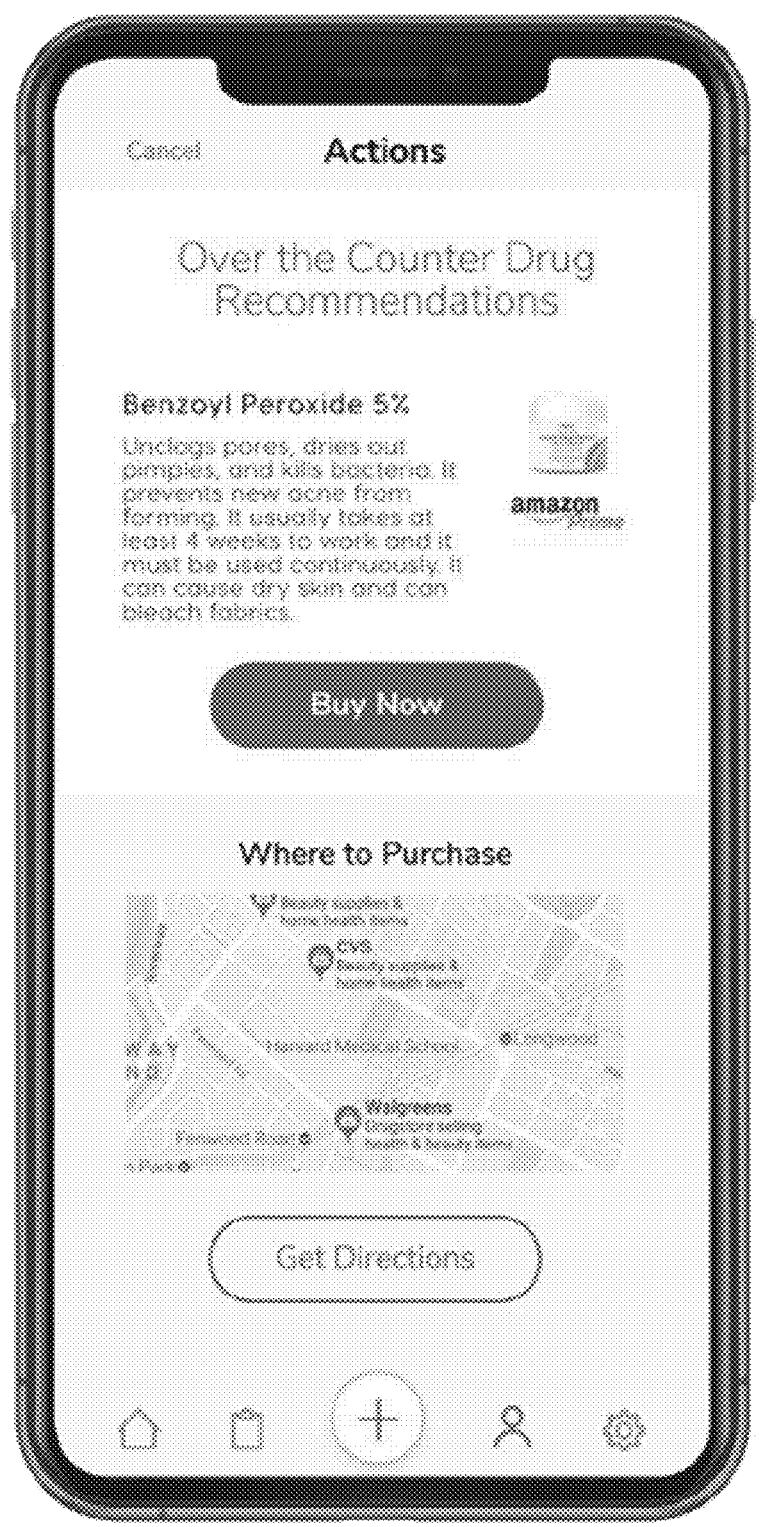
Figure 8P:
Figure 8Q:
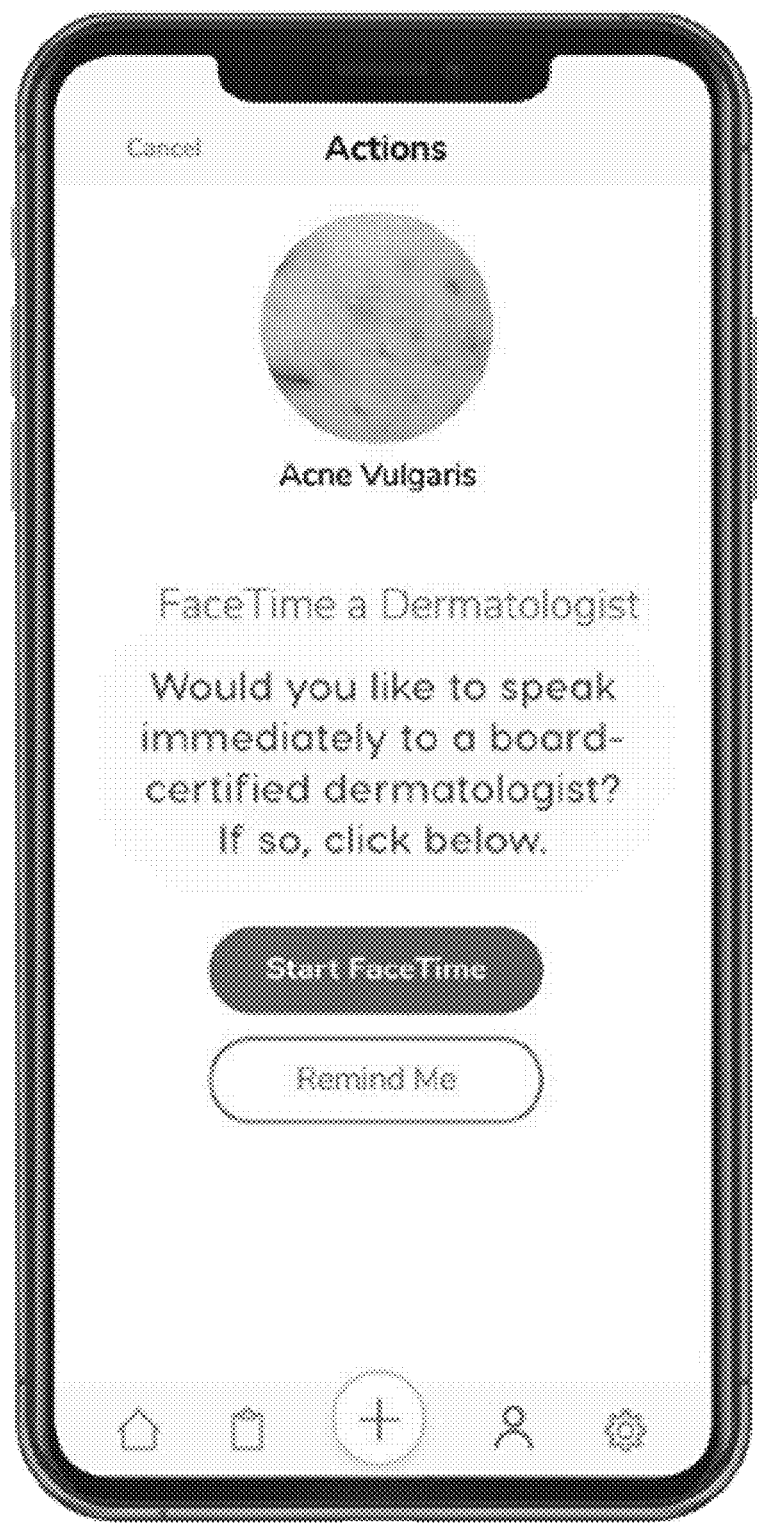
Figure 8R:
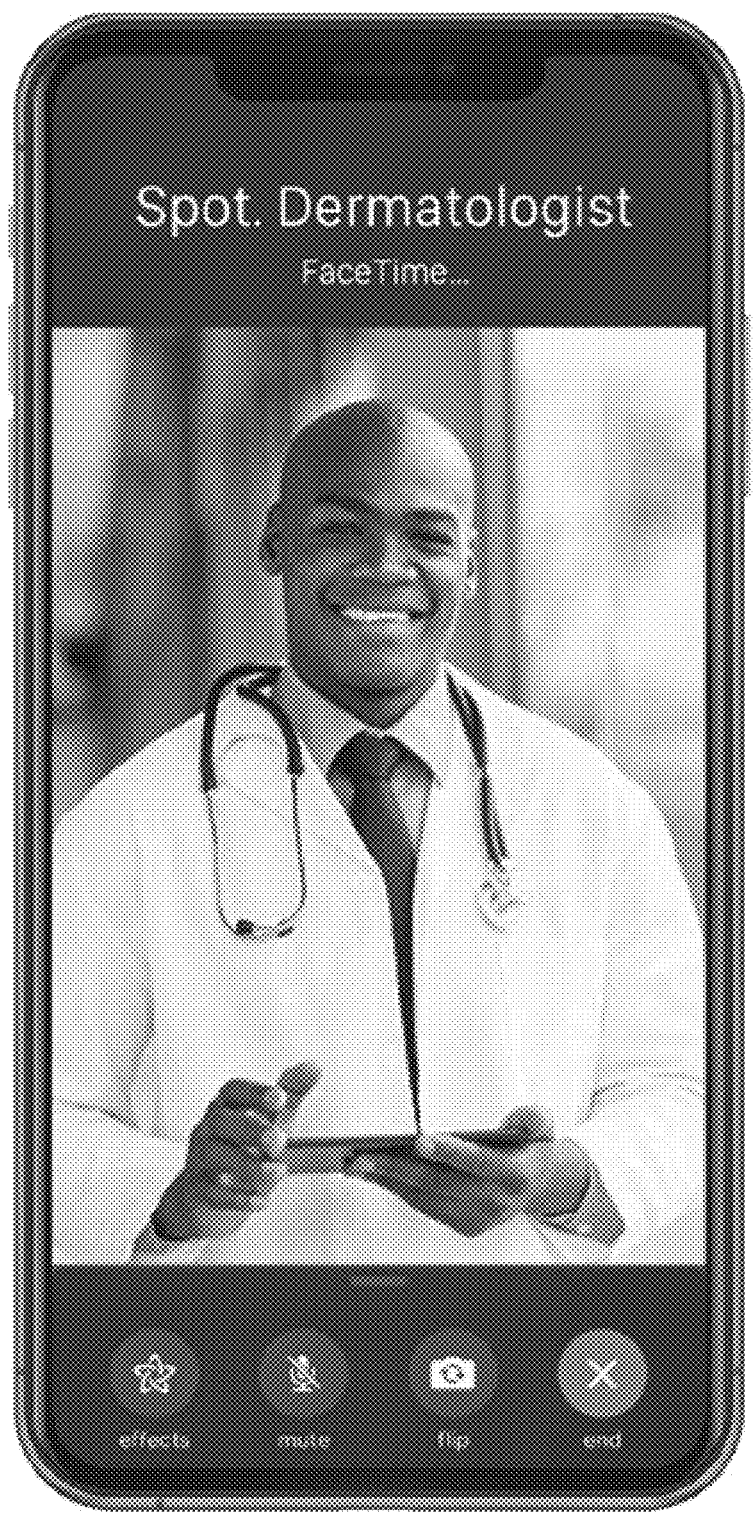
Figure 8S:
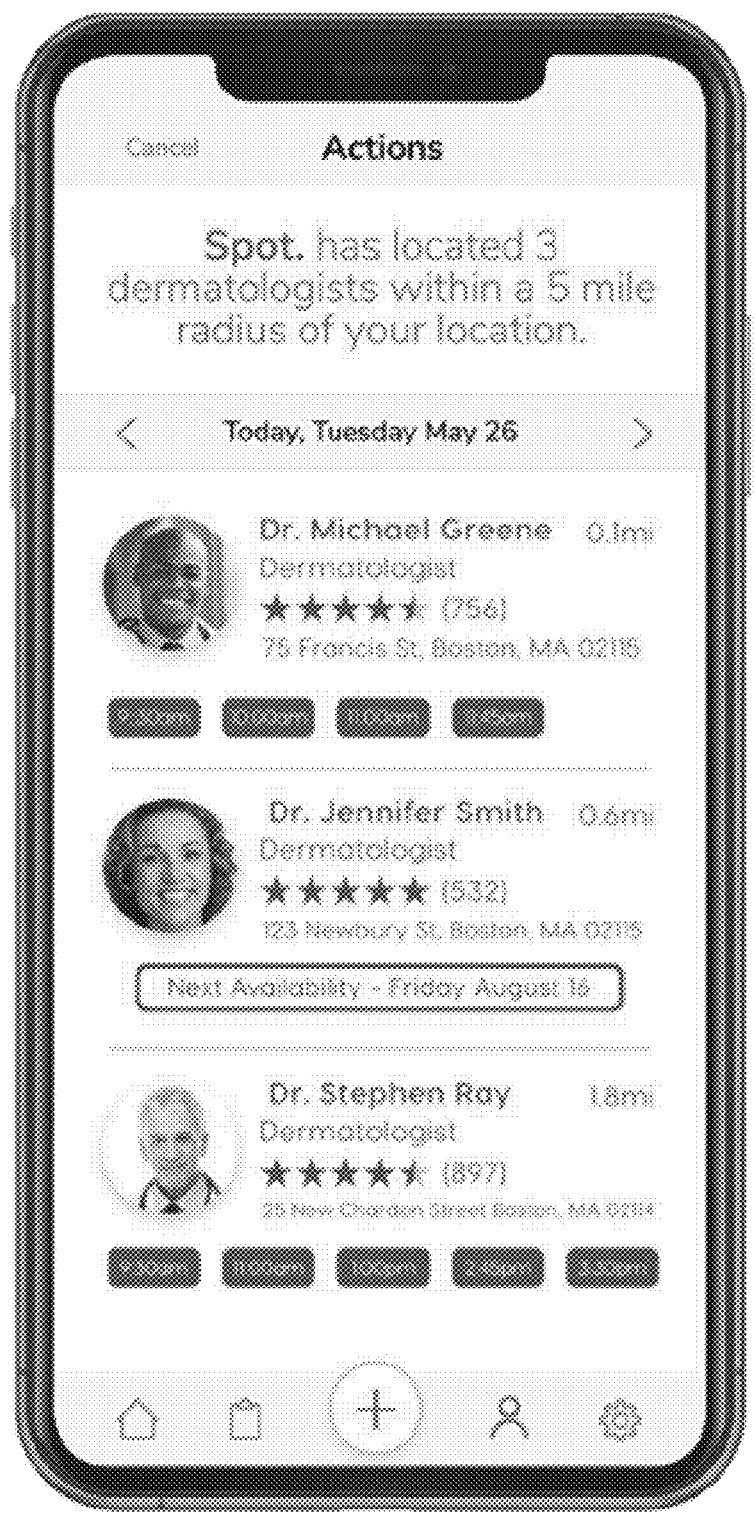

Referring now to FIGS. 8A-8S, depicted are various views of an application (e.g., the application 320, etc.) executing and providing a graphical user interface on a mobile device (e.g., the mobile device 102, etc.). FIG. 8A depicts a login screen for providing user login information. FIG. 8B depicts a graphical user interface for the selection of one or more user profiles or cases. FIG. 8C depicts a graphical user interface for the entry of user profile information and certain biometric information. FIG. 8D depicts a graphical user interface for providing one or more images of skin for the determination of a skin tone value. FIG. 8E depicts a graphical user interface for the selection of one or more cases or skin issues. FIG. 8F depicts a graphical user interface for the selection of one or more answers to questions about a particular case or skin condition. FIG. 8G depicts a continuation of the graphical user interface depicted in FIG. 8F. FIG. 8H depicts the selection of a location on the body of a particular skin condition. FIG. 8I depicts the selection of face location of a skin condition. FIG. 8J depicts the selection of an interface to capture one or more images of healthy skin and one or more images of diseased skin. FIG. 8K depicts a graphical user interface for the capture of one or more images of skin. FIG. 8L depicts a graphical user interface indicating that the requested images have been captured by the application. FIG. 8M depicts a graphical user interface that displays a skin classification or diagnosis and various characteristics of the diagnosis. FIG. 8N depicts a graphical user interface for additional user actions for a diagnosed skin condition. FIG. 8O depicts a graphical user interface displaying at least one treatment plan for the classified skin condition. FIG. 8P depicts a graphical user interface for tracking the progress of a skin condition. FIG. 8Q depicts a graphical user interface to contact a specialist for the classified skin condition. FIG. 8R depicts a graphical user interface to video chat with a selected specialist for the skin condition. FIG. 8S depicts a graphical user interface to create an appointment with a specialist for the classified skin condition.

Figure 9:
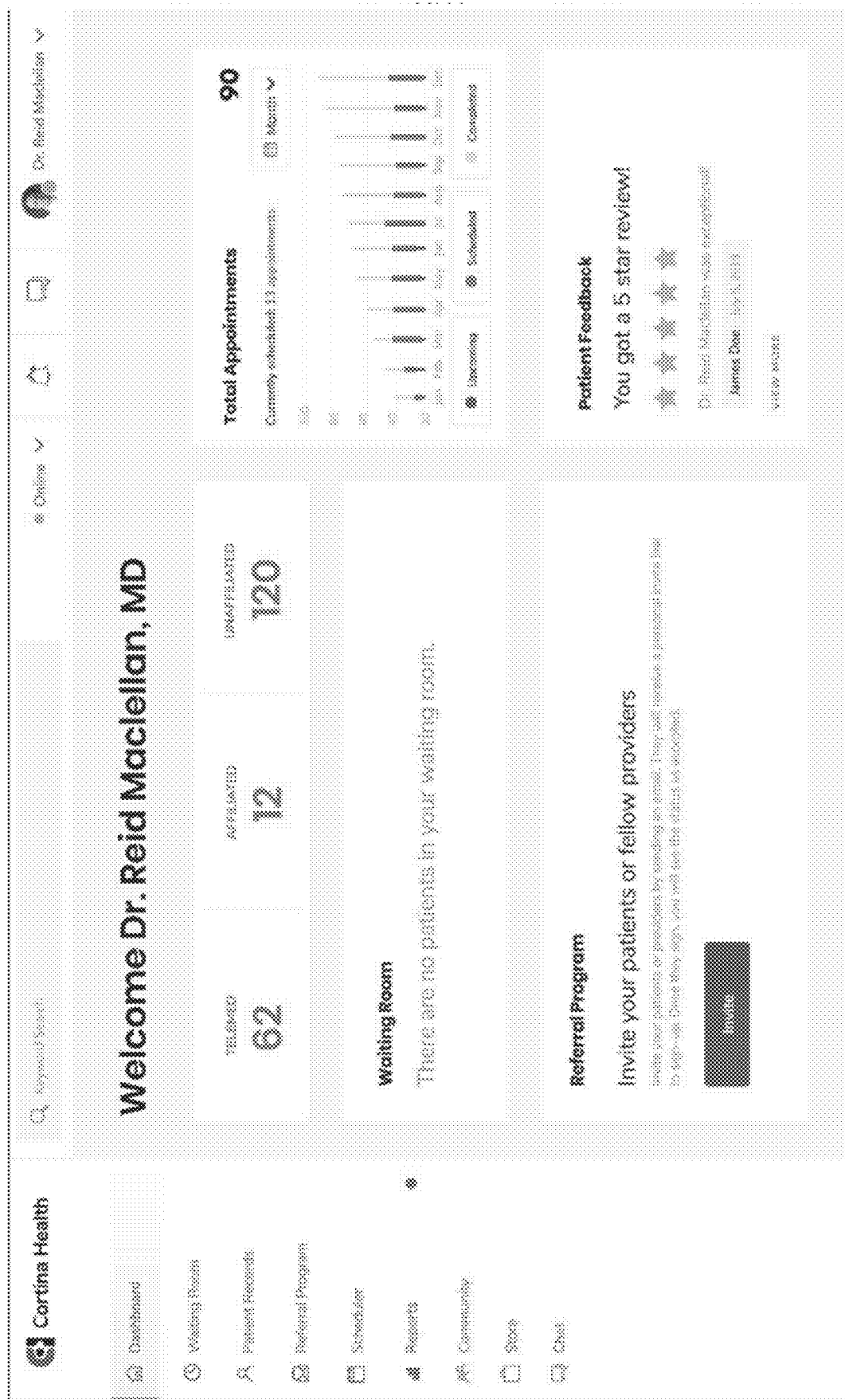
FIG. 9 depicts a graphical user interface for the display of a dashboard of a healthcare professional, that can provide one or more of the functionalities described herein.

Referring now to FIG. 9, depicted is a graphical user interface for a specialist or healthcare professional. Specifically, FIG. 9 displays a dashboard including various selections that include a patient waiting room, patient records, referral program options, appointment schedulers, and other options.

The systems and methods described herein above can utilize the image data and numerically coded answers to several question as input to the network. This can include numerically coding answers to questions and other data such that the input data is configured as an input vector, matrix, or tensor that is commensurate with the recurrent neural network input layer. The gated neural network can include several layers of gates, which can feed into a dense or fully connected neural network layer. The output of the densely connected layer or layers can be provided as input into one or activation modules, which can include applying (e.g., performing one or more functions on, etc.) activation functions to the data. The activation functions may include, for example, an identity function, a binary step function, a logistic or sigmoid function, a tan h function, an arctan function, a rectified linear unit (ReLu) function, a leaky ReLu function, or a soft-max function, among others. The output of the activation layer can be provided directly as an output layer, and can be a set of pathology classifications and confidence values that can be stored in association with the records or data of the user. The features and processes associated with the classification of the skin pathology depicted in FIG. 7B can be carried out, for example, by the skin analysis system 120 described herein above in conjunction with FIGS. 3A-3C. In some implementations, the classification process depicted in FIG. 7B can be carried out by the application 320 executing on the mobile device 102.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs, e.g., one or more components of computer program instructions, encoded on computer storage medium for execution by, or to control the operation of, data processing apparatus. The program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can include a source or destination of computer program instructions encoded in an artificially-generated propagated signal. The computer storage medium can also be, or be included in, one or more separate physical components or media (e.g., multiple CDs, disks, or other storage devices).

The features disclosed herein may be implemented on a smart television module (or connected television module, hybrid television module, etc.), which may include a processing module configured to integrate internet connectivity with more traditional television programming sources (e.g., received via cable, satellite, over-the-air, or other signals). The smart television module may be physically incorporated into a television set or may include a separate device such as a set-top box, Blu-ray or other digital media player, game console, hotel television system, and other companion device. A smart television module may be configured to allow viewers to search and find videos, movies, photos and other content on the web, on a local cable TV channel, on a satellite TV channel, or stored on a local hard drive. A set-top box (STB) or set-top unit (STU) may include an information appliance device that may contain a tuner and connect to a television set and an external source of signal, turning the signal into content which is then displayed on the television screen or other display device. A smart television module may be configured to provide a home screen or top level screen including icons for a plurality of different applications, such as a web browser and a plurality of streaming media services, a connected cable or satellite media source, other web "channels", etc. The smart television module may further be configured to provide an electronic programming guide to the user. A companion application to the smart television module may be operable on a mobile computing device to provide additional information about available programs to a user, to allow the user to control the smart television module, etc. In alternate implementations, the features may be implemented on a laptop computer or other personal computer, a smartphone, other mobile phone, handheld computer, a tablet PC, or other computing device.

The operations described in this specification can be implemented as operations performed by a data processing apparatus on data stored on one or more computer-readable storage devices or received from other sources.

The terms "data processing apparatus", "data processing system", "client device", "computing platform", "computing device", or "device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The elements of a computer include a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), plasma, or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can include any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system such as the skin analysis system 120 can include clients and servers. For example, the skin analysis system 120 can include one or more servers in one or more data centers or server farms. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving input from a user interacting with the client device). Data generated at the client device (e.g., a result of an interaction, computation, or any other event or computation) can be received from the client device at the server, and vice-versa.

While this specification contains many specific implementation details, these should not be construed as limitations on the scope of any inventions or of what may be claimed, but rather as descriptions of features specific to particular implementations of the systems and methods described herein. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. For example, the skin analysis system 120 could be a single module, a logic device having one or more processing modules, one or more servers, or part of a search engine.

Having now described some illustrative implementations and implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementation," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. Although the examples provided may be useful for determining a numerical classification of human skin color, determining one or more characteristics of human skin, or determining individualized treatment plans based on image data received from mobile devices, the systems and methods described herein may be applied to other environments. The foregoing implementations are illustrative rather than limiting of the described systems and methods. The scope of the systems and methods described herein may thus be indicated by the appended claims, rather than the foregoing description, and changes that come within the meaning and range of equivalency of the claims are embraced therein.

What is claimed is:

1. A system for determining a numerical classification of human skin color, comprising:
   a data processing system comprising one or more processors and a memory, the data processing system configured to:
   receive an image captured by a camera, the image depicting a portion of skin of a user having a skin color;
   access biometric information of the user from a computing device of the user;
   determine a classification of the skin color of the user using the image and the biometric information by:
   providing the image and the biometric information as input to a skin color classifier,
   receiving, from an output of the skin color classifier, a plurality of skin color classification output values, and
   selecting the classification of the skin color from the plurality of skin color classification output values having a value greater than another of the plurality of skin color classification output values; and
   provide the classification of the skin color of the user to the computing device.

2. The system of claim 1, wherein the data processing system is further configured to:
   receive a request for a skin color classification; and
   store the classification of the skin color in association with the biometric information received from the computing device of the user.

3. The system of claim 1, wherein the data processing system is further configured to update a model used by the skin color classifier to analyze the image based on the biometric information retrieved from the computing device and an actual classification of the skin color of the user received from the computing device.

4. The system of claim 1, wherein the data processing system is further configured to provide an application to the computing device of the user; and
   wherein the image and the biometric information are received from the application executing on the computing device of the user.

5. The system of claim 1, wherein to determine the classification of the skin color, the data processing system is further configured to format the image prior to providing the image as input to the skin color classifier.

6. The system of claim 1, wherein to format the image, the data processing system is further configured to adjust one or more colors of the image according to a reference color.

7. A system for identifying one or more characteristics of skin, comprising:
   a data processing system comprising one or more processors and a memory, the data processing system configured to:
   receive an image captured by a camera, the image depicting a portion of skin of a user;
   determine, based on the image, a plurality of probability scores that each correspond to a respective one of a plurality of skin characteristics;
   select a skin characteristic of the plurality of skin characteristics based on the plurality of probability scores;
   provide the skin characteristic to a computing device of the user;
   receive a second image of the portion of skin at a later time;
   determine second skin characteristics using the second image; and
   compare the second skin characteristics with the skin characteristic to determine a change in characteristics of the portion of skin.

8. The system of claim 7, wherein the data processing system is further configured to:
   access, from a medical database, a medical record associated with the user; and
   determine the plurality of probability scores further based on the medical record.

9. The system of claim 7, wherein the data processing system is further configured to:
   present a graphical user interface (GUI) providing at least one question about the portion of skin represented by the image;
   receive an answer to the at least one question presented in the GUI; and
   determine the plurality of probability scores further based on at least the answer to the at least one question presented in the GUI.

10. The system of claim 7, wherein the plurality of skin characteristics comprises a diagnosis of one or more skin conditions.

11. The system of claim 10, the data processing system is further configured to determine a diagnosis of a skin condition depicted in the image.

12. The system of claim 11, wherein to determine the diagnosis of the skin condition depicted in the image the data processing system is further configured to determine a severity of the skin condition depicted in the image.

13. A system for analyzing skin images to determine a personalized treatment plan, comprising:
   a data processing system comprising one or more processors and a memory, the data processing system configured to:

receive an image captured by a camera, the image depicting a diseased portion of skin of a user;

access a medical record associated with the user to identify a skin characteristics of the diseased portion of skin represented in the image;

determine a plurality of treatment plans for the diseased portion of skin based on the skin characteristics and the image;

select a first treatment plan of the plurality of treatment plans based on the medical record and at least one of a frequency of prescription of the first treatment plan, outcome data for the first treatment plan, or a historical diagnosis of the user; and provide the first treatment plan to a computing device of the user.

14. The system of claim 13, wherein the data processing system is further configured to:

receive a second image of the diseased portion of skin of the user;

determine a treatment progress of the diseased portion of skin of the user based on the image and the second image; and select a second treatment of the plurality of treatment plans based on the medical record and the treatment progress.

15. The system of claim 14, wherein to determine the treatment progress of the diseased portion of skin of the user, the data processing system is further configured to determine a change in characteristics of the diseased portion of skin between the image and the second image.

16. The system of claim 14, wherein the data processing system is further configured to transmit the treatment progress of the diseased portion of skin to the computing device of the user.

17. The system of claim 14, wherein the data processing system is further configured to store the treatment progress of the diseased portion of skin in the medical record of the user.

* * * * *